United States Patent [19]
Bateson et al.

[11] Patent Number: 6,156,774
[45] Date of Patent: Dec. 5, 2000

[54] BETA-THIOPROPIONYL-AMINO ACID DERIVATIVES AND THEIR USE AS BETA-LACTAMASE INHIBITORS

[75] Inventors: John Hargreaves Bateson, Sawbridgeworth; Desmond John Best, Ware; Brian Peter Clarke, London; Martin Leonard Gilpin, Dorking; David Witty, Hertford, all of United Kingdom

[73] Assignee: SmithKline Beecham P.L.C., Middlesex, United Kingdom

[21] Appl. No.: 09/284,098

[22] PCT Filed: Oct. 10, 1997

[86] PCT No.: PCT/EP97/05709

§ 371 Date: Apr. 7, 1999

§ 102(e) Date: Apr. 7, 1999

[87] PCT Pub. No.: WO98/17639

PCT Pub. Date: Apr. 30, 1998

[30] Foreign Application Priority Data

| Oct. 17, 1996 | [GB] | United Kingdom | 9621692 |
| Mar. 5, 1997 | [GB] | United Kingdom | 9704581 |
| Jul. 31, 1997 | [GB] | United Kingdom | 9716212 |

[51] Int. Cl.[7] .......................... A61K 31/44; C07D 401/02
[52] U.S. Cl. .......................... 514/357; 514/381; 514/383; 514/397; 514/445; 514/563; 546/335; 548/253; 548/255; 548/262.2; 548/335.1; 549/76; 564/442
[58] Field of Search .......................... 540/335; 548/253, 548/255, 262.2, 335.1; 549/76; 564/442; 514/357, 381, 383, 397, 445, 563

[56] References Cited

FOREIGN PATENT DOCUMENTS

| 2 323 680 | 4/1997 | France . |
| 97 30027 | 8/1997 | WIPO . |

OTHER PUBLICATIONS

J.L. Stanton, et al., Angiotensin converting enzyme inhibitors: n–substituted monocyclic and bicylic amino acid derivatives, J. of Med. Chem., vol. 26(9), Sep. 1983, pp. 1267–1277.

M.C. Fournie–Zaluski, et al., New dual inhibitors of neutral endopeptidase and angiotension–converting enzyme: rational design, bioavailability, and pharmacological response in experimental hypertension, J. of Med. Chem., vol. 37(8), Apr. 15, 1994, pp. 1070–1083.

M. Ihara, et al., Synthesis of beta–lactam antibiotics by the sulpheno–cycloamination, J. of Amer. Chem. Soc., vol. 105(25), Dec. 14, 1983, pp. 7345–7352.

H. H. Wasserman, et al., The synthesis of beta–lactams by the cyclisation of beta–halopropionamides, Tetrahedron Letters, No. 6, Feb. 1979, pp. 549–552.

*Primary Examiner*—Zinna Northington Davis
*Attorney, Agent, or Firm*—James M. Kanagy; Charles M. Kinzig

[57] ABSTRACT

Mercapto amino acid derivatives of formula (I), wherein R is hydrogen, a salt-forming cation of a in vivo hydrolysable ester-forming group; $R_1$ is selected from (a) and (b) in which A is a monocyclic aryl or heteroaryl ring and B is a monocyclic aryl, alicyclic or heterocyclic ring, C and D are independently $-Z_p-(CR_8CR_9)_q-$ or $-(CR_8CR_9)_q-Z_p-$ where p is 0 or 1, q is 0 to 3 provided that p+q in C is not 0, $R_8$ and $R_9$ are independently hydrogen or $(C_{1-6})$alkyl or together represent oxo and Z is O, $NR_{10}$ or $S(O)_x$ where $R_{10}$ is hydrogen, $(C_{1-6})$alkyl or aryl$(C_{1-6})$alkyl and x is 0–2, and wherein C and D are linked ortho to one another on each of the rings A and B in formula (b); $R_2$ is hydrogen, $(C_{1-6})$alkyl or aryl$(C_{1-6})$alkyl; $R_3$ is hydrogen, $(C_{1-6})$alkyl optionally substituted by up to three halogen atoms, $(C_{3-7})$cycloalkyl, fused aryl$(C_{3-7})$cycloalkyl, $(C_{3-7})$cycloalkyl$(C_{2-6})$alkyl, $(C_{2-6})$alkenyl, $(C_{2-6})$alkynyl, aryl, aryl—$(CH_2)_m$—X—$(CH_2)_n$, heterocyclyl or heterocyclyl—$(CH_2)_m$—X—$(CH_2)_n$, where m is 0 to 3, n is 1 to 3 and X is O or $S(O)_x$ where x is 0–2 or a bond; $R_4$ is hydrogen or an in vivo hydrolysable acyl group; and $R_5$ and $R_6$ are independently hydrogen and $(C_{1-6})$alkyl or together represent $(CH_2)_r$, where r is 2 to 5; for use in treatment of bacterial infections in humans or animals by administration in combination with a β-lactam antiobiotic.

16 Claims, No Drawings

BETA-THIOPROPIONYL-AMINO ACID DERIVATIVES AND THEIR USE AS BETA-LACTAMASE INHIBITORS

This application is a continuing application under 35 U.S.C. §371 of PCT/EP97/05709 filed Oct. 10, 1997.

This invention relates to chemical compounds having metallo-β-lactamase inhibitory and antibacterial properties. The invention also relates to methods for the preparation of such compounds, to pharmaceutical compositions containing them, and to uses thereof.

Metallo-β-lactamases confer resistance to the vast majority of β-lactam based therapies, including carbapenems and jeopardise the future use of all such agents. As a result of the increased use of carbapenems and other β-lactam antibiotics the clinical climate is becoming more favourable for the survival of clinical strains which produce metallo-β-lactamases, and metallo-β-lactamases have now been identified in common pathogens such as *Bacillus fragilis*, *Klebsiella*, *Pseudomonas aeruginosa* and *Serratia marcescens*. Emerging knowledge emphasises that metallo-β-lactamases have the potential to present a crisis situation for antimicrobial chemotherapy.

U.S. Pat. No. 4,513,009 discloses amino derivatives including thiorphan having enkephalinase-inhibiting, antalgic, antidiarrhea and hypotensive. Analgesic effects are disclosed for thiorphan (B. P. Roques et al, *Nature*, 1980, 288, 286) and for other mercapto amino acid derivatives (JO 3002-117-A). Mercapto amino acid derivatives are disclosed as inhibitors of angiotensin-converting enzyme (ACE) (J. L. Stanton, et al., *J. Med. Chem.*, 1983, 26, 1257, U.S. 4053-651 and GB 2090-591); as conferring antihypotensive effects (WO 9308162); as enkephalinase (neutral endopeptidase (NEP)) inhibitors (U.S. 4474-799 and Mimura et al., *J. Med. Chem.* 1992, 35, 602 and references cited therein); as dual inhibitors of ACE and NEP (fournie-Zaluski et al.,*J. Med. Chem.*, 1994, 37(8), 1070, WO 9417036 and *Biiorg. Med. Chem. Lett.*, 1996, 6(17), 2097); as inhibitors of endothelian-converting enzyme (ECE) (WO 9311154, Burtenshaw, et al, *Bioorg. Med. Chem. Lett.*, 1993, 3(10), 1953 and Deprez et al., *Bioorg. Med. Chem. Lett.*, 1996, 6(19)); as metalloproteinase inhibitors (WO 9425435); and having radioprotective action and cytotoxicity (M. Hikita et al, *J. Radiat. Res.*, 1975, 16(3), 162 and DE2,349,707). DE3819539 (Squibb) discloses amino acids and peptide derivatives as inhibitors of neutral endopeptidase and their use as antihypertensives and diuretics.

Other references to amino acid derivatives having the abovementioned activities include: Gordon et al., Life Sciences 1983, 33 (Supp. I), 113-6; Waller et al., J, Med. Chem. 1993, 36, 2390–2403; Saunders et al., J. Comp. Aided Mole. Des. 1987, 1, 133–42; Gomez-Monterrey et al., J. Med. Chem. 1993, 36, 87–94; Oya et al., Chem. Pharm. Bull. 1981, 29(4), 940–7; Trapani et al., Biochem. Mol. Biol. Int 1993, 31(5), 861–7; Baxter et al., J. Med. Chem. 1992, 35(20), 3718–20; Condon et al., J. Med. Chem. 1982, 25(3), 250–8; Cheung et al., J. Biol. Chem. 1980, 255(2), 401–7; Cushman et al., Biochemistry 1977, 16(25), 5484–91; EP0539848, EP0419327, EP0254032, EP0355784, EP0449523, EP0153755, U.S. Pat. No. 5,061,710, U.S. Pat. No. 4,339,600, U.S. Pat. No. 4,401,677, U.S. Pat. No. 4,199,512, DE2717548. DE2711225, JP54052073, JP54063017, JP54092937, JP55055165. JP54063017, WO9407481, WO8202890, BE890398, and WO97/24341 and WO97/24342 both published Jul. 10, 1997.

Other amino acid derivatives are described by: Fuchs et al., Arzneim.-Forsch. 1985, 35(9)1394–402, having mitochondrial dysfunction and postischemic myocardial damage activity; Rajkovic et al., Biochem. Pharmacol. 1984, 33(8), 1249–50, having enhancement of neutrophil response and modulation of superoxide and hydrogen peroxide production; Sakurai et al., Chem. Pharam. Bull. 1979, 27(12), 3022–8 forming a peptide/cytochrome P-450 heme system; and Sugiura et al., J. Am. Chem. Soc. 1977, 99(5), 1581–5, forming copper(II) and nickel(II) complexes.

WO97/30027 published Aug. 21, 1997 discloses certain amino acid derivatives which have metallo-β-lactamase inhibitory properties.

A novel series of amino acid derivatives have now been discovered, which compounds have metallo-β-lactamsae inhibitory properties, and are useful for the treatment of infections in animals.

According to the present invention there is provided a compound of formula (I) or a pharmaceutically acceptable salt, solvate or in vivo hydrolysable ester thereof:

(I)

$$R_4S\!-\!\!-\!\!C(R_5R_6)\!-\!\overset{+}{C}H(R_3)\!-\!CON(R_2)\!-\!\overset{*}{C}H(R_1)\!-\!CO_2R$$

wherein

R is hydrogen, a salt forming cation or an in vivo hydrolysable ester-forming group;

$R_1$ is selected from (a)

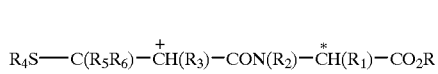

(b)

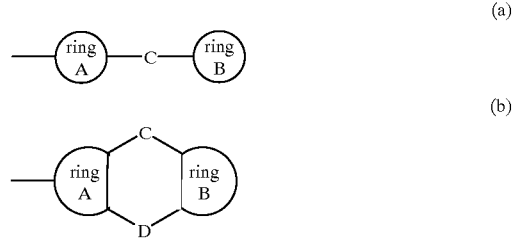

in which A is a monocyclic aryl or heteroaryl ring and B is a monocyclic aryl, alicyclic or heterocyclic ring, C and D are independently $-Z_p-(CR_8R_9)_q-$ or $-(CR_8R_9)_q-Z_p$ where p is 0 or 1, q is 0 to 3 provided that p+q in C is not 0, $R_8$ and $R_9$ are independently hydrogen or $(C_{1-6})$alkyl or together represent oxo and Z is O, $NR_{10}$ or $S(O)_x$ where $R_{10}$ is hydrogen, $(C_{1-6})$alkyl or aryl$(C_{1-6})$alkyl and x is 0–2, and wherein C and D are linked ortho to one another on each of rings A and B in formula (b):

$R_2$ is hydrogen, $(C_{1-6})$alkyl or aryl$(C_{1-6})$alkyl;

$R_3$ is hydrogen, $(C_{1-6})$alkyl optionally substituted by up to three halogen atoms, $(C_{3-7})$cycloalkyl, fused aryl$(C_{3-7})$cycloalkyl, $(C_{3-7})$cycloalkyl$(C_{2-6})$alkyl, $(C_{2-6})$alkenyl, $(C_{2-6})$alkynyl, aryl, aryl-$(CH_2)_m$-X-$(CH_2)_n$-, heterocycl or heterocyclyl-$(CH_2)_m$-X-$(CH_2)_n$-, where m is 0 to 3, n is 1 to 3 and X is O, $S(O)_x$ where x is 0–2 or a bond;

$R_4$ is hydrogen, or an in vivo hydrolysable acyl group; and $R_5$ and $R_6$ are independently hydrogen and $(C_{1-6})$alkyl or together represent $(CH_2)_r$ where r is 2 to 5.

The compound of formula (I) may exist in a number of isomeric forms, all of which, including racemic and diastereoisomeric forms, are encompassed within the scope of the present invention.

It is preferred that the stereochemistry at the carbon atom marked * is D—.

The preferred stereochemistry at the carbon atom marked (+) is S.

The term 'aryl' includes phenyl and naphthyl, each optionally substituted with up to five, preferably up to three, groups selected from halogen, mercapto, $(C_{1-6})$alkyl optionally substituted by 1–3 halo, phenyl, phenyl$(C_{1-6})$alkyl, phenyl$(C_{1-6})$alkoxy, $(C_{1-6})$alkoxy optionally substituted by 1–3 halo, hydroxy$(C_{1-6})$alkyl, mercapto$(C_{1-6})$alkyl, hydroxy, $CO_2R_7$, $N(R_7)_2$ or $CON(R_7)_2$ where each $R_7$ is independently hydrogen, $(C_{1-6})$alkyl or $(C_{1-6})$ alkanoyl, $OCONH_2$, nitro, $(C_{1-6})$ alkylcarbonyloxy, $(C_{1-6})$ alkoxycarbonyl$(C_{1-6})$ alkyl, formyl and $(C_{1-6})$ alkylcarbonyl groups.

Each alicyclic ring suitably has from 4 to 7, preferably 5 or 6, ring carbon atoms.

Alicyclic rings may be unsubstituted or substituted by, for example, up to five, preferably up to three, groups selected from those mentioned above for substitution on aryl.

The terms 'heterocyclyl' and 'heterocyclic' as used herein include aromatic and non-aromatic, single and fused, rings suitably containing up to four hetero-atoms in each ring selected from oxygen, nitrogen and sulphur, which rings may be unsubstituted or substituted by, for example, up to three groups selected from those mentioned above for substitution on aryl and, for non-aromatic heterocyclic rings, oxo groups. Each heterocyclic ring suitably has from 4 to 7, preferably 5 or 6, ring atoms. The term 'heteroaryl' refers to heteroaromatic heterocyclic ring or ring system, suitably having 5 or 6 ring atoms in each ring. A fused heterocyclic ring system may include alicyclic rings and need include only one heterocyclic ring. Examples of heterocycl groups include pyridyl, triazolyl, tetrazolyl, indolyl, thienyl, isoimidazolyl, thiazolyl, furanyl, tetrahydrofuranyl, quinolinyl, imidazolidinyl and benzothienyl. Components within the invention containing a heterocyclyl group may occur in two or more tautometric forms depending on the nature of the heterocyclyl group; all such tautomeric forms are included within the scope of the invention.

When used herein the terms 'lower alkyl', 'lower alkenyl', 'lower alkynyl' and 'alkoxy' include straight and branched chain groups containing from 1 to 6 carbon atoms, such as methyl, ethyl, propyl and butyl. A particular alkyl group is methyl.

When used herein the term 'halogen' refers to fluorine, chlorine, bromine and iodine.

In a preferred aspect, when $R_1$ is formula (a), ring A is selected from 2,5-thienyl, 2,5-furyl, 1,2-phenyl, 1,3-phenyl and 1,4-phenyl, ring B is selected from phenyl optionally substituted by one or two hydroxy or by methoxy, dimethylamino, carboxy, nitro, amino, acetylamino, trifluoromethoxy or benzyloxy, 2-furyl, 2-, 3- or 4-pyridyl, 1-tetrazolyl, 2-tetrazolyl, 1-triazolyl, 2-triazolyl, 2 thienyl and imidazolin-2,5-dione-1-yl and C is selected from $CH_2$, O or $OCH_2$. In a more preferred aspect $R_1$ is 4-benzyloxyphenyl 3- or 4-substituted in the benzyl group by a substituent listed above for phenyl or naphthyl. Preferred substituents are carboxy and dimethylamino.

In another preferred aspect, when $R_1$ is formula (b), rings A and B are both phenyl, C is O, $CH_2$ or $NR_{10}$ and D is a bond (p+q=0).

Preferred examples of $R_1$ include (5-benzyl)thien-2-yl, (5-benzyl)furan-2-yl, 5-(1-tetrazolylmethyl)thien-2-yl, 5-(2-tetrazolylmethyl)thien-2-yl, 5-(imidazolin-2,5-dione-1-ylmethyl)thien-2-yl, 5-(1-triazolylmethyl)thien-2-yl, 5-(2-triazolylmethyl)thien-2-yl, 3-phenoxyphenyl, 2-phenoxyphenyl, 4-phenoxyphenyl, 4-phenoxyphenyl, 3-(4-hydroxybenzyl)phenyl, 3-(4-methoxybenzyl)phenyl, 4-benzyloxyphenyl, 4-(2-thienylmethyloxy)phenyl, 1-fluorenyl, 3-(N-ethylcarbazolyl), 4-hydroxybenzyloxy-4-phenyl, 4-methoxybenzyloxy-4-phenyl, 4-dimethylaminobenzyloxy-4-phenyl, 4-carboxybenzyloxy-4-phenyl, 3-carboxybenzyloxy-4-phenyl, (2-pyridyl)-methoxy-4-phenyl, (4-pyridyl)-methoxy-4-phenyl, 5-[1-(4-carbamoyltriazolyl)-methyl]-thien-2-yl, 5-[1-(4-carboxytriazolyl)-methyl]-thien-2-yl, (2-furyl)-methoxy-4-phenyl, dibenzofuranyl, 4-(4-acetamidobenzyloxy)phenyl, 3-(3-carboxybenzyloxy)phenyl, 3-(4-carboxybenzyloxy)phenyl, 4-(3-aminobenzyloxy)phenyl, 4-(4-dimethylaminobenzyloxy)phenyl, 4-(4-benzyloxybenzyloxy)phenyl and 4-(4-trifluoromethoxybenzyloxy)phenyl.

Suitable examples of $R_2$ include hydrogen, methyl and benzyl.

$R_2$ is preferably hydrogen.

Examples of $R_3$ include methyl, isobutyl, phenyl-$(CH_2)_{1-5}$, phenoxyethyl, 1-indanyl, 3,4-dihydroxybenzyl, 4-hydroxycarbonyl-phenylethyl, 2-trifluoromethylquinolin-6-yl, 4-difluoromethoxy-phenylethyl, 3-difluoromethoxy-phenylethyl and 3-methyl-2,4,5-tricarbonlimidazol-1-yl.

Preferably $R_3$ is aryl-$(CH_2)_m$-X-$(CH_2)_n$, such as benzyl, 2-phenethyl or 3-phenylpropyl wherein the aryl moiety is preferably unsubstituted or substituted by $(C_{1-6})$ alkoxy optionally substituted by 1–3 halo. When X is $S(O)_x$, x is preferably 0. $R_3$ is most preferably 2-phenethyl.

Examples of $R_4$ include hydrogen, lower alkylcarbonyl, optionally substituted benzoyl or optionally substituted phenyl lower alkyl carbonyl, more preferably hydrogen and acetyl.

$R_4$ is preferably hydrogen.

$R_5$ and $R_6$ are preferably independently hydrogen or methyl.

Suitable pharmaceutically acceptable salts of the carboxylic acid group of the compound of formula (I) (or of other carboxylic acid groups which may be present as optional substituents) include those in which R is a metal ion e.g., aluminium salts, alkali metal salts (e.g. sodium, lithium or potassium salts), alkaline earth metal salts (e.g. calcium or magnesium salts), ammonium salts, and substituted ammonium salts, for example those with lower alkylamines (e.g. triethylamine), hydroxy-lower alkylamines (e.g. 2-hydroxyethylamine), bis-(2-hydroxyethyl)amine, tris-(2-hydroxyethyl) amine, lower-cycloalkylamines (e.g. dicyclohexyl-amine), or with procaine, dibenzylamine, N,N-dibenzyl-ethylenediamine, 1-ephenamine, N-methylmorpholine, N-ethylpiperidine, N-benzyl-β-phenethylamine, dehydroabietylamine, ethylenediamine, N,N'-bishydroabietylethylenediamine, bases of the pyridine type (e.g. pyridine, collidine and quinoline), and other amines which have been or can be used to form quaternary ammonium salts.

Pharmaceutically acceptable salts may also be acid addition salts of any amino or substituted amino group(s) that may be present as optional substituents on the compound of formula (I), or of a heterocyclic group ring nitrogen atom. Suitable salts include for example hydrochlorides, sulphates, hydrogen sulphates, acetates, phosphates etc. and other pharmaceutically acceptable salts will be apparent to those skilled in the art. Suitable addition salts are the hydrochlorides and hydrogen sulphates.

Preferred salts are sodium salts.

Examples of suitable pharmaceutically acceptable in vivo hydrolysable ester-forming groups R include those forming esters which break down readily in the human body to leave the parent acid or its salt. Suitable groups of this type include those of part formulae (i), (ii), (iii), (iv) and (v):

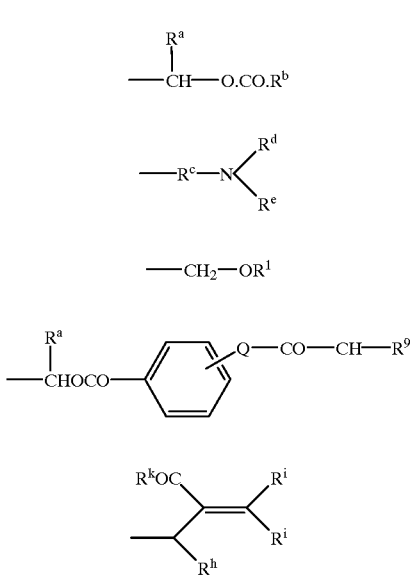

(i) —CH(R^a)—O.CO.R^b (ii) —R^c—N(R^d)(R^e)

(iii) —CH$_2$—OR$^1$ (iv) R^a substituted structure —CHOCO—[phenyl]—Q—CO—CH—R^g (v) R^kOC, R^i, R^i, R^h structure wherein $R^1$ is hydrogen, $(C_{1-6})$ alkyl, $(C_{3-7})$ cycloalkyl, methyl, or phenyl, $R^b$ is $(C_{1-6})$ alkyl, $(C_{1-6})$ alkoxy, phenyl, benzyl, $(C_{3-7})$ cycloalkyl, $(C_{3-7})$ cycloalkoxy, $(C_{1-6})$ alkyl $(C_{3-7})$ cycloalkyl, 1-amino $(C_{1-6})$ alkyl, or 1-$(C_{1-6}$ alkyl) amino $(C_{1-6})$ alkyl; or $R^a$ and $R^b$ together form a 1,2-phenylene group optionally substituted by one or two methoxy groups; $R^c$ represents $(C_{1-6})$ alkylene optionally substituted with a methyl or ethyl group and $R^d$ and $R^e$ independently represent $(C_{1-6})$ alkyl; $R^f$ represents $(C_{1-6})$ alkyl; $R^g$ represents hydrogen or phenyl optionally substituted by up to three groups selected from halogen, $(C_{1-6})$ alkyl, or $(C_{1-6})$ alkoxy; Q is oxygen or NH; $R^h$ is hydrogen or $(C_{1-6})$ alkyl; $R^1$ is hydrogen, $(C_{1-6})$ alkyl optionally substituted by halogen, $(C_{2-6})$ alkenyl, $(C_{1-6})$ alkoxycarbonyl, aryl or heteroaryl; or $R^h$ and $R^i$ together form $(C_{1-6})$ alylene; $R^j$ represents hydrogen, $(C_{1-6})$ alkyl or $(C_{1-6})$ alkoxycarbonyl; and $R^k$ represents $(C_{1-8})$ alkyl, $(C_{1-8})$ alkoxy, $(C_{1-6})$ alkoxy$(C_{1-6})$alkoxy or aryl.

Examples of suitable in vivo hydrolysable ester-forming groups include, for example, acyloxyalkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; alkoxycarbonyloxyalkyl groups, such as ethoxycarbonyloxymethyl, α-ethoxycarbonyloxyethyl and propoxycarbonyloxyethyl; dialkylaminoalkyl especially di-loweralkylamino alkyl groups such as dimethylaminomethyl, dimethylaminoethyl, diethylaminomethyl or diethylaminoethyl; 2-(alkoxycarbonyl)-2-alkenyl groups such as 2-(isobutoxycarbonyl)pent-2-enyl and 2-(ethoxycarbonyl)but-2-enyl; and lactone groups such as phthalidyl and dimethoxyphthalidyl.

A further suitable pharmaceutically acceptable in vivo hydrolysable ester-forming group is that of the formula:

[structure with CH$_2$, R^k, O, O, O ring]

wherein $R^k$ is hydrogen, $C_{1-6}$ alkyl or phenyl.

R is preferably hydrogen.

It will be appreciated that also included within the scope of the invention are pharmaceutically acceptable salts and pharmaceutically acceptable esters, including in vivo hydrolysable esters, of any carboxy groups that may be present as optional substituents in compounds of formula (I).

Some compounds of formula (I) may be crystallised or recrystallised from solvents such as organic solvents. In such cases solvates may be formed. This invention includes within its scope stoichiometric solvates including hydrates as well as compounds containing variable amounts of solvents such as water that may be produced by processes such as lyophilisation. Compounds of formula (I) may be prepared in crystalline form by for example dissolution of the compound in water, preferably in the minimum quantity thereof, followed by admixing of this aqueous solution with a water miscible organic solvent such as a lower aliphatic ketone such as a di-$(C_{1-6})$ alkyl ketone, or a $(C_{1-6})$ alcohol, such as acetone or ethanol.

The compounds of formula (I) are metallo-β-lactamase inhibitors and are intended for use in pharmaceutical compositions. Therefore it will readily be understood that they are preferably each provided in substantially pure form, for example at least 60% pure, more suitably at least 75% pure and preferably at least 85% pure, especially at least 95% pure particularly at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (I) or salt, solvate or in vivo hydrolysable ester thereof.

The present invention also provides a process for the preparation of a compound of formula (I) as defined above, which comprises reacting a compound of formula (II)

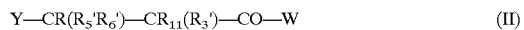

Y—CR($R_5'R_6'$)—CR$_{11}$($R_3'$)—CO—W   (II)

with a compound of formula (III)

X$^1$—CH($r_1'$)—CO$_2$R$^x$   (III)

wherein W is a leaving group, Y is Y' where Y' is $R_4$'S or a group convertible thereto and $R_{11}$ is H, or Y and $R_{11}$ together form a bond, $R^x$ is R or a carboxylate protecting group, $X^1$ is $N_3$ or NHR$_2'$ and $R_1'$, $R_2'$, $R_3'$, $R_4'$, $R_5'$ and $R_6'$ are $R_1$, $R_2$, $R_3$, $R_4$, $R_5$ and $R_6$ or groups convertible thereto, wherein R, $R_1$, $R_2$, $R_3$, $R_4$, $R_5$ and $R_6$ are as defined in formula (I), and thereafter, where Y and $R_{11}$ form a bond, reacting the product with a nucleophilic sulphur reagent Y'H, where necessary, converting Y' into $R_4$'S, $R^x$, $R_1'$, $R_2'$, $R_3'R_4'$, $R_5'$ and/or $R_6'$ into R, $R_1$, $R_2$, $R_3$, $R_4$, $R_5$ and/or $R_6$ and optionally inter-converting R, $R_1$, $R_2$, $R_3$, $R_4$, $R_5$ and/or $R_6$.

Suitable ester-forming carboxyl-protecting groups $R^x$ other than in vivo hydrolysable ester forming groups are those which may be removed under conventional conditions. Such groups for $R^x$ include methyl, ethyl, benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, a silyl (such as trimethylsilyl), stannyl or phosphorus-containing group or an oxime radical of formula —N═CHR$_{12}$ where R$_{12}$ is aryl or heterocyclyl, or an in vivo hydrolysable ester radical such as defined above.

Certain compounds of formula (II) and (III) may include an amino group which may be protected. Suitable amino protecting groups are those well known in the art which may be removed under conventional conditions if required without disruption of the remainder of the molecule.

Examples of amino protecting groups include (C$_{1-6}$) alkanoyl; benzoyl; benzyl optionally substituted in the phenyl ring by one or two substituents selected from (C$_{1-4}$) alkyl, (C$_{1-4}$) alkoxy, trifluorophenyl, halogen, or nitro; (C$_{1-4}$) alkoxycarbonyl; benzyloxycarbonyl or trityl substituted as for benzyl above; allyloxycarbonyl, trichloroethoxycarbonyl or chloroacetyl.

When $X^1$ is the compound of formula (III) is NHR$_2$', the compound is preferably presented as the anion prepared by treatment of the amine with an organic base such as triethylamine, pyridine or morpholine, and suitable examples of the leaving W group in the compound of formula (II) include halo such as chloro and mixed sulphonic anhydrides such as those where W is methanesulphonyloxy, toluene-p-sulphonyloxy or trifluoromethanesulphonyloxy in mixed sulphonic anhydrides. The compound of formula (III) may be presented as the trimethylsilyl ester hydrochloride.

The reaction of the compounds of formula (II) and (III) is preferably carried out at ambient temperature, for example 15–25° C., in an inert solvent such as chloroform, tetrahydrofuran, dichloromethane, dioxan or dimethylformamide.

When X in the compound of formula (III) is N$_3$, the leaving group W in the compound of formula (II) is preferably SH and the reaction is carried out at elevated temperature, such as at reflux, in an inert solvent such as toluene.

Examples of Y' convertible into R$_4$'S include halo such as bromo which may be displaced by thiobenzoic acid or thioacetic acid.

Where R$_{11}$ and Y together represent a bond, the group R$_4$'S may be introduced by addition of a nucleophilic sulphur reagent Y'H. Y' is R$_4$'S or a group convertible thereto. Thiolacetic acid is a suitable sulphur reagent.

Examples of groups R$_1$', R$_2$', R$_3$', R$_4$' convertible to R$_1$, R$_2$, R$_3$ and R$_4$ include those where any carboxy or amino group is protected by carboxy or amino protecting groups. Additionally, examples of R$_1$' convertible to R$_1$ include those containing ring A substituted by hydroxy which can generate R$_1$ groups of formula (a) where linker C is of the form —O—(CR$_8$R$_9$)$_q$— and where ring B is an aromatic ring or heterocycle, optionally substituted. This may be effected, for example, by alkylation of the hydroxy substituent with a benzyl bromide derivative or with a heterocyclylalkyl bromide derivative. Alternatively, the hydroxy group may be coupled with a benzyl alcohol derivative or with a heterocyclylalkyl alcohol derivative in established ways, for example in the presence of diethyl azodicarboxylate and triphenylphosphine (Mitsunobo et al, *Bull. Chem. Soc. Jpn.,* 1967, 40, 2380).

R$_4$' in the compound of formula (II) is preferably other than hydrogen, such as an acyl protecting group as described above for carboxy protecting groups, for example acetyl.

The acid derivative of formula (II) is preferably prepared from the corresponding free acid by treatment with strong base such as sodium hydride followed by a source of the anion leaving group W, such as oxalyl chloride where W is Cl, or hydrogen sulphide where W is SH.

The initial product of the reaction of compounds of formulae (II) and (III) is a compound of formula (IV):

wherein the variables are as defined in formulae (II) and (III). Novel intermediates of formula (IV) wherein $R^x$ is other than R when R$_1$', R$_2$', R$_3$', R$_4$', R$_5$' and R$_6$' are R$_1$, R$_2$, R$_3$, R$_4$, R$_5$ and R$_6$ also form part of the invention.

Compounds of formula (IV) where R$_1$' is —(A)—OH or —(A)—CH$_2$OH may be converted to compounds with R$_1$ as defined in (a) where C is —OCH$_2$— or —CH$_2$O— using alcohols of formula (B')—CH$_2$OH or (B')—OH, respectively under Mitsunobu conditions (Synthesis 1981, 1), using a coupling reagent such as triphenyl phosphine and diethyl azodicarboxylate. B' is B or a group convertible thereto, for example where a carboxy or amino substituent on B is protected.

When $R^x$ is other than hydrogen, the carboxy group —COOR$^x$ may be deprotected, that is to say, converted to a free carboxy, carboxy salt or carboxy ester group —COOR in a conventional manner, for example as described in EP023966A.

Simultaneous deprotection of —COOR$^x$ and R$_4$'S and any protecting group in R$_1$' may be achieved by treatment with sodium sulphide nonahydrate in water/methanol.

When it is desired to obtain a free acid or salt of the preferred isomer of the formula (I) from an isomeric mixture, this may be effected by chromatographic separation of the diastereomers of the product. Where this is an ester and/or where R$_4$' is other than hydrogen, the desired isomer may then be deprotected to give the corresponding free acid or salt. In some cases, however, it has been found particularly convenient first to deprotect the isomeric mixture to give an isomeric mixture of the free acid or salt of formula (I), followed by fractional recrystallisation to give the desired acid or salt isomer. When *D isomer of formula (I) is desired, it is preferred to use the corresponding *D isomer of the intermediate of formula (III).

When an enatiomerically pure form of (III) is used in the preparation of (I), the preferred diastereomer at position (+) of (I) can also be separated by chromatography. An enantiomerically pure form of (II) may also be used.

A carboxyl group may be regenerated from any of the above esters by usual methods appropriate to the particular $R^x$ group, for example, acid- and base-catalysed hydrolysis, or by enzymically-catalysed hydrolysis, or by hydrogenolysis under conditions wherein the remainder of the molecule is substantially unaffected. For example, in the case of acetonyl, by hydrolysis in acetonitrile with 0.1M aqueous potassium hydroxide solution.

Pharmaceutically acceptable salts may be prepared from such acids by treatment with a base, after a conventional work-up if necessary. Suitable bases include sodium hydrogen carbonate to form sodium salts.

Crystalline forms of the compounds of formula (I) where R is a salt forming cation may for example be prepared by dissolving the compound (I) in the minimum quantity of water, suitably at ambient temperature, then adding a water miscible organic solvent such as a ($C_{1-6}$) alcohol or ketone such as ethanol or acetone, upon which crystallisation occurs and which may be encouraged for example by cooling or trituration.

Compounds of formulae (II) and (III) are known compounds or may be prepared by procedures analogous to those described in the prior art references listed above.

$R_5'/R_6'$ substituted compounds of formula (II) where Y is Y' and $R_{11}$ is H may generally be prepared from an acrylic, crotonic, β-substituted acrylic, or β,β-disubstituted acrylic acid or ester of formula (V):

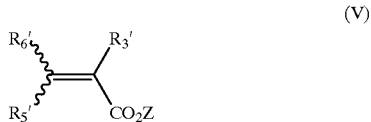

in which Z is H or a hydrolysable ester forming group and the remaining variables are as previously defined, by addition of a nucleophilic sulphur reagent Y'H. Y' is $R_4'S$ or a group convertible thereto.. Thiolacetic acid is a suitable sulphur reagent. Subsequent conversion of the carboxylate group $CO_2Z$ to a reactive acid group COW, provides the compound of structure (II).

Compounds of formula (II) where Y and $R_{11}$ are a bond may be obtained from compounds of formula (V) by conversion of the acid group to a leaving group COW.

Compounds of formula (V) are prepared conventionally.

Novel compounds of formula (III), which are α-amino acids, may be prepared by any conventional amino acid synthesis, for example from the corresponding α-keto ester $R_1'$—CO—$CO_2R^x$ via the oxime ester $R_1'$-C(=N—OH)—$CO_2R^x$ by conventional routes. The α-keto ester is obtainable from the $R_1'$—H, $R_1'$—$CH_2CO_2R^x$ or $R_1'$—$CO_2R^x$ by routine methods (J. March, vide infra). Alternatively the compounds of formula (III) may be prepared from the aldehyde intermediate $R_1'$—CHO by the Strecker synthesis [cf. Advanced Organic Chemistry; Mechanism and Structure, 4th Edn, by J. March, Section 6-50, p.965; 1992, John Wiley and Sons Inc, ISBN 0-471-60180-2] or by the method of Monianari et al. (Synthesis 1979, 26). The invention also extends to novel compounds of formula (III).

A compound of formula (I) or a salt, solvate or in vivo hydrolysable ester thereof, may be administered in the form of a pharmaceutical composition together with a pharmaceutically acceptable carrier and the invention also relates to such compositions. The compounds of formula (I) have metallo-β-lactamase inhibitory properties, and are useful for the treatment of infections in animals, especially mammals, including humans, in particular in humans and domesticated (including farm) animals. The compounds may be used, for example, for the treatment of infections of, inter alia, the respiratory tract, the urinary tract, and soft tissues and blood, especially in humans.

Accordingly, the invention further provides a method of treatment of bacterial infections in humans or animals which comprises administering, in combination with a β-lactam antibiotic, a therapeutically effective amount of a compound of formula (I) or a pharmaceutically acceptable salt, solvate or in vivo hydrolysable ester thereof.

The compounds may be used in combination with an antibiotic partner for the treatment of infections caused by metallo-β-lactamase producing strains, in addition to those infections which are subsumed within the antibacterial spectrum of the antibiotic partner. Metallo-β-lactamase producing strains include: *Pseudomonas aeruginosa, Klebsiella pneumoniae, Xanthomonas maltophilia, Bacteroides fragilis, Serratia marcescens, Bacteroides distasonis, Pseudomonas cepacia, Aeromonas hydrophilia, Aeromonas sobria, Aeromonas salmonicida, Bacillus cereus, Legionella gormanii* and Flavobacterium spp.

It is generally advantageous to use a compound according to the invention in admixture or conjunction with a carbapenem, penicillin, cephalosporin or other β-lactam antibiotic and that can result in a synergistic effect, because of the metallo-β-lactamase inhibitory properties of the compounds according to the invention. In such cases, the compound of formula (I) and the β-lactam antibiotic can be administered separately or in the form of a single composition containing both active ingredients as discussed in more detail below. The compositions of the invention include those in a form adapted for oral, topical or parenteral use and may be used for the treatment of bacterial infection in mammals including humans. The compounds of formula (I) are particularly suitable for parenteral administration.

The compounds of formula (I) may be formulated for administration in any convenient way for use in human or veterinary medicine, by analogy with other antibiotics and other β-lactam antibiotic/β-lactamase inhibitor combinations.

The composition may be formulated for administration by any route, such as oral, topical or parenteral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulations. More usually they will form up to about 80% of the formulations.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium laury sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I), (IA) or (IB) or a pharmaceutically acceptable salt thereof is administered in the above-mentioned dosage range.

A composition according to the invention may comprise a compound of formula (I) or a salt, solvate or in vivo hydrolysable ester thereof together with one or more additional active ingredients or therapeutic agents, for example a β-lactam antibiotic such as a carbapenem, penicillin or cephalosporin or pro-drug thereof. Carbapenems, penicillins, cephalosporins and other β-lactam antibiotics suitable for co-administration with the compound of formula (I)—whether by separate administration or by inclusion in the compositions according to the invention—include both those known to show instability to or to be otherwise susceptible to metallo-β-lactamases and also those known to have a degree of resistance to metallo-β-lactamases.

A serine β-lactamase inhibitor such as clavulanic acid, sulbactam or tazobactam may also be co-administered with the compound of the invention and the β-lactam antibiotic, either by separate administration, or co-formulation with one, other or both of the compounds of the invention and the β-lactam antibiotic.

Examples of carbapenems that may be co-administered with the compounds according to the invention include imipenem, meropenem, biapenem, BMS181139 ([4R-[4alpha,5beta,6beta(R*)]]-4-[2-[(aminoiminomethyl) amino]ethyl]-3-[(2-cyanoethyl)thio]-6-(1-hydroxyethyl)-7-oxo-1-azabicyclo[3.2.0]hept-2-ene-2-carboxylic acid), BO2727 ([4R-3[3S*,5S*(R*)],k4alpha,5beta,6beta(R*)]]-6-(1-hydroxyethyl)-3-[[5-[1-hydroxy-3-(methylamino) propyl]-3-pyrrolidinyl]thio]-4-methyl-7-oxo-1-azabicyclo [3.2.0] hept-2-ene-2-carboxylic acid monohydrochloride), ER35786 ((1R,5S,6S)-6-[1(R)-Hydroxymethyl]-2-[2(S)-[1 (R)-hydroxy-1-[pyrrolidin-3(R)-yl] methyl]pyrrolidin-4(S)-ylsulfanyl]-1-methyl-1-carba-2-penem-3-carboxylic acid hydrochloride), S4661 ((1R,5S,6S)-2[(3S,5S)-5-(sulfamoylaminomethyl) pyrrolidin-3-yl]thio-6-[(1R)-1-hydroxyethyl]-1-methylcarbapen-2-em-3-carboxylic acid), sanfetrinem and compounds described in WO95/11905 and WO96/34860 including sodium (5R,6S)-6-[(R)-1-hydroxyethyl]-2-(1-ethyl-5-methylpyrazol-3-yl)carbapen-2-em-3-carboxylate and in vivo hydrolysable esters described therein, preferably isobutyryloxymethyl (5R,6S)-2-[1-ethyl-5-methylpyrazol- 3-yl]-6[(1R)-1-hydroxyethyl]-carbapen-2-em-3-carboxylate, cyclohexyloxycarbonyloxymethyl (5R, 6S)-2-(1-ethyl-5-methylpyrazol-3-yl)-6-[(R)-1-hydroxyethyl]carbapen-2-em-3-carboxylate, (5-methyl-2-oxo-1,3-dioxolen-4-yl)methyl (5R, 6S)-2-[1-ethyl-5-methylpyrazol-3-yl]-6-[(1R)-1-hydroxyethyl]-carbapen-2-em-3-carboxylate or benzoyloxymethyl (5R,6S)-2-[1-ethyl-5-methylpyrazol-3-yl]-6-[(1R)-1-hydroxyethyl]-carbapen-2-em-3-carboxylate.

Examples of penicillins suitable for co-administration with the compounds according to the invention include benzylpenicillin, phenoxymethylpenicillin, carbenicillin, azidocillin, propicillin, ampicillin, amoxycillin, epicillin, ticarcillin, cyclacillin, pirbenicillin, azlocillin, mezlocillin, sulbenicillin, piperacillin, and other known penicillins. The penicillins may be used in the form of pro-drugs thereof, for example as in vivo hydrolysable esters, for example the acetoxymethyl, pivaloyloxymethyl, α-ethoxycarbonyloxyethyl and phthalidyl esters of ampicillin, benzylpenicillin and amoxycillin; as aldehyde or ketone adducts of penicillins containing a 6-α-aminoacetamido side chain (for example hetacillin, metampicillin and analogous derivatives of amoxycillin); and as α-esters of carbenicillin and ticarcillin, for example the phenyl and indanyl α-esters.

Examples of cephalosporins that may be co-administered with the compounds according to the invention include, cefatrizine, cephaloridine, cephalothin, cefazolin, cephalexin, cephacetrile, cephapirin, cephamandole nafate, cephradine, 4-hydroxycephalexin, cephaloglycin, cefoperazone, cefsulodin, ceftazidime, cefuroxime, cefmetazole, cefotaxime, ceftriaxone, and other known cephalosporins, all of which may be used in the form of pro-drugs thereof.

Examples of β-lactam antibiotics other than penicillins and cephalosporins that may be co-administered with the compounds according to the invention include aztreonam, latamoxef (Moxalactam—Trade Mark), and other known β-lactam antibiotics, all of which may be used in the form of pro-drugs thereof.

Particularly suitable penicillins for co-administration with the compounds according to the invention include ampicillin, amoxycillin, carbenicillin, piperacillin, azlocillin, mezlocillin, and ticarcillin. Such penicillins may be used in the form of their pharmaceutically acceptable salts, for example their sodium salts. Alternatively, ampicillin or amoxycillin may be used in the form of fine particles of the zwitterionic form (generally as ampicillin trihydrate or amoxycillin trihydrate) for use in an injectable or infusable suspension, for example, in the manner hereinbefore described in relation to the compounds according to the invention. Amoxycillin, for example in the form of its sodium salt or the trihydrate, is particularly preferred for use in synergistic compositions according to the invention.

Particularly suitable cephalosporins for co-administration with the compounds according to the invention include cefotaxime and ceftazidime, which may be used in the form of their pharmaceutically acceptable salts, for example their sodium salts.

A compound of formula (I) may be administered to the patient in conjunction with a β-lactam antibiotic such as a carbapenem, penicillin or cephalosporin in a synergistically effective amount.

The compounds of formula (I) may suitably be administered to the patient at a daily dosage of from 0.7 to 50 mg/kg of body weight. For an adult human (of approximately 70 kg body weight), from 50 to 3000 mg, preferably from 100 to 1000 mg, of a compound according to the invention may be administered daily, suitably in from 1 to 6, preferably from 2 to 4, separate doses. Higher or lower dosages may, however, be used in accordance with clinical practice.

When the compositions according to the invention are presented in unit dosage form, each unit dose may suitably comprise from 25 to 1000 mg, preferably from 50 to 500 mg, of a compound according to the invention. Each unit dose may, for example, be 62.5, 100, 125, 150, 200 or 250 mg of a compound according to the invention.

When the compounds of formula (I) are co-administered with a penicillin, cephalosporin, carbapenem or other β-lactam antibiotic, the ratio of the amount of the compound according to the invention to the amount of the other β-lactam antibiotic may vary within a wide range. The said ratio may, for example, be from 100:1 to 1:100; more particularly, it may, for example, be from 2:1 to 1:30.

The amount of carbapenem, penicillin, cephalosporin or other β-lactam antibiotic in a synergistic composition according to the invention will normally be approximately similar to the amount in which it is conventionally used per se, for example from about 50 mg, advantageously from about 62.5 mg, to about 3000 mg per unit dose, more usually about 125, 250, 500 or 1000 mg per unit dose.

The present invention further provides a compound of formula (I) or a pharmaceutically acceptable salt, solvate or in vivo hydrolysable ester thereof for use in the treatment of bacterial infections.

The present invention also includes the use of a compound of formula (I) or a pharmaceutically acceptable salt, solvate or in vivo hydrolysable ester thereof, in the manufacture of a medicament for the treatment of bacterial infections The present invention also includes the use of a compound of formula (I) or a pharmaceutically acceptable salt, solvate or in vivo hydrolysable ester thereof as a metallo-β-lactamase inhibitor.

All the above compositions and methods may optionally include a serine β-lactamase inhibitor as above described.

The compounds of the present invention are active against metallo-β-lactamase enzymes produced by a wide range of organisms including both Gram-negative organisms and Gram-positive organisms.

The following Examples illustrate compounds useful in the present invention, and intermediates in their preparation. (All temperatures are in °C.).

EXAMPLES

Description 1

2-(m-Bromophenyl)-1,3-dioxolane

To a stirred solution of 3-bromobenzaldehyde (5.00 g, 27.0 mmol) in toluene (35 ml) was added ethylene glycol (4.52 ml, 81.1 mmol) and p-toluenesulphonic acid (0.5 g). The mixture was heated to reflux for 2 hours, cooled, and washed with water and saturated sodium hydrogen carbonate solution. The organic layer was dried over MgSO4. The solvent was removed under reduced pressure to give the desired product as a colourless oil (6.22 g, 100%). $\delta_H$ (CDCl$_3$) 4.09 (4H, m), 5.79 (1H, s), 7.2–7.7 (4H) ppm.

Description 2 m-(1,3-Dioxolan-2-yl)-benzhydrol

A stirred solution of the acetal (1.0 g, 4.37 mmol) of Description 1 in dry tetrahydrofuran (50 ml), under argon, was cooled to −80° and treated with a 1.6 M solution of n-butyllithium in hexane (2.73 ml, 4.37 mmol). The resulting yellow solution was stirred at −80° for 0.5 hours. A solution of redistilled benzaldehyde (0.44 ml, 4.37 mmol) in dry tetrahydrofuran (5 ml) was added over 2 minutes and the solution left to stir for 1 hour. The reaction mixture was warmed to room temperature over the next hour and then diluted with ethyl acetate and washed with water. The organic layer was dried (MgSO4) and evaporated to afford an oil which was chromatographed on silica gel. Elution with ethyl acetate/hexane (1:2) gave the desired product as a colourless oil (0.57 g, 51%). $\delta_H$ (CDCl$_3$) 2.23 (1H, d, J 3.5 Hz), 4.1 (4H, m), 5.80 (1H, s), 5.87 (1H, d, J 3.5 Hz), 7.2–7.6 (9H) ppm. EIMS M$^+$ 256.

Description 3 m-Benzyl-benzaldehyde

To a stirred, cooled (0°), solution of the alcohol (1.0 g, 3.91 mmol) from Description 2 in acetonitrile (10 ml), under argon, was added sodium iodide (2.30 g, 15.3 mmol). The resulting suspension was treated with dichlorodimethylsilane (0.93 ml, 7.64 mmol) and allowed to remain at 0° for 5 minutes before warming to room temperature. After a further 15 minutes the mixture was diluted with ethyl acetate and washed with water and saturated sodium hydrogen carbonate solution followed by 10% sodium thiosulphate solution. The colourless organic layer was dried and evaporated to yield a brown oil which was chromatographed on silica gel. Elution with 10% ethyl acetate in hexane gave the desired product as a pale oil (0.63 g, 82%). $\delta_H$ (CDCl$_3$) 4.07 (2H, s), 7.2–7.7 (9H, m), 9.99 (1H, s) ppm. EIMS M+196.

Description 4 m-Benzyl-phenylglycine Methyl Ester

The aldehyde (0.42 g, 2.14 mmol) from Description 3 was converted to the crude amino acid using essentially the method of Monianari et al. (Synthesis 1979, 26), but with some changes to the final purification. The crude solid material obtained after neutralization and evaporation of the water was stirred in methanol (10 ml), presaturated with hydrogen chloride gas, overnight. The methanol was removed under reduced pressure and the residue partitioned between ethyl acetate and an excess of saturated NaHCO3 solution. The organic layer was washed with water and dried. Removal of the solvent afforded the crude product as a pale oil (56 mg, 10% over 2 stages).

Description 5

N-(2'-acetylthiomethyl-4'-phenylbutanoyl)-m-benzyl-phenylglycine Methyl Ester

A mixture of 2-phenylethylmalonic acid (1.8 g), 40% aqueous dimethylamine (1.08 ml, 1 eq) and 37% aqueous formaldehyde (0.64 ml, 1 eq) in water (10 ml) was stirred at room temperature overnight. After cooling at 0° C. the solid was filtered off, washed with water and dried. The white solid was heated at 170° C. for 10 minutes and cooled to room temperature. The resulting gum was dissolved in ethyl acetate (20 ml), washed with 10% potassium hydrogen sulphate solution (10 ml), water (2×10 ml), saturated brine (10 ml), dried (MgSO$_4$) and evaporated to give crude 2-methylene-4-phenylbutanoic acid. $\delta_H$ (CDCl$_3$) 2.55–2.90 (4H, m, 2×CH$_2$), 5.65, 6.85 (2H, 2×s, =$_H$), 7.25 (5H, m, Ph).

The solid was dissolved in thioacetic acid (1 ml) and heated at 100° C. for 1 hour. After evaporation the gum was dissolved in ethyl acetate (10 ml) and extracted with saturated sodium hydrogen carbonate solution (2×10 ml). The combined extracts were washed with ethyl acetate (2×10 ml) and acidified with 10% potassium hydrogen sulphate solution (pH 3). The aqueous layer was extracted with ethyl acetate (2×10 ml) and the combined extracts washed with water (2×10 ml), dried (MgSO$_4$) and evaporated to yield 2-acetylthiomethyl-4-phenylbutanoic acid as a yellow oil (0.52 g, 24%); $\delta_H$ (CDCl$_3$) 2.00 (2H, m, CH$_2$), 2.71 (3H, m, CH$_2$, CH), 3.14 (2H, m, CH$_2$), 7.24 (5H, m, Ph). EIMS M$^+$ 252 DCIMS MNH$_4^+$ 270.

To a cooled (0°), stirred solution of 2-acetylthiomethyl-4-phenylbutanoic acid (68 mg, 0.27 mmol) in dry tetrahydrofuran (5 ml) containing dry dimethylformamide (1 drop), was added sodium hydride (12 mg of a 55% suspension in oil, 0.27 mmol). The reaction mixture was allowed to reach room temperature and stirring was continued for a further 15 mins. The suspension was then recooled (0°) and treated with oxalyl chloride (28 ul, 0.32 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) solution of m-benzyl-phenylglycine methyl ester (Description 4, 56 mg, 0.22 mmol) in dry tetrahydrofuran (5 ml) was treated with triethylamine (42 ul, 0.3 mmol) followed by a solution of the above acid chloride in dry tetrahydrofuran (3 ml) added over 1 minute. The mixture was stirred at ambient temperature for 3 hours and then partitioned between ethyl acetate and 1 M hydrochloric acid. The organic layer was washed with water and saturated brine and dried over anhydrous sodium sulphate. Evaporation of the solvent afforded crude product as an oil which was chromatographed on silica gel. Elution with 20% ethyl acetate in hexane afforded diastereoisomer A as an oil (28 mg, 26%). $\delta_H$ (CDCl$_3$) 1.90 (1H, m), 2.02 (1H, m), 2.24 (3H, s), 2.27 (1H, m), 2.66 (2H, m), 3.00 (2H, m), 3.73 (3H, s), 3.99 (2H, s), 5.53 (1H, d, J 7.0 Hz), 6.41 (1H, d, J 7.0 Hz), 7.2 (14H, m) ppm. ESMS MH$^+$ 490. This was followed by diastereoisomer B as an oil (26 mg, 24%). $\delta_H$ (CDCl$_3$) 1.90 (2H, m), 2.33 (3H, s), 2.40 (3H, m), 3.06 (2H, m), 3.73 (3H, s), 3.98 (2H, s), 5.59 (1H, d, J 7.2 Hz), 6.57 (1H, d, J 7.2 Hz), 7.1–7.3 (14H, m) ppm. ESMS MH$^+$ 490.

Description 6 m-Phenoxy-phenylglycine Methyl Ester m-Phenoxybenzaldehyde (3.45 ml, 0.02 mol) was converted to the crude amino acid using essentially the method of Monianari et al. (Synthesis 1979, 26), but with some changes to the final purification. The crude solid material obtained after neutralization and evaporation of the water was stirred in methanol (50 ml), presaturated with hydrogen chloride gas, overnight. The methanol was removed under reduced pressure and the residue partitioned between ethyl acetate and an excess of saturated NaHCO3 solution. The organic layer was washed with water and dried. Removal of the solvent afforded the crude product as a pale oil (0.48 g, 9% over 2 stages). $\delta_H$ (CDCl$_3$) 1.78 (2H, br s), 3.71 (3H, s), 4.59 (1H, s), 6.9–7.4 (9H, m) ppm.

Description 7

N-(2'-acetylthiomethyl-4'-phenylbutanoyl)-m-phenoxy-phenylglycine Methyl Ester

To a cooled (0°), stirred solution of 2-acetylthiomethyl-4-phenylbutanoic acid, prepared as in Description 5, (252 mg, 1.0 mmol) in dry tetrahydrofuran (5 ml) containing dry dimethylformamide (1 drop), was added sodium hydride (44 mg of a 55% suspension in oil, 1.0 mmol). The reaction mixture was allowed to reach room temperature and stirring was continued for a further 15 mins. The suspension was then recooled (0°) and treated with oxalyl chloride (105 ul, 1.20 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) solution of m-phenoxy-phenylglycine methyl ester (Description 6, 257 mg, 1.0 mmol) in dry tetrahydrofuran (5 ml) was treated with triethylamine (140 ul, 1.0 mmol) followed by a solution of the above acid chloride in dry tetrahydrofuran (5 ml) added over 1 minute. The mixture was stirred at ambient temperature for 3 hour and then partitioned between ethyl acetate and 1 M hydrochloric acid. The organic layer was washed with water and saturated brine and dried over anhydrous sodium sulphate. Evaporation of the solvent afforded crude product as an oil which was chromatographed on silica gel. Elution with 20% ethyl acetate in hexane afforded diastereoisomer A as an oil (151 mg, 31%). $\delta_H$ (CDCl$_3$) 1.89 (1H, m), 2.02 (1H, m), 2.26 (3H, s), 2.35 (1H, m), 2.68 (2H, m), 3.01 (2H, d, J 7.0 Hz), 3.76 (3H, s), 5.54 (1H, d, J 7.0 Hz), 6.48 (1H, d, J 7.0 Hz), 7.0–7.3 (14H, m) ppm. ESMS MH$^+$ 492. This was followed by diastereoisomer B as an oil (175 mg, 36%). $\delta_H$ (CDCl$_3$) 1.90 (2H, m), 2.33 (3H, s), 2.50 (3H, m), 3.06 (2H, m), 3.75 (3H, s), 5.58 (1H, d, J 7.0 Hz), 6.60 (1H, d, J 7.0 Hz), 7.0–7.3 (14H, m) ppm. ESMS MH$^+$ 492.

Description 8 m-(1,3-Dioxolan-2-yl)-p'-methoxybenzhydrol

A stirred solution of the acetal (3.17 g, 13.8 mmol) of Description 1 in dry tetrahydrofuran (60 ml), under argon, was cooled to −80° and treated with a 1.6 M solution of n-butyllithium in hexane (8.65 ml, 13.8 mmol). The resulting yellow solution was stirred at −80° for 0.5 hours. A solution of p-methoxybenzaldehyde (1.68 ml, 13.8 mmol) in dry tetrahydofuran (10 ml) was added over 2 minutes and the solution left to stir for 1 hour. The reaction mixture was warmed to room temperature over the next hour and then diluted with ethyl acetate and washed with water. The organic layer was dried (MgSO4) and evaporated to afford an oil which was chromatographed on silica gel. Elution with ethyl acetate/hexane (1:2) gave the desired product as a colourless oil (1.46 g, 38%). $\delta_H$ (CDCl$_3$) 2.17 (1H, d, J 3.5 Hz), 3.79 (3H, s), 4.07 (4H, m), 5.79 (1H, s), 5.82 (1H, d, J 3.5 Hz), 6.86 (2H, d, J 8.8 Hz), 7.2–7.5 (6H) ppm.

Description 9 m-(p-Methoxybenzyl)-benzaldehyde

To a stirred, cooled (0°), solution of the alcohol (1.48 g, 5.17 mmol) from Description 8 in acetonitrile (15 ml), under argon, was added sodium iodide (3.10 g, 20.7 mmol). The resulting suspension was treated with dichlorodimethylsilane (1.25 ml, 10.34 mmol) and allowed to remain at 0° for 5 minutes before warming to room temperature. After a further 15 minutes the mixture was diluted with ethyl acetate and washed with water and saturated sodium hydrogen carbonate solution followed by 10% sodium thiosulphate solution. The colourless organic layer was dried and evaporated to yield a brown oil which was chromatographed on silica gel. Elution with 10% ethyl acetate in hexane gave the desired product as a pale oil (0.90 g). $\delta_H$ (CDCl$_3$) 3.79 (3H, s), 4.00 (2H, s), 6.85 (2H, d, J 8.6 Hz), 7.11 (2H, d, J 8.6 Hz), 7.45 (2H, m), 7.72 (2H, m), 9.98 (1H, s) ppm. ESMS M$^+$ 226.

Description 10 m-(p-Methoxybenzyl)-phenylglycine Methyl Ester

The aldehyde (0.88 g, 3.89 mmol) from Description 9 was converted to the crude amino acid using essentially the method of Monianari et al. (Synthesis 1979, 26), but with some changes to the final purification. The crude solid material obtained after neutralization and evaporation of the water was stirred in methanol (50 ml), presaturated with hydrogen chloride gas, overnight. The methanol was removed under reduced pressure and the residue partitioned between ethyl acetate and an excess of saturated NaHCO3 solution. The organic layer was washed with water and dried. Removal of the solvent afforded the crude product as a pale oil which was chromatographed on silica gel. Elution with ethyl acetate gave the desired product as an oil (122 mg, 12% over 2 stages). $\delta_H$ (CDCl$_3$) 1.72 (2H, br s), 3.69 (3H, s), 3.79 (3H, s), 3.92 (2H, s), 4.58 (1H, s), 6.83 (2H, d, J 8.6 Hz), 7.10 (2H, d, J 8.6 Hz), 7.25 (4H, m) ppm.

Description 11

N-(2'-acetylthiomethyl-4'-phenylbutanoyl)-m-(p-methoxybenzyl)-phenylglycine Methyl Ester To a cooled (0°), stirred solution of 2-acetylthiomethyl-4-phenylbutanoic acid prepared as in Description 5, (108 mg, 0.43 mmol) in dry tetrahydrofuran (5 ml) containing dry dimethylformamide (1 drop), was added sodium hydride (19 mg of a 55% suspension in oil, 0.43 mmol). The reaction mixture was allowed to reach room temperature and stirring was continued for a further 15 mins. The suspension was then recooled (0°) and treated with oxalyl chloride (45 ul, 0.52 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) solution of m-(p-methoxybenzyl)-phenylglycine methyl ester (Description 10, 122 mg, 0.43 mmol) in dry tetrahydrofuran (5 ml) was treated with triethylamine (60 ul, 0.43 mmol) followed by a solution of the above acid chloride in dry tetrahydrofuran (3 ml) added over 1 minute. The mixture was stirred at ambient temperature for 3 hours and then partitioned between ethyl acetate and 1 M hydrochloric acid. The organic layer was washed with water and saturated brine and dried over anhydrous sodium sulphate. Evaporation of the solvent afforded crude product as an oil which was chromatographed on silica gel. Elution with 20% ethyl acetate in hexane afforded diastereoisomer A as an oil (71 mg, 32%). $\delta_H$ (CDCl$_3$) 1.90 (1H, m), 2.02 (1H, m), 2.24 (3H, s), 2.30 (1H, m), 2.72 (2H, m), 2.99 (2H, d, J 6.1 Hz), 3.74 (3H, s), 3.78 (3H, s), 3.93 (2H, s) 5.52 (1H, d, J 7.0 Hz), 6.41 (1H, d, J 7.0 Hz), 6.82 (2H, d, J 8.6 Hz), 7.09 (2H, d, J 8.6 Hz), 7.3 (9H, m) ppm. EIMS M$^+$ 519. This was followed by diastereoisomer B as an oil (67 mg, 30%). $\delta_H$ (CDCl$_3$) 1.90 (2H, m), 2.33 (3H, s), 2.50 (3H, m), 3.05 (2H, m), 3.73 (3H, s), 3.74 (3H, s) 3.98 (2H, s), 5.58 (1H, d, J 7.2 Hz), 6.55 (1H, d, J 7.2 Hz), 6.77 (2H, d, J 8.6 Hz), 7.0–7.3 (11H, m) ppm. EIMS M$^+$ 519.

Description 12 m-Benzyloxy-phenylglycine Methyl Ester m-Benzyloxybenzaldehyde (4.24 g, 0.02 mmol) was converted to the crude amino acid using essentially the method of Monianari et al. (Synthesis 1979, 26), but with some changes to the final purification. The crude solid material obtained after neutralization and evaporation of the water was stirred in methanol (50 ml), presaturated with hydrogen chloride gas, overnight. The methanol was removed under reduced pressure and the residue partitioned between ethyl acetate and an excess of saturated NaHCO3 solution. The organic layer was washed with water and dried. Removal of the solvent afforded the crude product as a pale oil which was purified by chromatography on silica gel. Elution with ethyl acetate gave the desired product as an oil (100 mg, 2% over 2 stages). $\delta_H$ (CDCl$_3$) 1.70 (2H, br s), 3.70 (3H, s), 4.59 (1H, s), 5.07 (2H, s), 6.9–7.1 (3H, m), 7.2–7.4 (6H, d, J 8.6 Hz), ppm.

Description 13

N-(2'-acetylthiomethyl-4'-phenylbutanoyl)-m-benzyloxy-phenylglycine Methyl Ester To a cooled (0°), stirred solution of 2-acetylthiomethyl-4-phenylbutanoic acid prepared as in Description 5, (93 mg, 0.37 mmol) in dry tetrahydrofuran (5 ml) containing dry dimethylformamide (1 drop), was added sodium hydride (17 mg of a 55% suspension in oil, 0.37 mmol). The reaction mixture was allowed to reach room temperature and stirring was continued for a further 15 mins. The suspension was then recooled (0°) and treated with oxalyl chloride (40 ul, 0.44 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) solution of m-benzyloxy-phenylglycine methyl ester (Description 12, 100 mg, 0.37 mmol) in dry tetrahydrofuran (5 ml) was treated with triethylamine (52 ul, 0.37 mmol) followed by a solution of the above acid chloride in dry tetrahydrofuran (3 ml) added over 1 minute. The mixture was stirred at ambient temperature for 3 hours and then partitioned between ethyl acetate and 1 M hydrochloric acid. The organic layer was washed with water and saturated brine and dried over anhydrous sodium sulphate. Evaporation of the solvent afforded crude product as an oil which was chromatographed on silica gel. Elution with 20% ethyl acetate in hexane afforded a mixture of diastereoisomers as an oil (101 mg, 54%). $\delta_H$ (CDCl$_3$) 1.90 (2H, m), 2.26 and 2.34 (3H, s), 2.4–3.1 (5H, m), 3.74 (3H, s), 5.05 and 5.08 (2H, s), 5.54 and 5.58 (1H, d, J 7.0 Hz), 6.44 and 6.59 (1H, d, J 7.0 Hz), 7.0–7.4 (14H, m) ppm.

Description 14 m-(1,3-Dioxolan-2-yl)-p'-benzyloxybenzhydrol

A stirred solution of the acetal (5.00 g, 21.8 mmol) of Description 1 in dry tetrahydrofuran (80 ml), under argon, was cooled to −80° and treated with a 1.5 M solution of n-butyllithium in hexane (14.6 ml, 21.8 mmol). The resulting yellow solution was stirred at −80° for 0.5 hours. A solution of p-benzyloxybenzaldehyde (4.63 g, 21.8 mmol) in dry tetrahydofuran (10 ml) was added over 2 minutes and the solution left to stir for 1 hour. The reaction mixture was warmed to room temperature over the next hour and then diluted with ethyl acetate and washed with water. The organic layer was dried (MgSO4) and evaporated to afford an oil which was chromatographed on silica gel. Elution with ethyl acetate/hexane (1:2) gave the desired product as a colourless oil (3.50 g, 44%). $\delta_H$ (CDCl$_3$) 2.19 (1H, d, J 3.5 Hz), 4.07 (4H, m), 5.05 (2H, s), 5.79 (1H, s), 5.82 (1H, d, J 3.5 Hz), 6.94 (2H, d, J 8.7 Hz), 7.2–7.5 (11H) ppm.

Description 15 m-(p-Benzyloxybenzyl)-benzaldehyde

To a stirred, cooled (0°), solution of the alcohol (3.49 g, 9.64 mmol) from Description 14 in acetonitrile (70 ml), under argon, was added sodium iodide (5.79 g, 38.6 mmol). The resulting suspension was treated with dichlorodimethylsilane (2.34 ml, 19.3 mmol) and allowed to remain at 0° for 5 minutes before warming to room temperature. After a further 15 minutes the mixture was diluted with ethyl acetate and washed with water and saturated sodium hydrogen carbonate solution followed by 10% sodium thiosulphate solution. The colourless organic layer was dried and evaporated to yield a brown oil which was chromatographed on silica gel. Elution with 10% ethyl acetate in hexane gave the desired product as a pale oil (2.19 g, 75%). $\delta_H$ (CDCl$_3$) 4.00 (2H, s), 5.04 (2H, s), 6.94 (2H, d, J 8.6 Hz), 7.11 (2H, d, J 8.5 Hz), 7.3–7.5 (7H, m), 7.70 (2H, m), 9.98 (1H, s) ppm.

Description 16 m-(p-Hydroxybenzyl)-phenylglycine Methyl Ester

The aldehyde (2.19 g, 7.25 mmol) from Description 15 was converted to the crude amino acid using essentially the method of Monianari et al. (Synthesis 1979, 26), but with some changes to the final purification. The crude solid material obtained after neutralization and evaporation of the water was stirred in methanol (50 ml), presaturated with hydrogen chloride gas, overnight. The methanol was removed under reduced pressure and the residue partitioned between ethyl acetate and an excess of saturated NaHCO3 solution. The organic layer was washed with water and dried. Removal of the solvent afforded the crude product as a pale oil which was chromatographed on silica gel. Elution with ethyl acetate gave the desired product as a white solid (44 mg). $\delta_H$ (CD$_3$OD) 3.67 (3H, s), 3.88 (2H, s), 4.52 (1H, s), 6.70 (2H, d, J 8.4 Hz), 7.01 (2H, d, J 8.5 Hz), 7.1–7.3 (4H, m) ppm. ESMS MH$^+$ 271.

Description 17

N-(2'-acetylthiomethyl-4'-phenylbutanoyl)-m-(p-hydroxybenzyl)-phenylglycine Methyl Ester To a cooled (0°), stirred solution of 2-acetylthiomethyl-4-phenylbutanoic acid prepared as in Description 5, (41 mg, 0.16 mmol) in dry tetrahydrofuran (5 ml) containing dry dimethylformamide (1 drop), was added sodium hydride (7 mg of a 55% suspension in oil, 0.16 mmol). The reaction mixture was allowed to reach room temperature and stirring was continued for a further 15 mins. The suspension was then recooled (0°) and treated with oxalyl chloride (17 ul, 0.19 mmol) and stirred at room ambient temperature or 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) solution of m-(p-hydroxybenzyl)-phenylglycine methyl ester (Description 16, 44 mg, 0.16 mmol) in dry tetrahydrofuran (5 ml) was treated with triethylamine (22 ul, 0.16 mmol) followed by a solution of the above acid chloride in dry tetrahydrofuran (3 ml) added over 1 minute. The mixture was stirred at ambient temperature for 3 hours and then partitioned between ethyl acetate and 1 M hydrochloric acid. The organic layer was washed with water and saturated brine and dried over anhydrous sodium sulphate. Evaporation of the solvent afforded crude product as an oil which was chromatographed on silica gel. Elution with 50% ethyl acetate in hexane afforded a mixture of diastereoisomers as an oil (52 mg, 64%). $\delta_H$ (CDCl$_3$) 1.85–2.00 (2H, m), 2.25 and 2.33 (3H, s), 2.3–2.8 (3H, m), 3.04 (2H, m), 3.74 (3H, s), 3.89 and 3.91 (2H, s), 5.01 and 5.12 (1H, s), 5.53 and 5.58 (1H, d, J 7.0 Hz), 6.61 and 6.47 (1H, d, J 7.0 Hz), 6.73 and 6.66 (2H, d, J 8.6 Hz), 7.0–7.3 (11H, m) ppm.

Description 18

1-Fluorenylmethanol

To a cooled (0°), stirred, solution of 1-fluorenecarboxylic acid (2.10 g, 10.0 mmol) in dry tetrahydrofuran (20 ml) under argon was added lithium aluminium hydride (0.19 g, 5 mmol) added in portions over 10 minutes. After a further 1 hour, water was added cautiously until effervescence ceased. The reaction mixture was partitioned between ethyl acetate and water and filtered. The organic layer was washed with saturated sodium hydrogen carbonate solution followed by water and dried over MgSO$_4$. Evaporation of solvent gave crude product. $\delta_H$ (CDCl3 containing CD$_3$OD) 3.87 (2H, s), 4.81 (2H, s), 7.2–7.75 (7H, m) ppm Description 19

1-Fluorenecarboxaldehyde

A solution of the crude alcohol from Description 18 in chloroform (130 ml) was treated with activated manganese dioxide (2 g) and stirred, under argon, for 10 days. The mixture was filtered through celite and the solvent removed to afford the desired product as a pale oil (0.73 g, 38%). $\delta_H$ (CDCl3) 4.29 (2H, s), 7.41 (2H, m), 7.61 (2H, m), 7.82 (2H, m), 8.06 (1H, d, J 7.3 Hz) 10.28 (1H, s) ppm.

Description 20

(1-Fluorenyl)glycine Methyl Ester

The aldehyde (0.73 g, 3.76 mmol) from Description 19 was converted to the crude amino acid using essentially the method of Monianari et al. (Synthesis 1979, 26), but with some changes to the final purification. The crude solid material obtained after neutralization and evaporation of the water was stirred in methanol (50 ml), presaturated with hydrogen chloride gas, overnight. The methanol was removed under reduced pressure and the residue partitioned between ethyl acetate and an excess of saturated NaHCO3 solution. The organic layer was washed with water and dried. Removal of the solvent afforded the crude product as a pale oil which was chromatographed on silica gel. Elution with ethyl acetate gave the desired product as a white solid (88 mg, 9% over 2 stages). $\delta_H$ (CDCl$_3$) 1.80 (2H, br s), 3.70 (3H, s), 3.93 and 4.08 (2H, AB, J 21.7 Hz), 4.90 (1H, s), 7.3–7.8 (7H, m) ppm.

Description 21

N-(2'-acetylthiomethyl-4'-phenylbutanoyl)-(1-fluorenyl)glycine Methyl Ester

To a cooled (0°), stirred solution of 2-acetylthiomethyl-4-phenylbutanoic acid prepared as in Description 5, (88 mg, 0.35 mmol) in dry tetrahydrofuran (5 ml) containing dry dimethylformamide (1 drop), was added sodium hydride (15 mg of a 55% suspension in oil, 0.35 mmol). The reaction mixture was allowed to reach room temperature and stirring was continued for a further 15 mins. The suspension was then recooled (0°) and treated with oxalyl chloride (37 ul, 0.42 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) solution of (1-fluorenyl)glycine methyl ester (Description 20, 88 mg, 0.35 mmol) in dry tetrahydrofuran (5 ml) was treated with triethylamine (49 ul, 0.35 mmol) followed by a solution of the above acid chloride in dry tetrahydrofuran (3 ml) added over 1 minute. The mixture was stirred at ambient temperature for 3 hours and then partitioned between ethyl acetate and 1 M hydrochloric acid. The organic layer was washed with water and saturated brine and dried over anhydrous sodium sulphate. Evaporation of the solvent afforded crude product as an oil which was chromatographed on silica gel. Elution with 20% ethyl acetate in hexane afforded a mixture of diastereoisomers as an oil (88 mg, 52%). $\delta_H$ (CDCl$_3$) 1.9–2.1 (2H, m), 2.17 and 2.34 (3H, s), 2.4–2.8 (3H, m), 2.99 and 3.08 (2H, m), 3.68 and 3.75 (3H, s), 4.09 (1H, m), 5.84 and 5.87 (1H, d, J 7.0 Hz), 6.57 and 6.75 (1H, d, J 7.0 Hz), 7.0–7.8 (12H, m) ppm.

Description 22 o-Phenoxybenzyl Alcohol

To a cooled (0°), stirred, solution of o-phenoxybenzoic acid (2.14 g, 10.0 mmol) in dry tetrahydrofuran (20 ml) under argon was added lithium aluminium hydride (0.19 g, 5 mmol) added in portions over 10 minutes. After a further 1 hour, water was added cautiously until effervescence ceased. The reaction mixture was partitioned between ethyl acetate and water and filtered. The organic layer was washed with saturated sodium hydrogen carbonate solution followed by water and dried over MgSO$_4$. Evaporation of solvent gave crude product (1.59 g, 80%). $\delta_H$ (CDCl3) 2.01 (1H, br t), 4.77 (2H, d, J 4.9 Hz), 6.9–7.5 (9H, m) ppm Description 23 o-Phenoxybenzaldehyde

A solution of the crude alcohol (1.59 g) from Description 22 in chloroform (25 ml) was treated with activated manganese dioxide (4 g) and stirred, under argon, for 10 days. The mixture was filtered through celite and the solvent removed to afford the desired product as a yellow oil (1.44 g, 92%). $\delta_H$ (CDCl3) 6.9–8.0 (9H, m), 10.54 (1H, s) ppm.

Description 24 o-Phenoxyphenylglycine Methyl Ester

The aldehyde (1.44 g, 7.27 mmol) from Description 23 was converted to the crude amino acid using essentially the method of Monianari et al. (Synthesis 1979, 26), but with some changes to the final purification. The crude solid material obtained after neutralization and evaporation of the water was stirred in methanol (35 ml), presaturated with hydrogen chloride gas, overnight. The methanol was removed under reduced pressure and the residue partitioned between ethyl acetate and an excess of saturated NaHCO3 solution. The organic layer was washed with water and dried. Removal of the solvent afforded the crude product as a pale oil which was chromatographed on silica gel. Elution with ethyl acetate gave the desired product as an oil (80 mg, 4% over 2 stages). $\delta_H$ (CDCl$_3$) 1.66 (2H, br s), 3.61 (3H, s), 4.82 (1H, s), 6.89 (1H, d, J 8.0 Hz), 6.99 (2H, d, J 7.5 Hz), 7.1–7.4 (6H, m) ppm.

Description 25

N-(2'-acetylthiomethyl-4'-phenylbutanoyl)-o-phenoxy-phenylglycine Methyl Ester

To a cooled (0°), stirred solution of 2-acetylthiomethyl-4-phenylbutanoic acid prepared as in Description 5, (78 mg, 0.31 mmol) in dry tetrahydrofuran (5 ml) containing dry dimethylformamide (1 drop), was added sodium hydride (14 mg of a 55% suspension in oil, 0.31 mmol). The reaction mixture was allowed to reach room temperature and stirring was continued for a further 15 mins. The suspension was then recooled (0°) and treated with oxalyl chloride (33 ul, 0.37 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) solution of o-phenoxy-phenylglycine methyl ester (Description 24, 80 mg, 0.31 mmol) in dry tetrahydrofuran (5 ml) was treated with triethylamine (44 ul, 0.31 mmol) followed by a solution of the above acid chloride in dry tetrahydrofuran (3 ml) added over 1 minute. The mixture was stirred at ambient temperature for 3 hours and then partitioned between ethyl acetate and 1 M hydrochloric acid. The organic layer was washed with water and saturated brine and dried over anhydrous sodium sulphate. Evaporation of the solvent afforded crude product as an oil which was chromatographed on silica gel. Elution with 20% ethyl acetate in hexane afforded diastereoisomer A as an oil (41 mg, 27%). $\delta_H$ (CDCl$_3$) 1.86 (1H, m), 2.03 (1H, m), 2.23 (3H, s), 2.32 (1H, m), 2.73 (2H, m), 3.00 (2H, d, J 7.8 Hz), 3.61 (3H, s), 5.87 (1H, d, J 8.1 Hz), 6.65 (1H, d, J 8.1 Hz), 6.87 (1H, dd, J 8.0 and 1.0 Hz), 6.99 (2H, d, J 7.8 Hz), 7.1–7.5 (11H, m) ppm. CIMS MH$^+$ 492. This was followed by diastereoisomer B as an oil (51 mg, 34%). $\delta_H$ (CDCl$_3$) 1.90 (2H, m), 2.32 (3H, s), 2.50 (3H, m), 3.08 (2H, m), 3.60 (3H, s), 5.87 (1H, d, J 7.9 Hz), 6.75 (1H, d, J 7.9 Hz), 6.8–7.5 (14H, m) ppm. CIMS MH$^+$ 492.

Description 26 p-Phenoxyphenylglycine Methyl Ester p-Phenoxybenzaldehyde (3.96 g, 0.02 mmol) was converted to the crude amino acid using essentially the method of Monianari et al. (Synthesis 1979, 26), but with some changes to the final purification. The crude solid material obtained after neutralization and evaporation of the water was stirred in methanol (35 ml), presaturated with hydrogen chloride gas, for 3 days. The methanol was removed under reduced pressure and the residue partitioned between ethyl acetate and an excess of saturated NaHCO3 solution. The organic layer was washed with water and dried. Removal of the solvent afforded the crude product as a pale oil which was chromatographed on silica gel. Elution with ethyl acetate gave the desired product as an oil (100 mg, 2% over 2 stages). $\delta_H$(CDCl$_3$) 1.76 (2H, br s), 3.73 (3H, s), 4.62 (1H, s), 6.9–7.4 (9H, m) ppm.

Description 27

N-(2'-acetylthiomethyl-4'-phenylbutanoly)-p-phenoxy-phenylglycine Methyl Ester

To a cooled (0°), stirred solution of 2-acetylthiomethyl-4-phenylbutanoic acid prepared as in Description 5, (98 mg, 0.39 mmol) in dry tetrahydrofuran (5 ml) containing dry dimethylformamide (1 drop), was added sodium hydride (17 mg of a 55% suspension in oil, 0.39 mmol). The reaction mixture was allowed to reach room temperature and stirring was continued for a further 15 mins. The suspension was then recooled (0°) and treated with oxalyl chloride (41 ul, 0.47 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) solution of p-phenoxy-phenylglycine methyl ester (Description 26, 100 mg, 0.39 mmol) in dry tetrahydrofuran (5 ml) was treated with triethylamine (55 ul, 0.39 mmol) followed by a solution of the above acid chloride in dry tetrahydrofuran (3 ml) added over 1 minute. The mixture was stirred at ambient temperature for 3 hours and then partitioned between ethyl acetate and 1M hydrochloric acid. The organic layer was washed with water and saturated brine and dried over anhydrous sodium sulphate. Evaporation of the solvent afforded crude product as an oil which was chromatographed on silica gel. Elution with 20% ethyl acetate in hexane afforded diastereoisomer A as an oil (57 mg, 30%). $\delta_H$(CDCl$_3$) 1.86 (1H, m), 2.03 (1H, m), 2.28 (3H, s), 2.32 (1H, m), 2.73 (2H, m), 3.04 (2H, d, J 7.9 Hz), 3.77 (3H, s), 5 55 (1H, d, J 6.9 Hz), 6.49 (1H, d, J 6.9 Hz), 7.0–7.4 (14H, m) ppm. ESMS M+NH$_4^+$ 509. This was followed by diastereoisomer B as an oil (60 mg, 31%). $\delta_H$(CDCl$_3$) 1.90 (2H, m), 2.34 (3H, s), 2.50 (3H, m), 3.08 (2H, m), 3.77 (3H, s), 5.59 (1H, d, J 7.0 Hz), 6.65 (1H, d, J 7.0 Hz), 7.0–7.4 (14H, m) ppm. ESMS M+NH$_4^+$ 509.

Description 28 m-(p-methoxyphenoxy)-phenylglycine Methyl Ester m-(p-methoxyphenoxy)-benzaldehyde (4.56 ml, 0.02 mol) was converted to the crude amino acid using essentially the method of Monianari et al. (Synthesis 1979, 26), but with some changes to the final purification. The crude solid material obtained after neutralization and evaporation of the water was stirred in methanol (40 ml), presaturated with hydrogen chloride gas, overnight. The methanol was removed under reduced pressure and the residue partitioned between ethyl acetate and an excess of saturated NaHCO3 solution. The organic layer was washed with water and dried. Removal of the solvent afforded the crude product. Chromatography on silica gel, eluting with ethyl acetate, gave desired product as a pale oil (0.91 g, 16% over 2 stages). $\delta_H$(CDCl$_3$) 1.26 (2H, br s), 3.71 (3H, s), 3.82 (3H, s), 4.57 (1H, s), 6.8–7.3 (8H, m) ppm.

Description 29

N-(2'-acetylthiomethyl-4'-phenylbutanoyl)-m-(p-methoxyphenoxy)-phenylglycine Methyl Ester To a cooled (0°), stirred solution of 2-acetylthiomethyl-4-phenylbutanoic acid prepared as in Description 5, (126 mg, 0.50 mmol) in dry tetrahydrofuran (5 ml) containing dry dimethylformamide (1 drop), was added sodium hydride (22 mg of a 55% suspension in oil, 0.50 mmol). The reaction mixture was allowed to reach room temperature and stirring was continued for a further 15 mins. The suspension was then recooled (0°) and treated with oxalyl chloride (52 ul, 0.60 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) solution of m-(p-methoxyphenoxy)-phenylglycine methyl ester (Description 28, 144 mg, 0.50 mmol) in dry tetrahydrofuran (5 ml) was treated with triethylamine (70 ul, 0.50 mmol) followed by a solution of the above acid chloride in dry tetrahydrofuran (5 ml) added over 1 minute. The mixture was stirred at ambient temperature for 3 hours and then partitioned between ethyl acetate and 1M hydrochloric acid. The organic layer was washed with water and saturated brine and dried over anhydrous sodium sulphate. Evaporation of the solvent afforded crude product as an oil which was chromatographed on silica gel. Elution with 20% ethyl acetate in hexane afforded diastereoisomer A as an oil (72 mg, 28%). $\delta_H$(CDCl$_3$) 1.89 (1H, m), 2.02 (1H, m), 2.28 (3H, s), 2.40 (1H, m), 2.68 (2H, m), 3.01 (2H, d, J 7.0 Hz), 3.76 (3H, s), 3.81 (3H, s), 5.53 (1H, d, J 7.0 Hz), 6.52 (1H, d, J 7.0 Hz), 6.9–7.3 (13H, m) ppm. CIMS MH$^+$522. This was followed by diastereoisomer B as an oil (95 mg, 37%). $\delta_H$(CDCl$_3$) 1.90 (2H, m), 2.34 (3H, s), 2.50 (3H, m), 3.06 (2H, m), 3.76 (3H, s), 3.79 (3H, s), 5.57 (1H, d, J 7.1 Hz), 6.61 (1H, d, J 7.1 Hz), 6.9–7.3 (13H, m) ppm. CIMS MH$^+$522.

Description 30

(N-Ethyl-3-carbazolyl)glycine Methyl Ester

N-Ethyl-3-carbazolecarboxaldehyde (4.46 ml, 0.02 mol) was converted to the crude amino acid using essentially the method of Monianari et al. (Synthesis 1979, 26), but with some changes to the final purification. The crude solid material obtained after neutralization and evaporation of the water was stirred in methanol (35 ml), presaturated with hydrogen chloride gas, overnight. The methanol was removed under reduced pressure and the residue partitioned between ethyl acetate and an excess of saturated NaHCO3 solution. The organic layer was washed with water and dried. Removal of the solvent afforded the crude product. Chromatography on silica gel, eluting with ethyl acetate, gave desired product as a pale oil (25 mg, 0.5% over 2 stages). $\delta_H$(CDCl$_3$) 1.43 (3H, t, J 7.1 Hz), 1.95 (2H, br s), 3.72 (3H, s), 4.37 (2H, q, J 7.1 Hz), 4.83 (1H, s), 7.2–7.5 (5H, m), 8.11 (2H, m) ppm. ESMS MH$^+$283.

Description 31

N-(2'-acetylthiomethyl-4'-phenylbutanoyl)-(N-Ethyl-3-carbazolyl)glycine Methyl Ester To a cooled (0°), stirred solution of 2-acetylthiomethyl-4-phenylbutanoic acid prepared as in Description 5, (40 mg, 0.16 mmol) in dry tetrahydrofuran (5 ml) containing dry dimethylformamide (1 drop), was added sodium hydride (7 mg of a 55% suspension in oil, 0.16 mmol). The reaction mixture was allowed to reach room temperature and stirring was continued for a further 15 mins. The suspension was then recooled (0°) and treated with oxalyl chloride (17 ul, 0.19 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) solution of (N-Ethyl-3-carbazolyl) glycine methyl ester (Description 30, 45 mg, 0.16 mmol) in dry tetrahydrofuran (5 ml) was treated with triethylamine (22 ul, 0.16 mmol) followed by a solution of the above acid chloride in dry tetrahydrofuran (5 ml) added over 1 minute. The mixture was stirred at ambient temperature for 3 hours and then partitioned between ethyl acetate and 1M hydrochloric acid. The organic layer was washed with water and saturated brine and dried over anhydrous sodium sulphate. Evaporation of the solvent afforded crude product as an oil which was chromatographed on silica gel. Elution with 20% ethyl acetate in hexane afforded diastereoisomer A as an oil (26 mg, 32%). $\delta_H$ (CDCl$_3$) 1.43 (3H, t, J 7.2 Hz), 1.89 (1H, m), 2.02 (1H, m), 2.22 (3H, s), 2.40 (1H, m), 2.8 (2H, m), 3.04 (2H, d, J 7.7 Hz), 3.76 (3H, s), 4.38 (2H, q, J 7.2 Hz), 5.72 (1H, d, J 6.7 Hz), 6.53 (1H, d, J 6.7 Hz), 7.2–7.5 (10H, m) 8.12 (2H, m) ppm. ESMS MH$^+$517. This was followed by diastereoisomer B as an oil (28 mg, 34%). $\delta_H$ (CDCl$_3$) 1.43 (3H, t, J 7.2 Hz), 1.90 (2H, m), 2.35 (3H, s), 2.50 (3H, m), 3.12 (2H, m), 3.76 (3H, s), 4.37 (2H, q, J 7.2 Hz), 5.78 (1H, d, J 7.0 Hz), 6.68 (1H, d, J 7.0 Hz), 7.0–7.5 (10H, m) 8.10 (2H, m) ppm. ESMS MH$^+$517.

Description 32

N-(2'-RS-acetylthiomethyl-4'-phenylbutanoyl)-D-p-hydroxyphenylglycine Methyl Ester To a cooled (0°), stirred solution of 2-acetylthiomethyl-4-phenylbutanoic acid prepared as in Description 5, (252 mg, 1.0 mmol) in dry tetrahydrofuran (5 ml) containing dry dimethylformamide (1 drop), was added sodium hydride (44 mg of a 55% suspension in oil, 1.0 mmol). The reaction mixture was allowed to reach room temperature and stirring was continued for a further 15 mins. The suspension was then recooled (0°) and treated with oxalyl chloride (105 ul, 1.2 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) solution of D-p-hydroxyphenylglycine methyl ester, prepared from D-p-hydroxyphenylglycine with hydrogen chloride in methanol as in Description 4, (181 mg, 1.0 mmol) in dry tetrahydrofuran (5 ml) was treated with triethylamine (140 ul, 1.0 mmol) followed by a solution of the above acid chloride in dry tetrahydrofuran (5 ml) added over 1 minute. The mixture was stirred at ambient temperature for 3 hours and then partitioned between ethyl acetate and 1M hydrochloric acid. The organic layer was washed with water and saturated brine and dried over anhydrous sodium sulphate. Evaporation of the solvent afforded crude product as an oil which was chromatographed on silica gel. Elution with 33% ethyl acetate in hexane afforded the desired mixture of diastereoisomers as a pale gum (295 mg, 71%). $\delta_H$ (CDCl$_3$) 1.89 (1H, m), 2.02 (1H, m), 2.28 and 2.34 (3H, s), 2.4–2.7 (3H, m), 3.1 (2H, m), 3.75 (3H, s), 5.16 (1H, br s), 5.48 and 5.53 (1H, d, J 6.9 Hz), 6.44 and 6.60 (1H, d, J 6.9 Hz), 6.81 (2H, d, J 8.5 Hz), 7.0–7.3 (7H, m) ppm.

Description 33

N-(2'-R-acetylthiomethyl-4'-phenylbutanoyl)-p-benzyloxy-D-phenylglycine Methyl Ester and N-(2'-S-acetylthiomethyl-4'-phenylbutanoyl)-p-benzyloxy-D-phenylglycine Methyl Ester To a stirred solution of the p-hydroxyphenylglycine derivative of Description 32 (50 mg, 0.12 mmol) in dry tetrahydrofuran (2 ml) was added triphenyl phosphine (35 mg, 0.13 mmol) and benzyl alcohol (12 ul, 0.12 mmol) followed by diethyl azodicarboxylate (23 ul, 0.14 mmol). The resulting yellow solution was stirred at room temperature for 15 minutes before dilution with ethyl acetate. The organic layer was washed with water and dried (MgSO$_4$). The solvent was removed to afford a gum which was chromatographed on silica gel. Elution with 20% ethyl acetate in hexane gave diastereoisomer A as a white solid (15 mg, 25%). $\delta_H$ (CDCl$_3$) 1.89 (1H, m), 2.02 (1H, m), 2.27 (3H, s), 2.40 (1H, m), 2.68 (2H, m), 3.02 (2H, d, J 7.0 Hz), 3.75 (3H, s), 5.07 (2H, s), 5.50 (1H, d, J 6.8 Hz), 6.41 (1H, d, J 6.8 Hz), 6.97 (2H, d, J 8.7 Hz), 7.2–7.4 (12 H, m) ppm. EIMS M$^+$505. This was followed by diastereoisomer B as a gum (14 mg, 23%). $\delta_H$ (CDCl$_3$) 1.90 (2H, m), 2.34 (3H, s), 2.50 (3H, m), 3.08 (2H, m), 3.74 (3H, s), 5.06 (2H, s), 5.55 (1H, d, J 7.0 Hz), 6.57 (1H, d, J 7.0 Hz), 6.9–7.4 (14H, m) ppm. EIMS M$^+$505.

Description 34

N-(2'-R-acetylthiomethyl-4'-phenylbutanoyl)-p-(2"-thienylmethoxy)-D-phenylglycine Methyl Ester and N-(2'-S-acetylthiomethyl-4'-phenylbutanoyl)-p-(2"-thienylmethoxy)-D-phenylglycine Methyl Ester To a stirred solution of the p-hydroxyphenylglycine derivative of Description 32 (156 mg, 0.38 mmol) in dry tetrahydrofuran (2 ml) was added triphenyl phosphine (125 mg, 0.48 mmol) and 2-thiophenemethanol (53 ul, 0.56 mmol) followed by diethyl azodicarboxylate (78 ul, 0.50 mmol). The resulting yellow solution was stirred at room temperature for 15 minutes before dilution with ethyl acetate. The organic layer was washed with water and dried (MgSO$_4$). The solvent was removed to afford a gum which was chromatographed on silica gel. Elution with 20% ethyl acetate in hexane gave diastereoisomer A as a colourless gum (50 mg, 26%). $\delta_H$ (CDCl$_3$) 1.89 (1H, m), 2.02 (1H, m), 2.27 (3H, s), 2.37 (1H, m), 2.68 (2H, m), 3.02 (2H, d, J 7.6 Hz), 3.75 (3H, s), 5.22 (2H, s), 5.51 (1H, d, J 6.9 Hz), 6.44 (1H, d, J 6.9 Hz), 7.0–7.4 (12H, m) ppm. ESMS MH$^+$512. This was followed by diastereoisomer B as a gum (60 mg, 31%). $\delta_H$ (CDCl$_3$) 1.90 (2H, m), 2.34 (3H, s), 2.50 (3H, m), 3.08 (2H, m), 3.74 (3H, s), 5.21 (2H, s), 5.56 (1H, d, J 7.0 Hz), 6.59 (1H, d, J 7.0 Hz), 7.0–7.4 (12H, m) ppm. ESMS MH$^+$512.

Description 35 p-Methoxycarbonylbenzaldehyde

Methanol (50 ml) was cooled (0°) and saturated with hydrogen chloride gas. p-Carboxybenzaldehyde (5.0 g) was added and the resulting solution stirred at room temperature for 3 days. The solvent was removed under reduced pressure and the residue was partitioned between ethyl acetate and 5M hydrochloric acid. The organic layer was washed twice with water and dried. The solvent was removed to afford the product as a white solid (5.40 g, 100%). $\delta_H$ (CDCl$_3$) 3.96 (3H, s), 7.96 (2H, dd, J 6.8 and 1.7 Hz), 8.20 (2H, dd, J 6.8 and 1.7 Hz), 10.11 (1H, s) ppm.

Description 36 p-Methoxycarbonylbenzyl Alcohol

A stirred solution of p-methoxycarbonylbenzaldehyde (Description 35, 0.82 g, 5.0 mmol) in methanol (10 ml) at 0° under argon was treated with sodium borohydride (50 mg, 1.25 mmol), added in portions over 5 minutes. After stirring overnight the reaction mixture was partitioned between ethyl acetate and water. The organic layer was washed with water and dried (MgSO$_4$). Removal of the solvent gave the desired product as a colourless solid (0.78 g, 94%). $\delta_H$ (CDCl$_3$) 1.83 (1H, t, J 5.9 Hz), 3.93 (3H, s), 4.78 (1H, d, J 5.9 Hz), 7.45 (2H, d, J 8.1 Hz), 8.04 (2H, d, J 8.1 Hz) ppm.

Description 37

N-(2'-R-acetylthiomethyl-4'-phenylbutanoyl)-p-(p-methoxycarbonyl)-benzyloxy-D-phenylglycine Methyl Ester and N-(2'-S-acetylthiomethyl-4'-phenylbutanoyl)-p-(p-methoxycarbonyl)-benzyloxy-D-phenylglycine Methyl Ester To a stirred solution of the p-hydroxyphenylglycine derivative from Description 36 (95 mg, 0.23 mmol) in dry tetrahydrofuran (2 ml) was added triphenyl phosphine (75 mg, 0.29 mmol) and p-methoxycarbonylbenzyl alcohol (Description 36, 57 mg, 0.34 mmol) followed by diethyl azodicarboxylate (48 ul, 0.30 mmol). The resulting yellow solution was stirred at room temperature for 15 minutes before dilution with ethyl acetate. The organic layer was washed with water and dried (MgSO$_4$). The solvent was removed to afford a gum which was chromatographed on silica gel. Elution with 25% ethyl acetate in hexane gave diastereoisomer A as a gum (37 mg, 29%). $\delta_H$ (CDCl$_3$) 1.89 (1H, m), 2.02 (1H, m), 2.26 (3H, s), 2.40 (1H, m), 2.68 (2H, m), 3.01 (2H, d, J 8.0 Hz), 3.74 (3H, s), 3.92 (3H, s), 5.12 (2H, s), 5.50 (1H, d, J 6.8 Hz), 6.46 (1H, d, J 6.8 Hz), 6.95 (2H, d, J 8.7 Hz),, 7.2–7.3 (7H, m), 7.49 (2H, d, J 8.3 Hz), 8.06 (2H, d, J 8.3 Hz) ppm. EIMS M$^+$563. This was followed by diastereoisomer B as a gum (37 mg, 29%). $\delta_H$ (CDCl$_3$) 1.90 (2H, m), 2.33 (3H, s), 2.50 (3H, m), 3.08 (2H, m), 3.73 (3H, s), 3.92 (3H, s), 5.11 (2H, s), 5.55 (1H, d, J 7.0 Hz), 6.62 (1H, d, J 7.0 Hz), 6.95 (2H, d, 8.7 Hz), 7.04 (2H, d, J 8.0 Hz), 7.2–7.3 (5H, m), 7.48 (2H, d, J 8.3 Hz), 8.05 (2H, d, J 8.3 Hz) ppm. EIMS M$^+$563.

Description 38

Ethyl 2-(5-benzyl)thien-2-yl-2-oxoacetate

Ethyl oxalyl chloride (1.12 ml) was added to a stirred suspension of aluminium chloride (1.4 g) in dichloromethane (15 ml). A solution of 2-benzylthiophene (Arcoria et al., J. Het. Chem. (1972), 9, 849–852) (1.74 g) in dichloromethane (10 ml) was added dropwise over 15 min. When the addition was complete the mixture was stirred at room temperature for 0.5 h and then poured into dilute hydrochloric acid (25 ml). The organic phase was separated, washed with water and brine, dried over magnesium sulphate and evaporated. The product (2.10 g) was isolated by column chromatography of the residue (Kieselgel: 10% ethyl acetate in hexane). $v_{max}$ (CHCl$_3$) 1731 and 1659 cm$^{-1}$. $\delta$ (CDCl$_3$) 1.41 (3H, t, J 7.15 Hz), 4.19 (2H, S), 4.40 (2H, q, J 7.18 Hz), 6.90 (1H, d, J 3.93 Hz), 7.23–7.37 (5H, m), 7.98 (1H, d, J 3.95 Hz), m/z 274 (M$^+$). [Found (HRMS): m/z 274.0671. Calc. for C$_{15}$H$_{14}$O$_3$S; 274.0664].

Description 39

Ethyl 2-(5-benzyl)thien-2-yl-2-hydroxyiminoacetate

Hydroxylamine hydrochloride (695 mg) was added to a stirred solution of ethyl 2-(5-benzyl)thien-2-yl-2-oxoacetate (Description 38) (1.37 g) in ethanol (30 ml). When the solid had dissolved the mixture was allowed to stand for 48 h. The solvent was evaporated and the residue partitioned between ethyl acetate and water. The organic phase was washed with water and brine, dried over magnesium sulphate and evaporated. The product (1.07 g) was obtained by recrystallisation of the residue from ethyl acetate/hexane. $v_{max}$ (CHCl$_3$) 3464, 3272, 1734 cm$^{-1}$. $\delta$ (CDCl$_3$) 1.40 (3H, t, J 7.37), 4.12 and 4.19 (2H, two s's), 4.35–4.49 (2H, m), 6.73 and 6.85 (1H, two d's, J 3.79), 7.03 and 7.95 (1H, two d's, J 3.63), 7.21–7.36 (5H, m), 8.67 (1H, s). m/z 289 (M$^+$). [Found (HRMS): m/z 289.0776. Calc. for C$_{15}$H$_{15}$NO$_3$S; 289.0773].

Description 40

2-[(5-Benzyl)thien-2yl]-N-[2-(acetylthiomethyl)-4-phenylbutyryl]glycine Ethyl Ester A stirred suspension of ethyl 2-(5-benzyl)thien-2-yl-2-hydroxyiminoacetate (Description 39) 289 mg) in methanol (1 ml) and 50% formic acid (2 ml) was cooled in an ice-bath. Zinc dust (150 mg) was added in portions over 20 min., then the mixture was stirred at 0° C. for a further 4h. The solid was filtered off and washed with 50% formic acid. The combined filtrates were evaporated and the residue stirred with chloroform and water, potassium carbonate was added until effervescence ceased. The organic phase was separated, dried over magnesium sulphate and evaporated to ~1 ml. The residue was dissolved in dichloromethane (10 ml) and used as indicated below.

Oxalyl chloride (0.1 ml) and dimethylformamide (1 drop) were added to a stirred solution of 2-(acetylthiomethyl)-4-phenylbutanoic acid, prepared as in Description 5, (252 mg) in dichloromethane (10 ml). The mixture was stirred at room temperature for 1 h and then the solvent was evaporated and chloroform evaporated from the residue twice. The residue was dissolved in dichloromethane (2 ml) and added to a stirred solution of the amine previously prepared. Triethylamine (0.28 ml) was added and the mixture stirred for 2 h. The solution was washed successively with citric acid solution, water, sodium bicarbonate solution, water and brine, dried over magnesium sulphate and evaporated. The product (352 mg) was isolated by column chromatography of the residue using gradient elution (Kieselgel:20% going to 40% ethyl acetate in hexane). $v_{max}$ (CHCl$_3$) 3421, 1739, 1683 cm$^{-1}$. $\delta$ (CDCl$_3$) 1.27 (3H, t, J 7.01 Hz), 1.74–2.11 (2H, m), 2.21–2.80 (3H, m), 2.24 and 2.32 (3H, two s's), 2.98–3.14 (2H, m), 4.08 and 4.10 (2H, two s's), 4.18–4.31 (2H, m), 5.72–5.79 (1H, two d's J 7.11 Hz), 6.32 and 6.47 (1H, two d's, J 7.22 Hz), 6.65–6.69 (1H, m), 6.87–6.90 (1H, m), 7.07–7.31 (1H, m). m/z 509 (M$^+$). [Found (HRMS): m/z 509.1685. Calc. for C$_{28}$H$_{31}$NO$_4$S$_2$; 506.1695].

Description 41

Ethyl 2-(5-benzyl)furan-2yl-2-oxoacetate

Ethyl oxalyl chloride (1.12) was added to a stirred suspension of aluminium chloride (1.4 g) in dichloromethane (15 ml). The mixture was cooled in an ice bath and a solution of 2-benzylfuran (Hall et al., (1987) 24, 1205–1213) (1.58 g) in dichloromethane (10 ml) was added dropwise. When the addition was complete the mixture was stirred at 0° C. for 15 min. and then poured into dilute hydrochloric acid (25 ml). The organic phase was separated and washed with water and brine, then dried over magnesium sulphate and evaporated. The product (877 mg) was isolated by column chromatography of the residue using gradient elution (Kieselgel:10% going to 20% ethyl acetate in hexane). $v_{max}$ (CHCl$_3$) 1733 and 1665 cm$^{-1}$. δ (CDCl$_3$) 1.14 (3H, t, J 7.09 Hz), 4.09 (2H, s), 4.40 (2H, q, J 7.02 Hz), 6.18 (1H, d, J 3.82 Hz), 7.23–7.37 (5H, m), 7.64 (1H, d, J 3.67 Hz); m/z 258 (M$^+$). [Found (HRMS): m/z 258.0888. Calc. for C$_{15}$H$_{14}$O$_4$; 258.0892].

Description 42

Ethyl 2-(5-benzyl)furan-2-yl-2-hydroxyiminoacetate

The title compound was prepared from ethyl 2-(5-benzyl) furan-2-yl-2-oxoacetate (Description 41) by the procedure of Description 39 except that the product was isolated by column chromatography using gradient elution (Kieselgel:20% going to 50% ethyl acetate in hexane). ν$_{max}$ (CHCl$_3$) 3563, 3282, 1736 cm$^{-1}$. δ (CDCl$_3$) 1.35 and 1.38 (3H, two t's, J 7.24 Hz), 4.01 and 4.03 (2H, two s's), 4.33–4.47 (2H, m), 6.04 and 6.14 (1H, two d's, J 3.44 Hz), 6.57 (½H, d, J 3.41 Hz), 7.21 –7.35 (5½H, m), 9.03 and 9.23 (1H, 2 broad s's). m/z 273 (M$^+$). [Found (HRMS): m/z 273.1006. Calc. for C$_{15}$H$_{15}$NO$_4$; 273.1001].

Description 43

2-[(5-Benzyl)furan-2yl]-N-[2-(acetylthiomethyl)-4-phenylbutyryl]glycine Ethyl Ester The title compound was prepared from ethyl 2-(5-benzyl) furan-2-yl-2-hydroxyiminoacetate (Description 42) by the procedure of Description 40. ν$_{max}$ (CHCl$_3$) 3430, 1742 and 1683 cm$^{-1}$. δ (CDCl$_3$) 1.21 (3H, t, J 7.07 Hz), 1.75–2.13 (2H, m), 2.24–2.80 (2H, m), 2.26 and 2.32 (3H, two s's), 2.98–3.16 (2H, m), 3.92 and 3.95 (2H, two s's), 4.22 (2H, q, J 7.13 Hz), 5.66 and 5.72 (1H, two d's, J 7.61 Hz), 5.94–5.95 (1H, m), 6.27–6.29 (1H, m), 6.37 and 6.46 (1H, two d's, J 7.56 Hz), 7.07–7.31 (10H, m). m/z 493 (M$^+$). [Found (HRMS): m/z 493.1930. Calc. for C$_{28}$H$_{31}$NO$_5$S; 493.1923].

Description 44

2-(Tetrahydrofuran-3-methyl)thiophene

A solution of n-butyllithium (12.5 ml of 1.6N in hexanes) was added to a stirred solution of thiophene (1.6 ml) in tetrahydrofuran (90 ml) under argon. The solution was stirred for 0.5 h and then a solution of 3-bromomethyltetrahydrofuran Schweizer et al., J. Org. Chem. (1969) 34, 212–218) (3.3 g) in tetrahydrofuran (10 ml) was added dropwise. The mixture was stirred for 4 h and then acetic acid (2 ml) was added. The mixture was partitioned between ethyl acetate and water and the organic phase was washed with water, sodium bicarbonate solution, water and brine. The solution was dried over magnesium sulphate and evaporated. The product (866 mg) was isolated by column chromatography (Kieselgel:20% ethyl acetate in hexane). δ (CDCl$_3$) 1.56–1.71 (1H, m), 2.01–2.14 (1H, m), 2.49–2.66 (1H, m), 2.90 (2H, d, J 7.53 Hz), 3.50 (1H, dd, J 6.23 and 8.59 Hz), 3.72–4.16 (2H, m), 6.80 (1H, dd, J 0.78 and 3.38 Hz), 6.92 (1H, dd, J 3.44 and 5.05 Hz), 7.13 (1H, dd, J 1.21 and 5.19 Hz).

Description 45

Ethyl 2-[5-(tetrahydrofuran-3-ylmethyl)thien-2yl]-2-oxoacetate

Ethyl oxalyl chloride (0.15 ml) was added to a stirred suspension of aluminium chloride (200 mg) in dichloromethane (10 ml). When the solid had dissolved a solution of 2-(tetrahydrofuran-3-ylmethyl)thiophene (Description 44) (240 mg) in dichloromethane 2 ml) was added. The mixture was stirred at room temperature for 1 h and then shaken with dilute hydrochloric acid (10 ml). The organic phase was separated and washed with water and brine, dried over magnesium sulphate and evaporated. The product (93 mg) was isolated by column chromatography using gradient elution (Kieselgel: 25% going to 50% ethyl acetate in hexane). ν$_{max}$ (CHCl$_3$) 1731 and 1659 cm$^{-1}$. δ (CDCl$_3$) 1.42 (3H, t, J 7.24 Hz), 1.57–1.71 (1H, m), 2.03–2.17 (1H, m), 2.50–2.67 (1H, m), 2.88–3.04 (1H, m), 3.50 (1H, dd, J 6.04 and 8.66 Hz), 3.73–3.95 (2H, m), 4.42 (2H, q, J 7.22 Hz), 6.92 (1H, d, J 3.91 Hz), 7.99 (1H, d, J 3.91 Hz). m/z 268 (M$^+$). [found (HRMS): m/z 268.0761. Calc. for C$_{13}$H$_{16}$O$_4$S; 268.0769].

Description 46

Ethyl 2-[5-(tetrahydrofuran-3-ylmethyl)thien-2-yl]-2-hydroxyiminoacetate

Hydroxylamine hydrochloride (70 mg) was added to a stirred solution of ethyl 2-[5-tetrahydrofuran-3-ylmethyl) thien-2-yl]-2-oxoacetate (Description 45) (130 mg) in ethanol (2 ml). The mixture was stirred for 48 h and the solvent evaporated. The residue was partitioned between ethyl acetate and water, the organic phase was washed with brine, dried over magnesium sulphate and evaporated. The product (95 mg) was obtained by column chromatography of the residue (Kieselgel: 50% ethyl acetate in hexane). ν$_{max}$ (CHCl$_3$) 3564, 3242, 1733 cm$^{-1}$. δ (CDCl$_3$) 1.43 (3H, t, J 7.19 Hz), 1.61–1.74 (1H, m), 2.03–2.16 (1H, m), 2.51–2.66 (1H, m), 2.87–2.96 (2H, m), 3.48–3.56 (1H, m), 3.74–3.96 (3H m), 4.38–4.51 (2H, m), 6.75 and 6.87 (1H, two d's J 3.57 ), 7.02 and 7.92 (1H, two d's J 3.60 Hz), 8.84 and 9.82 (1H, two s's). m/z 283 (M$^+$). [Found (HRMS): 283.0882. Calc. for C$_{13}$H$_{17}$NO$_4$S. 283.0878].

Description 47

2-[5-tetrahydrofuran-3-ylmethyl)thien-2-yl]-N-[2-(acetylthiomethyl)-4-phenylbutyryl]glycine Ethyl Ester The title compound was prepared from ethyl 2-[5-(tetrahydrofuran-3-ylmethyl)thien-2-yl]-2-hydroxyiminoacetate (Description 46) by the procedure of Description 40 except that the eluent used was 40% ethyl acetate in hexane. ν$_{max}$ (CHCl$_3$) 3422, 1739 and 1682 cm$^{-1}$. δ (CDCl$_3$) 1.30 (3H, t, J 7.07 Hz), 1.58–1.72 (2H, m), 1.80–2.18 (3H, m), 2.30 and 2.34 (3H, two s's), 2.30–2.89 (5H, m), 3.04–3.13 (2H, m), 3.44–3.52 (1H, m), 3.71–3.91 (3H, m), 4.22–4.32 (2H, m), 5.75–5.82 (1H, two d's, J 7.27 Hz), 6.40 and 6.54 (1H, two d's, J 7.24 Hz), 6.66 (1H, d, J 3.40 Hz), 7.09–7.32 (5H, m).

Description 48

Ethyl 2-(5-methyl)thien-2-yl-2-oxoacetate

Ethyl oxalyl chloride (2.24 mg) was added to a stirred suspension of aluminium chloride (2.8 g) in dichloromethane (30 ml). The mixture was stirred at room temperature for 0.5 h and then a solution of 2-methylthiophene (1.96 g) in dichloromethane (20 ml) was added dropwise. When the addition was complete the mixture was stirred for a further 0.5 h and then poured into dilute hydrochloric acid (50 ml). The organic phase was separated and washed with water and brine, dried over magnesium sulphate and evaporated. The product (2.99 g) was isolated by column chromatography of the residue (Kieselgel: 20% ethyl acetate in hexane as eluent). $v_{max}$ (CHCl$_3$) 1731 and 1659 cm$^{-1}$. δ (CDCl$_3$) 1.42 (3H, t, J 7.18 Hz), 2.58 (3H, s), 4.42 (2H, q, J 7.05 Hz), 6.88 (1H, d, J 3.86 Hz), 7.96 (1H, d, J 3.89 Hz).

Description 49

Ethyl 2-(5-bromomethyl)thien-2-yl-2-oxoacetate

A mixture of ethyl 2-(5-methyl)thien-2-yl-2-oxoacetate (Description 48) (1.98 g) and N-bromo-succinimide (1.78 g) in carbon tetrachloride (50 ml) was heated under reflux and irradiated with a tungsten filament lamp for 2 h. The mixture was cooled and the solid filtered off and washed with chloroform. The combined filtrates were evaporated and the residue dissolved in ethyl acetate, and the solution was washed twice with water, then brine, dried over magnesium sulphate and evaporated. The product (1.85 g) was isolated by column chromatography of the residue using gradient elution (Kieselgel: 10% going to 20% ethyl acetate in hexane). $v_{max}$ (film) 1731, 1665 cm$^{-1}$. δ (CDCl$_3$) 1.43 (3H, t, J 7.01 Hz), 4.43 (2H, q, J 7.01 Hz), 4.69 (2H, s), 7.19 (1H, d, J 3.97 Hz), 8.00 (1H, d, J 4.00 Hz).

Description 50

Ethyl 2-[5-(1-tetrazolylmethyl)thien-2-yl]-2-oxoacetate and ethyl 2-[5-(2-tetrazolylmethyl)thien-2-yl]-2-oxoacetate Triethylamine (0.42 ml) was added to a stirred mixture of tetrazole (210 mg) and ethyl 2-(5-bromomethyl)thien-2-yl-2-oxoacetate (Description 49) (821 mg) in acetonitrile (12 ml). The mixture was stirred overnight and then partitioned between ethyl acetate and water. The organic phase was washed successively with water, dilute hydrochloric acid, water and brine, dried over magnesium sulphate and evaporated. The products were separated by column chromatography using gradient elution (Kieselgel: 25% going to 50% ethyl acetate in hexane). Eluted first was ethyl 2-[5-(2-tetrazolylmethyl)thien-2-yl]-2-oxoacetate (244 mg). $v_{max}$ (CHCl$_3$) 1732 and 1672 cm$^{-1}$. δ (CDCl$_3$) 1.42 (3H, t, J 7.23 Hz), 4.42 (2H, q, J 7.26 Hz). 6.03 (2H, s), 7.23 (1H, d, J 4.14 Hz), 8.04 (1H, d, J 3.94 Hz), 8.56 (1H, s). m/z 266 (M$^+$). [Found (HRMS): m/z 266.0469. Calc. for C$_{10}$H$_{10}$N$_4$O$_3$S. 266.0474]. Eluted next was ethyl 2-[5-(2-tetrazolylmethyl)thien-2-yl]-2-oxoacetate (416 mg). $v_{max}$ (CHCl$_3$) 1732 and 1673 cm$^{-1}$. δ (CDCl$_3$) 1.43 (3H, t, J 7.02 Hz), 4.43 (2H, q, J 7.19 Hz), 5.85 (2H, s), 7.20 (1H, d, J 3.93 Hz), 8.07 (1H, d, J 3.96 Hz), 8.69 (1H, s). m/z 266 (M$^+$). [Found (HRMS): m/z 266.0469. Calc. for C$_{10}$H$_{10}$N$_4$O$_3$S; 266.0474].

Description 51

Ethyl 2-[5-(1-tetrazolylmethyl)thien-2-yl]-2-hydroxyiminoacetate

Hydroxylamine hydrochloride (205 mg) was added to a stirred mixture of ethyl 2-[5-(1-tetrazolylmethyl)thien-2-yl]-2-oxoacetate (Description 50) (394 mg) and ethanol (10 ml). The mixture was left at room temperature for 3 days, then the solvent was evaporated and the residue partitioned between ethyl acetate and water. The organic phase was washed with water and brine and dried over magnesium sulphate. The solution was evaporated to give the product (376 mg) as a mixture of isomers. $v_{max}$ (nujol) 3131, 1746, 1724 cm$^{-1}$. δ (CD$_3$COCD$_3$), 1.31–1.39 (3H, m), 4.36 and 4.42 (2H, two q's, J 7.22 Hz), 6.02 and 6.08 (2H, two s's), 7.10 and 7.25 (1H, two d's, J 3.73 Hz), 7.31 and 7.78 (1H, two d's, J 3.98 Hz), 9.26 and 9.30 (1H, two s's), 11.14 and 12.25 (1H, two broad s's). m/z 280 (M–H)$^-$. [Found: m/z 281.0584. Calc. for C$_{10}$H$_{11}$N$_5$O$_3$S; 281.0583].

Description 52

2-[5-(1-Tetrazolylmethyl)thien-2-yl]-N-[2-(acetylthiomethyl)-4-phenylbutyryl]glycine Ethyl Ester The title compound was prepared from ethyl 2-[5-(1-tetrazolylmethyl)thien-2-yl]-2-hydroxyiminoacetate (Description 51) by the procedure of Description 40. $v_{max}$ (CHCl$_3$) 3415, 1740 and 1685 cm$^{-1}$. δ (CDCl$_3$) 1.23–1.32 (3H, m), 1.80–2.10 (2H, m), 2.30 and 2.33 (3H, two s's), 2.35–2.80 (3H, m), 2.98–3.15 (2H, m), 4.21–4.34 (2H, m), 5.71 (2H, two s's), 5.78–5.84 (1H, m), 6.62 and 6.73 (1H, two d's, J 7.27 Hz), 6.99–7.32 (7H, m), 8.55 and 8.59 (1H, two s's). m/z 502 (MH$^+$). [Found (HRMS): m/z 502.1587. Calc. for C$_{23}$H$_{27}$N$_5$O$_4$S$_2$; 502.1583].

Description 53

Ethyl 2-[5-(2-tetrazolylmethyl)thien-2-yl]-2-hydroxyiminoacetate

The title compound was prepared from ethyl 2-[5-(2-tetrazolylmethyl)thien-2-yl]-2-oxoacetate (Description 50) by the procedure of Description 51. $v_{max}$ (CHCl$_3$) 3558, 3250, 1734 cm$^{-1}$. δ (CDCl$_3$) 1.41 and 1.42 (3H, two t's, J 7.16 Hz), 4.41 and 4.47 (2H, two q's, J 7.22 Hz), 5.96 and 6.03 (2H, two s's), 7.12 (s) and 7.23 (d, J 3.99 Hz) and 8.01 (d, J 4.08 Hz) (2H), 8 55 (1H, s). m/z 299 (MNH$_4^+$).

DESCRIPTION 54

2-[-5-(2-Tetrazolylmethyl)thien-2-yl]-N-[2-(acetylthiomethyl)-4-phenylbutyryl]glycine ethyl ester The title compound was prepared from ethyl 2-[5-(2-tetrazolylmethyl)thien-2-yl]-2-hydroxyiminoacetate (Description 53) by the procedure of Description 40. $v_{max}$ (CHCl$_3$) 3416, 1704, 1684cm$^{-1}$. δ(CDCl$_3$) 1.23–1.31 (3H, m), 1.80–2.13 (2H, m), 2.30 and 2.33 (3H, two s's), 2.30–2.78 (3H, m), 2.97–3.15 (2H, m), 4.19–4.36 (2H, m), 5.91 and 5.92 (2H, two s's), 6.96–7.32 (7H, s), 8.44 and 8.52 (1H, two s's). m/z 519 (MNH$_4^+$).

DESCRIPTION 55

Ethyl 2-[5-(1,2,3-triazol-1-ylmethyl)thien-2-yl]-2-oxoacetate and ethyl 2-[5-(1,2,3-triazol-2-ylmethyl)thien-2-yl]-2-oxoacetate Triethylamine (0.28 ml) was added to a stirred solution of ethyl 3-(5-bromomethyl)thien-2-yl-2-oxoacetate (Description 49) (554 mg) and 1,2,3-triazole (138 mg) in acetonitrile. The mixture was stirred at room temperature for 20 h and then partitioned between ethyl acetate and water. The organic phase was washed with water and brine, dried over magnesium sulphate and evaporated. The products were separated by column chromatography using gradient elution (Kieselgel:50% ethyl acetate in hexane going to ethyl acetate). Eluted first was ethyl 2-[5-(1,2,3-triazol-2-ylmethyl)thien-2-yl]-2-oxoacetate (31 mg). $v_{max}$ (CHCl$_3$) 1732, 1668 cm$^{-1}$. δ(CDCl$_3$) 1.41 (3H, t, J 7.04 Hz), 4.41 (2H, q, J 7.07 Hz), 5.82 (2H, s), 7.13 (1H, d, J 4.11 Hz), 7.67 (2H, s), 8.01 (1H, d, J 3.94 Hz). m/z 265 (M$^+$). [Found (HMRS): 265.0524. Calc. for C$_{11}$H$_{11}$N$_3$O$_3$S;265.0521]. Eluted next was ethyl 2-[5-(1,2,3-triazol-1-ylmethyl)thien-2-yl]-2-oxoacetate (66 mg). $v_{max}$(CHCl$_3$) 1732, 1671cm$^{-1}$. δ(CDCl$_3$) 1.42 (3H, t, J 7.16 Hz), 4.42 (2H, q, J 7.14 Hz), 5.80 (2H, s), 7.12 (1H, d, J 3.90 Hz), 7.63 (1H, s), 7.76 (1H,s), 8.03 (1H, d, J 3.94 Hz).

DESCRIPTION 56
Ethyl 2-[5-(1,2,3-triazol-1-ylmethyl)thien-2-yl]-2-hydroxyiminoacetate Hydroxylamine hydrochloride (167 mg) was added to a stirred solution of ethyl 2-[5-(1,2,3-triazol-1-ylmethyl)thien-2-yl]-2-oxoacetate (Description 55) (319 mg) in ethanol (5 ml). The mixture was stirred for 18 h then the solvent was evaporated and the residue partitioned between ethyl acetate and water. The organic phase was washed with water and brine, dried over magnesium sulphate and evaporated to give the product (336 mg). $v_{max}$(nujol) 3136, 1736cm$^{-1}$. $\delta$(CD$_3$COCD$_3$) 1.33–1.39 (3H, m), 4.30–4.46 (2H, m), 5.89 and 5.95 (2H, two s's), 7.07 and 7.17 (1H, two d's, J 3.81 Hz), 7.23 and 7.75 (1H, two d's, J 3.90 Hz), 8.07 and 8.08 (1H, two s's). m/z 281 (MH$^+$)

DESCRIPTION 57
2-[5-(1,2,3-Triazol-1-ylmethyl)thien-2-yl)-N-[2-(acetylthiomethyl)-4-phenylbutyryl]glycine ethyl ester The title compound was prepared from ethyl 2-[5-(1,2,3-triazol-1-ylmethyl)thien-2-yl]-2-hydroxyiminoacetate (Description 56) by the procedure of Description 40 except that the eluent was 20% going to 40% ethyl acetate in hexane. $v_{max}$(CHCl$_3$)3416, 1739, 1684cm$^{-1}$. $\delta$(CDCl$_3$) 1.29 (3H, t, J 6.64 Hz), 1.80–2.10 (2H, m), 2.29 and 2.33 (3H, two s's), 2.30–2.80 (3H, m), 2.98–3.15 (2H, m), 4.20–4.33 (2H, m), 5.67 and 5.68 (2H, two s's), 5.78 and 5.83 (1H, two d's, J 7.33 Hz), 6.54 and 6.67 (1H, two d's, J 7.32 Hz), 6.97–7.32 (7H, m), 7.49 and 7.56 (1H, two s's), 7.64 and 7.71 (1H, two s's). m/z 501 (MH$^+$).

DESCRIPTION 58
Ethyl 2-[5-(1,2,3-triazol-2-ylmethyl)thien-2-yl]-2-hydroxyiminoacetate The title compound was prepared from ethyl 2-[5-(1,2,3-triazol-2-ylmethyl)thien-2-yl]-2-oxoacetate (Description 55) by the procedure of Description 56. $v_{max}$ (tetrahydrofuran) 3254, 1742cm$^{-1}$. $\delta$(CDCl$_3$) 1.40 (3H, t, J 7.19 Hz), 4.36–4.49 (2H, m), 5.76 and 5.84 (2H, two s's), 7.05 and 7.15 (1H, two d's J 3.85 Hz), 7.66 (2H, s), 7.93 and 8.01 (1H, two d's, J 3.99 Hz). m/z 280 (M$^+$). [Found (HRMS): m/z 280.0632. Calc. for C$_{11}$H$_{12}$N$_4$O$_3$S; 280.0630].

DESCRIPTION 59
2-[5-(1,2,3-Triazol-2-ylmethyl)thien-2-yl]-N-[2-(acetylthiomethyl)-4-phenylbutyryl]glycine ethyl ester The title compound was prepared from ethyl 2-[5-(1,2,3-triazol-2-ylmethyl)thien-2-yl]-2-hydroxyiminoacetate (Description 58) by the procedure of Description 40 except that the eluent was 40% ethyl acetate in hexane. $v_{max}$ (CHCl$_3$) 3419, 1740 and 1684cm$^{-1}$. $\delta$(CDCl$_3$) 1.27 (3H, t, J 7.17 Hz), 1.79–2.11 (2H, m), 2.29 and 2.32 (3H, two s's), 2.30–2.77 (2H, m), 2.89–3.14 (2H, m), 4.17–4.83 (2H, m), 5.71 and 5.72 (2H, two s's), 5.77 and 5.81 (1H, two d's, J 7.43 Hz), 6.42 and 6.56 (1H, two d's, J 7.30 Hz), 7.57 and 7.63 (2H, two s's). m/z 501 (MH$^+$). [Found (HRMS): m/z 501.1629. Calc. for C$_{24}$H$_{29}$N$_4$O$_4$S$_2$; 501.1630].

DESCRIPTION 60
Ethyl 2-[5-(imidazolidin-2,4-dion-3-ylmethyl)thien-2-yl]-2-oxoacetate Potassium carbonate (414 mg) was added to a stirred solution of ethyl 2-(5-bromomethyl)thien-2-yl-2-oxoacetate (Description 49) (821 mg) and hydantoin (400 mg) in dimethylformamide (15 ml). The mixture was stirred at room temperature for 24 h and then partitioned between ethyl acetate and water. The organic phase was washed three times with water, then brine, dried over magnesium sulphate and evaporated. The product (340 mg) was isolated by column chromatography of the residue (Kieselgel:3:1 ethyl acetate:hexane). $v_{max}$(CHCl$_3$) 3463, 1783, 1772, 1666cm$^{-1}$. $\delta$(CDCl$_3$) 1.42 (3H, t, J 7.04 Hz), 4.03 (2H, s), 4.42 (2H, q, J 7.11 Hz), 4.88 (2H, s), 5.93 (1H, s), 7.18 (1H, d, J 3.93 Hz), 7.99 (1H, d, J 3.95 Hz).

DESCRIPTION 61
Ethyl 2-[5-(imidazolidin-2,4-dion-3-ylmethyl)thien-2-yl]-2-hydroxyiminoacetate The title compound was prepared from ethyl 2-[5-(imidazolidin-2,4-dion-3-ylmethyl)thien-2-yl]-2-oxoacetate (Description 60) by the procedure of Description 56. $v_{max}$ (nujol) 3290, 1603 cm$^{-1}$. m/z 311 (M$^+$). [Found (HRMS): m/z 311.0578. Calc. for C$_{12}$H$_{13}$N$_3$O$_5$S; 311.0576].

DESCRIPTION 62
2-[5-(Imidazolidin-2,4-dion-3-ylmethyl)thien-2-yl]-N-[2-(acetylthiomethyl)-4-phenylbutyryl]glycine ethyl ester The title compound was prepared from ethyl 2-[5-(imidazolidin-2,4-dion-3-ylmethyl)thien-2-yl]-2-hydroxyiminoacetate (Description 61) by the procedure of Description 40 except that the eluent was 75% ethyl acetate in hexane. $v_{max}$ (CHCl$_3$) 3463, 3416, 3286, 1780, 1719, 1684 cm$^{-1}$.

DESCRIPTION 63
2-(4-Methoxybenzyl)thiophene

Butyllithium (12.5 ml of 1.6N in hexanes) was added to a stirred solution of thiophene (1.68 g) in dry tetrahydrofuran (80 ml). The mixture was stirred at room temperature for 0.5 h and then a solution of 4-methoxybenzylbromide (2.62 g) in tetrahydrofuran (10 ml) was added dropwise. The mixture was stirred for 1 h and then acetic acid (1.2 ml) was added and the solvent evaporated. The residue was partitioned between ethyl acetate and water, the organic phase was washed with water and brine dried over magnesium sulphate and evaporated. The product was isolated by column chromatography (Kieselgel:hexane). $\delta$(CDCl$_3$) 3.80 (3H, s), 4.10 (2H, s), 6.78–6.94 (4H, m), 7.13–7.20 (3H, m).

DESCRIPTION 64
Ethyl 5-(4-methoxybenzyl)thiophen-2-yl-2-oxoacetate

The title compound was prepared from 2-(4-methoxybenzyl)thiophene (Description 63) by the procedure of Description 38. $v_{max}$ (CHCl$_3$) 1731, 1658cm$^{-1}$. $\delta$ (CDCl$_3$) 1.40 (3H, t, J 7.01 Hz), 3.80 (3H, s), 4.13 (2H, s), 4.40 (2H, q, J 7.19 Hz), 6.83–6.89 (3H, m), 7.13–7.19 (2H, m), 7.96 (1H, d, J 3.94 Hz).

DESCRIPTION 65
Ethyl 5-(4-methoxybenzyl)thiophen-2-yl-2-hydroxyiminoacetate

The title compound was prepared from ethyl 5-(4-methoxybenzyl)thiophen-2-yl-2-oxoacetate (Description 64) by the procedure of Description 39. $v_{max}$ (CHCl$_3$) 3237, 1729cm$^{-1}$. $\delta$(CDCl$_3$) 1.40 (3H, t, J 7.14 Hz), 3.79 (3H, s), 4.12 (2H, s), 4.39 (2H, q, J 7.18 Hz), 6.82–6.88 (3H, m), 7.17 (2H, d, J 8.52 Hz), 7.94 (1H, d, J 4.00 Hz), 10.24 (1H, br s).

DESCRIPTION 66
2-[5-(4-methoxybenzyl)thien-2-yl]-N-[2-(acetylthiomethyl)-4-phenylbutyryl]glycine ethyl ester The title compound was prepared from ethyl 5-(4-methoxybenzyl)thiophen-2-yl-2-hydroxyiminoacetate (Description 65) by the procedure of Description 40. $v_{max}$ (CHCl$_3$) 3422, 1739 and 1683cm$^{-1}$. m/z 539 (M$^+$). [Found (HRMS): m/z 539.1806. Calc. for C$_{29}$H$_{33}$NO$_5$S$_2$; 539.1800].

DESCRIPTION 67
2-[(5-Benzyl)furan-2-yl]-N-[-2-(acetylthiomethyl)-3-phenylpropionyl]glycine ethyl ester The title compound was prepared from 2-(acetylthiomethyl)-3-phenylpropionic acid (US 4329495) and ethyl (5-benzyl)furan-2-yl-2-hydroxyiminoacetate (Description 42) by the procedure of Description 40. $v_{max}$ (CHCl$_3$) 3428, 1741 and 1683cm$^{-1}$. m/z 479 M$^+$). [Found (HRMS): m/z 479.1768. Calc. for C$_{27}$H$_{29}$NO$_5$S; 479.1766].

DESCRIPTION 68
Ethyl 2-(5-azidomethyl)thien-2-yl-2-oxoacetate

Sodium azide (150 mg) was added to a stirred solution of ethyl 2-(5-bromomethyl)thien-2-yl-2-oxoacetate (Description 49) (554 mg) in dimethylformamide (5 ml). The mixture was stirred at room temperature for 2 h and then partitioned between ethyl acetate and water. The organic phase was washed three times with water, then brine, dried over magnesium sulphate and evaporated. The title compound (362 mg) was isolated by column chromatography of the residue, using gradient elution (Kieselgel:10% going to 20% ethyl acetate in hexane). $v_{max}$ (CHCl$_3$), 2103, 1731, 1667cm$^{-1}$. δ (CDCl$_3$) 1.44 (3H, t, J 7.03 Hz), 4.44 (2H, q, J 7.15 Hz), 4.58 (2H, s), 7.12 (1H, d, J 3.91 Hz), 8.06 (1H, d, J 3.93 Hz). m/z 239 (M$^+$). [Found (HRMS): m/z 239.0368. Calc. for C$_9$H$_9$N$_3$O$_3$S 239.0365].

DESCRIPTION 69
Ethyl 2-[5-{4,5-di(methoxycarbonyl)triazol-1-ylmethyl}thien-2-yl]-2-oxoacetate A mixture of ethyl 2-(5-azidomethyl)thien-2-yl-2-oxoacetate (Description 68) (300 mg) and dimethyl acetylenedicarboxylate (0.154 ml) in toluene (10 ml) was heated at reflux for 2 h. A further portion of dimethyl acetylenedicarboxylate (0.1 ml) was added and reflux continued for a further 2 h. The solvent was evaporated and the title compound (479 mg) was isolated by column chromatography of the residue using gradient elution (Kieselgel:40% ethyl acetate in hexane going to ethyl acetate). $v_{max}$ (CHCl$_3$) 1732, 1671cm$^{-1}$; δ(CDCl$_3$) 1.42 (3H, t, J 7.24 Hz), 3.98 (3H, s), 4.00 (3H, s), 4.42 (3H, s), 6.05 (2H, s), 7.17 (1H d, J 3.93 Hz), 8.00 (1H, d, J 3.94 Hz); m/z 382 (MH$^+$) [Found (HRMS): m/z 382.0714. Calc for C$_{15}$H$_{16}$N$_3$O$_7$S 382.0709].

DESCRIPTION 70
Ethyl 2-[5-{4,5-di(methoxycarbonyl)triazol-1-ylmethyl}thien-2-yl]-2-hydroxyiminoacetate The title compound was prepared from ethyl 2-[5-{4,5-di-methoxy-carbonyl)triazol-1-ylmethyl}thien-2-yl]-2-oxoacetate (Description 69) by the procedure described in Description 56. $v_{max}$ (CHCl$_3$) 3286 and 1732cm$^{-1}$; δ (CDCl$_3$) 1.37–1.45 (3H, m), 3.97, 3.98, 3.99 and 4.00 (3H, four s's), 4.37–4.49 (2H, m), 5.98 and 6.05 (2H, two s's), 7.04–7.19 (m) with 7.94 (d J 4.00 Hz) and 8.01 (d J 3.95 Hz) (total of 2H), 9.16 and 9.80 (1H, two s's); m/z 396 (M$^+$).

DESCRIPTION 71
2-[5-{4,5-Di(methoxycarbonyl)triazol-1-ylmethyl}thien-2-yl]-N-[2-(acetylthiomethyl)-4-phenylbutyryl]glycine ethyl ester The title compound was prepared from ethyl 2-[5-{4,5-di(methoxycarbonyl)-triazol-1-ylmethyl)thien-2-yl]-2-hydroxyiminoacetate (Description 70) by the procedure described in Description 40, except that the eluent used was 50% ethyl acetate in hexane. $v_{max}$(CHCl$_3$) 3417, 1735 and 1684cm$^{-1}$; δ(CDCl$_3$) 1.25–1.31 (3H, m), 1.80–2.11 (2H, m), 2.30 and 2.33 (3H, two s's), 2.30–2.75 (3H, m), 2.97–3.14 (2H, m), 3.93, 3.95, 3.97 and 3.98 (6H, four s's), 4.18–4.32 (2H, m), 5.76 and 5.79 (1H, two d's J 7.31 Hz), 5.94 and 5.95 (2H, two s's), 6.47 and 6.60 (1H, two d's J 7.29 Hz), 6.92–7.31 (7H, m); m/e 617 (MH$^+$).

DESCRIPTION 72
Ethyl 2-[5-(4-carboxamido-1,2,3-triazol-1-ylmethyl)thien-2-yl]-2-oxoacetate A mixture of ethyl 2-(5-azidomethyl)thien-2-yl-2-oxoacetate (Description 68) (355 mg) and propiolamide (113 mg) in toluene (20 ml) was heated at reflux for 7 h. The mixture was cooled and the solvent evaporated. The residue was dissolved in ethyl acetate and the solid filtered off and washed with ethyl acetate. The combined filtrates were evaporated and the title compound (199 mg) was obtained by column chromatography of the residue (Kieselgel; ethyl acetate as eluent). $v_{max}$ (CHCl$_3$) 3522, 3487, 3406, 3300, 3189, 1732, 1691, 1671cm$^{-1}$; δ(CDCl$_3$) 1.40 (3H, t, J 7.15 Hz), 4.40 (2H, q, J 7.23 Hz), 5.8–6.6 (2H, br), 6.18 (1H, s), 7.22 (1H, d, J 3.93 Hz), 7.97 (1H, d, J 3.94 Hz), 8.04 (1H, s); m/z 308 (M$^+$) [Found (HRMS), m/z 308.0582. Calc. for C$_{12}$H$_{12}$N$_4$O$_4$S; 308.0579].

DESCRIPTION 73
Ethyl 2-[5-(4-carboxamido-1,2,3-triazol-1-ylmethyl)thien-2-yl]-2-hydroximinoacetate The title compound was prepared from ethyl 2-[5-(4-carboxamido-1,2,3-triazol-1-ylmethyl)thien-2-yl]-2-oxoacetate (Description 72) by the procedure described in Description 56. $v_{max}$ (nujol) 3172, 1722, 1674, 1613cm$^{-1}$. δ (CD$_3$COCD$_3$) 1.33 and 1.34 (3H, two t's, J 7.08 Hz), 4.34 and 4.40 (2H, two q's, J 7.16 Hz), 6.17 and 6.25 (2H, two s's), 7.03 and 7.22 (1H, two d's, J 3.63 Hz), 7.16 and 7.69 (1H, two d's J 3.94 Hz), 7.33 (1H, br, s), 7.79 (1H, br, s), 8.21 (1H, s). m/z 323 (M$^+$) [Found (HRMS): m/z 323.0686. Calc. for C$_{12}$H$_{13}$N$_5$O$_4$S: 323.0688].

DESCRIPTION 74
2-[5-(4-Carboxamido-1,2,3-triazol-1-ylmethyl)thien-2-yl]-N-[2-(acetylthiomethyl)-4-phenylbutyryl]glycine ethyl ester The title compound was prepared from ethyl 2-[5-(4-caboxamido-1,2,3-triazol-1-ylmethyl)thien-2-yl]-2-hydroximinoacetate (Description 73) by the procedure described in Description 40. $v_{max}$ (CHCl$_3$) 3408, 3320, 3190, 1739, 1688cm$^{-1}$. δ(CDCl$_3$) 1.26 and 1.27 (3H, two t's, J 7.16 Hz), 1.76–2.05 (2H, m), 2.27 and 2.31 (3H, two s's), 2.35–2.75 (3H, m), 2.98–3.12 (2H, m), 4.17–4.29 (2H, m), 5.72 and 5.77 (1H, two d's, J 7.32 Hz), 6.06 and 6.08 (2H, two s's), 6.65 and 6.74 (1H, two d's, J 7.28 Hz), 6.87–6.88 (1H, m), 7.08–7.30 (6H, m), 7.93 and 8.02 (1H, two s's), m/z 544 (MH$^+$).

DESCRIPTION 75
Ethyl 2-[5-(4-methoxycarbonyl)triazol-1-ylmethylthien-2-yl]-2-oxoacetate and Ethyl 2-[5-(5-methoxycarbonyl)triazol-1-ylmethylthien-2-yl]-2-oxoacetate A mixture of ethyl 2-(5-azidomethyl)thien-2-yl-2-oxoacetate (Description 68) (645 mg) and methyl propiolate (0.27 ml) in toluene (20 ml) was heated at reflux for 1.5 h. A further portion of methyl propiolate (0.27 ml) was added and refluxing continued for a further 2 h. The solvent was evaporated and the products isolated by column chromatography of the residue using gradient elution (Kieselgel:1:1 ethyl acetate:hexane going to ethyl acetate). Ethyl 2-[5-(5-methoxycarbonyl)triazol-1-ylmethylthien-2-yl]-2- oxoacetate was eluted first; $v_{max}$ (CHCl$_3$) 1731 and 1669cm$^{-1}$. $\delta$(CDCl$_3$) 1.41 (3H, t, J 7.25 Hz), 3.95 (3H, s), 4.41 (2H, q, J 7.02 Hz), 6.13 (2H, s), 7.19 (1H, d, J 4.04 Hz), 7.99 (1H, d, J 3.98 Hz), 8.15 (1H, s), followed by ethyl 2-[5-(4-methoxycarbonyl)triazol-1-ylmethylthien-2-yl]-2-oxoacetate; $v_{max}$ (CHCl$_3$) 1731 and 1672cm$^{-1}$. $\delta$ (CDCl$_3$) 1.42 (3H, t, J 7.24 Hz), 3.94 (3H, s), 4.42 (2H, q, J 7.02 Hz), 5.82 (2H, s), 7.17 (1H, d, J 3.94 Hz), 8.05 (1H, d, J 3.93 Hz), 8.14 (1H, s).

DESCRIPTION 76
Ethyl 2-[5-(4-methoxycarbonyl)triazol-1-ylmethylthien-2-yl]-2-hydroxyiminoacetate The title compound was prepared from ethyl 2-[5-(4-methoxycarbonyl)triazol-1-ylmethylthien-2-yl]-2-oxoacetate (Description 75) by the procedure described in Description 56; $v_{max}$ (CHCl$_3$) 3555, 3282, 1731 and 1672cm$^{-1}$. $\delta$(CDCl$_3$) 1.41 and 1.42 (3H, two t's, J 7.02 Hz), 4.38–4.50 (2H, m), 5.73 and 5.82 (2H, two s's), 7.05–7.17 (1H, m), 7.98 and 8.05 (1H, two d's, J 3.94 Hz), 8.10 and 8.15 (1H, two s's). m/z 338 (M$^+$) [Found (HRMS): m/z 338.0682. Calc. for C$_{13}$H$_4$N$_4$O$_5$S 338.0685].

DESCRIPTION 77
2-[5-(4-Methoxycarbonyl)triazol-1-ylmethylthien-2-yl]-N-[2-(acetylthiomethyl)-4-phenylbutyryl]glycine ethyl ester The title compound was prepared from ethyl 2-[5-(4-methoxycarbonyl)triazol-1-ylmethylthien-2-yl]-2-hydroxyiminoacetate (Description 76) by the procedure described in Description 40, except that the eluent was 1:1 ethyl acetate:hexane; $v_{max}$ (CHCl$_3$) 3416, 1738, 1684cm$^{-1}$. $\delta$ (CDCl$_3$) 1.26–1.33 (3H, m), 1.77–2.13 (2H, m), 2.32 and 2.36 (3H, two s's), 3.30–2.75 (3H, m), 2.97–3.15 (2H, m), 3.92 and 3.93 (3H, two s's), 4.20–4.36 (2H, m), 5.68 and 5.70 (2H, two s's), 5.78 and 5.84 (1H, two d's, J 7.31 Hz), 6.56 and 6.67 (1H, two d's J 7.29 Hz), 6.97–7.31 (7H, m), 8.40–8.07 (1H, m).

DESCRIPTION 78
Ethyl 2-[5-(5-methoxycarbonyl)triazol-1-ylmethylthien-2-yl]-2-hydroxyiminoacetate The title compound was prepared from ethyl 2-[5-(5-methoxycarbonyl)triazol-1-ylmethylthien-2-yl]-2-oxoacetate (Description 75) by the procedure described in Description 56; $v_{max}$(tetrahydofuran) 3221 and 1738 cm$^{-1}$; m/z 338 (M$^+$), [Found (HRMS); m/z 338.0689. Calc. for C$_{13}$H$_{14}$N$_4$O$_5$S 338.0685].

DESCRIPTION 79
2-[5-(5-Methoxycarbonyl)triazol-1-ylmethylthien-2-yl]-N-[2-(acetylthiomethyl)-4-phenylbutyryl]glycine ethyl ester The title compound was prepared from ethyl 2-[5-(5-methoxycarbonyl)triazol-1-ylmethylthien-2-yl]-2-hydroxyiminoacetate (Description 78) by the procedure described in Description 40, except that the eluent was 1:1 ethyl acetate:hexane. $v_{max}$(CHCl$_3$) 3418, 1735, 1684cm$^{-1}$. $\delta$ (CDCl$_3$) 1.27 and 1.28 (3H, two t's, J 7.00 Hz), 1.70–2.10 (2H, m), 2.30 and 2.32 (3H, s), 2.30–2.75 (3H, m), 2.96–3.12 (2H, m), 3.89 and 3.95 (3H, two s's), 4.17–4.31 (2H, m), 5.75 and 5.79 (1H, two d's, J 6.31 Hz), 6.02 and 6.04 (2H, two s's), 6.43 and 6.56 (1H, two d's, J 7.31 Hz), 6.90–7.31 (7H, m), 8.08 and 8.11 (1H, two s's).

DESCRIPTION 80
N-(2'-R-acetylthiomethyl-4'-phenylbutanoyl)-p-(p-methoxy)-benzyloxy-D-phenylglycine methyl ester and N-(2'-S-acetylthiomethyl-4'-phenylbutanoyl)-p-(p-methoxy)-benzyloxy-D-phenylglycine methyl ester.

To a stirred solution of the p-hydroxyphenylglycine derivative (90 mg, 0.22 mmol), from Description 32, in dry tetrahydrofuran (2 ml) was added triphenyl phosphine (71 mg, 0.27 mmol) and p-methoxybenzyl alcohol (45 mg, 0.33 mmol) followed by diethyl azodicarboxylate (43 $\mu$l, 0.28 mmol). The resulting yellow solution was stirred at room temperature for 15 minutes before dilution with ethyl acetate. The organic layer was washed with water and dried (MgSO$_4$). The solvent was removed to afford a gum which was chromatographed on silica gel. Elution with 20% ethyl acetate in hexane gave diastereoisomer A as a gum (21 mg, 18%). $\delta_H$ (CDCl$_3$) 1.89 (1H, m), 2.02 (1H, m), 2.27 (3H, s), 2.40 (1H, m), 2.68 (2H, m), 3.01 (2H, d, J 8.0 Hz), 3.75 (3H, s), 3.82 (3H, s), 4.98 (2H, s), 5.49 (1H, d, J 6.8 Hz), 6.40 (1H, d, J 6.8 Hz), 6.96 (4H, overlapping d), 7.2–7.3 (9H, m) ppm. EIMS M$^+$535. This was followed by diastereoisomer B as a gum (24 mg, 21%). $\delta_H$ (CDCl$_3$) 1.90 (2H, m), 2.34 (3H, s), 2.50 (3H, m), 3.06 (2H, m), 3.74 (3H, s), 3.81 (3H, s), 4.97 (2H, s), 5.54 (1H, d, J 7.1 Hz), 6.56 (1H, d, J 7.1 Hz), 6.95 (4H, overlapping d), 7.0–7.3 (9H, m), ppm. EIMS M$^+$535.

DESCRIPTION 81
3'-dibenzofuranylglycine methyl ester

Dibenzofuranyl-3-carboxaldehyde (1.0 g, 5.1 mmol) was converted to the crude amino acid using essentially the method of Monianari et al. (Synthesis 1979, 26), but with some changes to the final purification. The crude solid material obtained after neutralization and evaporation of the water was stirred in methanol (35 ml), presaturated with hydrogen chloride gas, overnight. The methanol was removed under reduced pressure and the residue partitioned between ethyl acetate and an excess of saturated NaHCO3 solution. The organic layer was washed with water and dried. Removal of the solvent afforded the crude product. Chromatography on silica gel, eluting with ethyl acetate, gave desired product as a pale oil (41 mg, 3% over 2 stages). $\delta_H$(CDCl$_3$) 1.68 (2H, br s), 3.73 (3H, s), 4.81 (1H, s), 7.3–7.5 (5H, m), 7.95 (2H, m), ppm.

DESCRIPTION 82
N-(2'-SR-acetylthiomethyl-4'-phenylbutanoyl)-(3"-dibenzofuranyl) glycine methyl ester To a cooled (0°), stirred solution of 2-acetylthiomethyl-4-phenylbutanoic acid prepared as in Description 5 (41 mg, 0.16 mmol) in dry tetrahydrofuran (5 ml) containing dry dimethylformamide (1 drop), was added sodium hydride (7 mg of a 55% suspension in oil, 0.16 mmol). The reaction mixture was allowed to reach room temperature and stirring was continued for a further 15 mins. The suspension was then recooled (0°) and treated with oxalyl chloride (17 $\mu$l, 0.19 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) solution of (3'-dsibenzofuranyl) glycine methyl ester from Description 81 (41 mg, 0.16 mmol) in dry tetrahydrofuran (5 ml) was treated with triethylamine (22 $\mu$l, 0.16 mmol) followed by a solution of the above acid chloride in dry tetrahydrofuran (5 ml) added over 1 minute. The mixture was stirred at ambient temperature for 3 hours and then partitioned between ethyl acetate and 1M hydrochloric acid. The organic layer was washed with water and saturated brine and dried over anhydrous sodium sulphate. Evaporation of the solvent afforded crude product as an oil which was chromatographed on silica gel. Elution with 20% ethyl acetate in hexane afforded diastereoisomer A as an gum (15 mg, 19%). δ$_H$(CDCl$_3$) 1.93 (1H, m), 2.05 (1H, m), 2.24 (3H, s), 2.41 (1H, m), 2.7 (2H, m), 3.77 (3H, s), 4.38 (2H, q, J 7.2 Hz), 5.71 (1H, d, J 6.8 Hz), 6.63 (1H, d, J 6.8 Hz), 7.2–7.5 (10H, m), 7.95 (2H, m) ppm. This was followed by diastereoisomer B as an gum (16 mg, 21%). δ$_H$(CDCl$_3$) 1.87 (1H, m), 1.95 (1H, m), 2.35 (3H, s), 2.50 (3H, m), 3.09 (2H, m), 3.76 (3H, s), 5.76 (1H, d, J 6.9 Hz), 6.76 (1H, d, J 6.9 Hz), 7.0–7.5 (10H, m), 8.00 (2H, m) ppm. EIMS M$^+$489.

DESCRIPTION 83
N-(2'-R-acetylthiomethyl-4'-phenylbutanoyl)-p-(2"-furanylmethoxy)-D-phenylglycine methyl ester and N-(2'-S-acetylthiomethyl-4'-phenylbutanoyl)-p-(2"-furanylmethoxy)-D-phenylglycine methyl ester.

To a stirred solution of the p-hydroxyphenylglycine derivative (85 mg, 0.21 mmol), from Description 32, in dry tetrahydrofuran (2 ml) was added triphenyl phosphine (67 mg, 0.26 mmol) and furfuryl alcohol (26 μl, 0.30 mmol) followed by diethyl azodicarboxylate (42 μl, 0.27 mmol). The resulting yellow solution was stirred at room temperature for 15 minutes before dilution with ethyl acetate. The organic layer was washed with water and dried (MgSO$_4$). The solvent was removed to afford a gum which was chromatographed on silica gel. Elution with 20% ethyl acetate in hexane gave diastereoisomer A as a gum (27 mg, 26%). δ$_H$(CDCl$_3$) 1.89 (1H, m), 2.02 (1H, m), 2.27 (3H, s), 2.40 (1H, m), 2.68 (2H, m), 3.02 (2H, d, J 6.5 Hz), 3.75 (3H, s), 5.00 (2H, s), 5.49 (1H, d, J 6.8 Hz), 6.40 (3H, m), 6.98 (2H, d, J 8.7 Hz), 7.1–7.5 (8H, m) ppm. EIMS M$^+$495. This was followed by diastereoisomer B as a gum (30 mg, 30%). δ$_H$(CDCl$_3$) 1.90 (2H, m), 2.33 (3H, s), 2.50 (3H, m), 3.06 (2H, m), 3.74 (3H, s), 4.99 (2H, s), 5.55 (1H, d, J 7.0 Hz), 6.4–6.6 (3H, overlapping m), 7.0–7.5 (10H, m), ppm. EIMS M$^+$495.

DESCRIPTION 84
N-(2'-acetylthiomethyl-4'-phenylbutanoyl)-p-(p-acetoxy)-benzyloxy-D-phenylglycine methyl ester and N-(2'-S-acetylthiomethyl-4'-phenylbutanoyl)-p-(p-acetoxy)-benzyloxy-D-phenylglycine methyl ester.

To a stirred solution of the p-hydroxyphenylglycine derivative (138 mg, 0.33 mmol), from Description 32, in dry tetrahydrofuran (2 ml) was added triphenyl phosphine (108 mg, 0.41 mmol) and p-acetoxybenzyl alcohol (55 mg, 0.33 mmol) followed by diethyl azodicarboxylate (67 μl, 0.43 mmol). The resulting yellow solution was stirred at room temperature for 15 minutes before dilution with ethyl acetate. The organic layer was washed with water and dried (MgSO$_4$). The solvent was removed to afford a gum which was chromatographed on silica gel. Elution with 25% ethyl acetate in hexane gave diastereoisomer A as a gum (65 mg, 35%). δ$_H$ (CDCl$_3$) 1.89 (1H, m), 2.02 (1H, m), 2.26 (3H, s), 2.30 (3H, s), 2.40 (1H, m), 2.68 (2H, m), 3.01 (2H, d, J 7.7 Hz), 3.75 (3H, s), 5.04 (2H, s), 5.49 (1H, d, J 6.8 Hz), 6.48 (1H, d, J 6.8 Hz), 6.9–75 (13H, m) ppm. ESMS MH$^+$564. This was followed by diastereoisomer B as a gum (65 mg, 35%). δ$_H$(CDCl$_3$) 1.90 (2H, m), 2.28 (3H, s), 2.31 (3H, s), 2.50 (3H, m), 3.06 (2H, m), 3.74 (3H, s), 5.03 (2H, s), 5.54 (1H, d, J 7.0 Hz), 6.59 (1H, d, J 7.0 Hz), 6.9–7.5 (13H, m), ppm. ESMS MH$^+$564.

DESCRIPTION 85
N-(2'-acetylthiomethyl-4'-phenylbutanoyl)-p-(p-dimethylamino)-benzyloxy-D-phenylglycine methyl ester and N-(2'-S-acetylthiomethyl-4'-phenylbutanoyl)-p-(p-dimethylamino)-benzyloxy-D-phenylglycine methyl ester.

To a stirred solution of the p-hydroxyphenylglycine derivative (138 mg, 0.33 mmol), from Description 32, in dry tetrahydrofuran (2 ml) was added triphenyl phosphine (108 mg, 0.41 mmol) and p-dimethylaminobenzyl alcohol (50 mg, 0.33 mmol) followed by diethyl azodicarboxylate (67 μl, 0.43 mmol). The resulting yellow solution was stirred at room temperature for 15 minutes before dilution with ethyl acetate. The organic layer was washed with water and dried (MgSO$_4$). The solvent was removed to afford a gum which was chromatographed on silica gel. Elution with 25% ethyl acetate in hexane gave diastereoisomer A as a gum (33 mg). δ$_H$(CDCl$_3$) 1.89 (1H, m), 2.02 (1H, m), 2.26 (3H, s), 2.35 (1H, s), 2.68 (2H, m), 2.95 (6H, s), 3.01 (2H, d, J 7.7 Hz), 3.74 (3H, s), 4.94 (2H, s), 5.49 (1H, d, J 6.8 Hz), 6.38 (1H, d, J 6.8 Hz), 6.74 (2H, d, J 8.7 Hz), 6.97 (2H, d, J 8.7 Hz), 7.3 (9H, m) ppm. ESMS MH$^+$549. This was followed by diastereoisomer B as a gum (55 mg). δ$_H$(CDCl$_3$) 1.90 (2H, m), 2.33 (3H, s), 2.50 (3H, m), 2.95 (6H, s), 3.06 (2H, m), 3.73 (3H, s), 4.93 (2H, s), 5.54 (1H, d, J 7.0 Hz), 6.61 (1H, d, J 7.0 Hz), 6.73 (2H, d, J 8.8 Hz), 6.97 (2H, d J 8.7 Hz0, 7.0–7.3 (9H, m), ppm. ESMS MH$^+$549.

DESCRIPTION 86
N-(2'-R-acetylthiomethyl-4'-phenylbutanoyl)-p-(m-methoxycarbonyl)-benzyloxy-D-phenylglycine methyl ester and N-(2'-S-acetylthiomethyl-4'-phenylbutanoyl)-p-(m-methoxycarbonyl)-benzyloxy-D-phenylglycine methyl ester.

To a stirred solution of the p-hydroxyphenylglycine derivative (121 mg, 0.29 mmol), from Description 32, in dry tetrahydrofuran (2 ml) was added triphenylphosphine (95 mg, 0.36 mmol) and m-methoxycarbonylbenzyl alcohol (48 mg, 0.29 mmol) followed by diethyl azodicarboxylate (60 μl, 0.38 mmol). The resulting yellow solution was stirred at room temperature for 15 minutes before dilution with ethyl acetate. The organic layer was washed with water and dried (MgSO$_4$). The solvent was removed to afford a gum which was chromatographed on silica gel. Elution with 25% ethyl acetate in hexane gave diastereoisomer A as a gum (47 mg). δ$_H$(CDCl$_3$) 1.89 (1H, m), 2.05 (1H, m), 2.29 (3H, s), 2.40 (1H, m), 2.68 (2H, m), 3.05 (2H, m), 3.77 (3H, s), 3.96 (3H, s), 5.12 (2H, s), 5.52 (1H, d, J 6.9 Hz), 6.43 (1H, d, J 6.9 Hz), 6.98 (2H, d, J 8.8 Hz), 7.2–7.3 (7H, m), 7.50 (1H, dd, J 8 Hz), 7.64 (1H, d, 8 Hz), 8.03 (1H, d, J 7.8 Hz), 8.13 (1H, s) ppm. ESMS MNa$^+$587. This was followed by diastereoisomer B as a gum (64 mg). δ$_H$(CDCl$_3$) 1.89 (1H, m), 2.05 (1H, m), 2.29 (3H, s), 2.40 (1H, m), 2.68 (2H, m), 3.05 (2H, m), 3.77 (3H, s), 3.96 (3H, s), 5.12 (2H, s), 5.52 (1H, d, J 6.9 Hz), 6.43 (1H, d, J 6.9 Hz), 6.98 (2H, d, J 8.8 Hz), 7.2–7.3 (7H, m), 7.50 (1H, dd, J 8 Hz), 7.64 (1H, d, 8 Hz), 8.03 (1H, d, J 7.8 Hz), 8.13 (1H, s) ppm. ESMS MNa$^+$587

DESCRIPTION 87
N-(2'-R-acetylthiomethyl-4'-phenylbutanoyl)-p-(3,4-diacetoxy)-benzyloxy-D-phenylglycine methyl ester and N-(2'-S-acetylthiomethyl-4'-phenylbutanoyl)-p-(3,4-diacetoxy)-benzyloxy-D-phenylglycine methyl ester.

To a stirred solution of the p-hydroxyphenylglycine derivative (145 mg, 0.35 mmol), from Description 32, in dry tetrahydrofuran (2 ml) was added triphenylphosphine (114 mg, 0.44 mmol) and 3,4-diacetoxylbenzyl alcohol (78 mg, 0.35 mmol) followed by diethyl azodicarboxylate (72 μl, 0.46 mmol). The resulting yellow solution was stirred at room temperature for 15 minutes before dilution with ethyl acetate. The organic layer was washed with water and dried (MgSO$_4$). The solvent was removed to afford a gum which was chromatographed on silica gel. Elution with 33% ethyl acetate in hexane gave diastereoisomer A as a gum (81 mg). δ$_H$(CDCl$_3$) 1.89 (1H, m), 2.05 (1H, m), 2.29 (3H, s), 2.32 (6H, s), 2.40 (1H, m), 2.68 (2H,m), 3.05 (2H, d, J 7.1 Hz), 3.78 (3H, s), 5.12 (2H, s), 5.52 (1H, d, J 6.7 Hz), 6.46 (1H, d, J 6.7 Hz), 6.98 (2H, d, J 8.8 Hz), 7.2–7.4 (10H, m) ppm. ESMS MNa$^+$644. this was followed by diastereoisomer B as a gum (70 mg). $\delta_H$(CDCl$_3$) 1.89 (1H, m), 2.05 (1H, m), 2.35 (6H, s), 2.38 (3H, s), 2.4–2.7 (3H, m), 3.05 (2H, m), 3.78 (3H, s), 5.10 (2H, s), 5.58 (1H, d, J 6.7 Hz), 6.62 (1H, d, J 6.7 Hz), 6.98 (2H, d, J 8.8 Hz), 7.2–7.4 (10H, m) ppm. ESMS MNa$^+$644.

DESCRIPTION 88
N-(2'-R-acetylthiomethyl-4'-phenylbutanoyl)-p-(p-nitro)-benzyloxy-D-phenylglycine methyl ester and N-(2'-S-acetylthiomethyl-4'-phenylbutanoyl)-p-(p-nitro)-benzyloxy-D-phenylglycine methyl ester.

To a stirred solution of the p-hydroxyphenylglycine derivative (106 mg, 0.26 mmol), from Description 32, in dry tetrahydrofuran (2 ml) was added triphenylphosphine (85 mg, 0.32 mmol) and p-nitrobenzyl alcohol (39 mg, 0.26 mmol) followed by diethyl azodicarboxylate (53 µl, 0.34 mmol). The resulting yellow solution was stirred at room temperature for 15 minutes before dilution with ethyl acetate. The organic layer was washed with water and dried (MgSO$_4$). The solvent was removed to afford a gum which was chromatographed on silica gel. Elution with 25%–33% ethyl acetate in hexane gave diastereoisomer A as a gum (68 mg). $\delta_H$(CDCl$_3$) 1.89 (1H, m), 2.05 (1H, m), 2.27 (3H, s), 2.40 (1H, m), 2.68 (2H, m), 3.03 (2H, m), 3.74 (3H, s), 5.17 (2H, s), 5.52 (1H, d, J 6.9 Hz), 6.52 (1H, d, J 6.9 Hz), 6.95 (2H, d, J 8.7 Hz), 7.2–7.4 (7H, m) 7.60 (2H, d, J 8.7 Hz), 8.25 (2H, d, J 8.7 Hz) ppm. APCI MH$^+$551. This was followed by diastereoisomer B as a gum (43 mg). $\delta_H$ (CDCl$_3$) 1.90 (2H, m), 2.33 (3H, s), 2.4–2.6 (3H, m), 3.05 (2H, m), 3.74 (3H, s), 5.16 (2H, s), 5.55 (1H, d, J 6.7 Hz), 6.64 (1H, d, J 6.7 Hz), 6.98 (2H, d, J 8.8 Hz), 7.0–7.4 (7H, m)) 7.59 (2H, d, J 8.7 Hz), 8.25 (2H, d, J 8.7 Hz) ppm. APCI MH$^+$551.

DESCRIPTION 89
N-(2'-acetylthiomethyl-4'-phenylbutanoyl)-p-(4-pyridylmethoxy)-D-phenylglycine methyl ester To a stirred solution of the p-hydroxyphenylglycine derivative (118 mg, 0.28 mmol), from Description 32, in dry tetrahydrofuran (2 ml) was added triphenylphosphine (93 mg, 0.35 mmol) and 4-pyridylcarbinol (31 mg, 0.28 mmol) followed by diethyl azodicarboxylate (57 µl, 0.36 mmol). The resulting yellow solution was stirred at room temperature for 15 minutes before dilution with ethyl acetate. The organic layer was washed with water and dried (MgSO$_4$). The solvent was removed to afford a gum which was chromatographed on silica gel. Elution with ethyl acetate gave a mixture of diastereoisomers A and B as a gum (92 mg). $\delta_H$(CDCl$_3$) 1.85 (1H, m), 2.0 (1H, m), 2.22 and 2.28 (3H, s), 2.4–2.7 (3H, m), 3.0 (2H, m), 3.69 (3H, s), 5.02 and 5.03 (2H, s), 5.44 and 5.49 (1H, d, J 6.9 Hz), 6.37 and 6.52 (1H, d, J 6.9 Hz), 6.89 (2H, d, J 8.7 Hz), 7.0–7.3 (9H, m) 81.25 (2H, m) ppm. ESMS MH$^+$507.

DESCRIPTION 90
N-(2'-RS-acetylthiomethyl-4'-phenylbutanoyl)-p-(2-pyridylmethoxy)-D-phenylglycine methyl ester To a stirred solution of the p-hydroxyphenylglycine derivative (123 mg, 0.30 mmol), from Description 32, in dry tetrahydrofuran (2 ml) was added triphenylphosphine (97 mg, 0.37 mmol) and 2-pyridylcarbinol (32 mg, 0.30 mmol) followed by diethyl azodicarboxylate (60 µl, 0.39 mmol). The resulting yellow solution was stirred at room temperature for 15 minutes before dilution with ethyl acetate. The organic layer was washed with water and dried (MgSO$_4$). The solvent was removed to afford a gum which was chromatographed on silica gel. Elution with ethyl acetate/hexane (1:1) gave a mixture of diastereoisomers A and B as a gum (83 mg). $\delta_H$(CDCl$_3$) 1.85 (1H, m), 2.0 (1H, m), 2.27 and 2.33 (3H, s), 2.4–2.7 (3H, m), 3.0 (2H, m), 3.74 (3H, s), 5.20 (2H, s), 5.48 and 5.54 (1H, d, J 6.7 Hz), 6.39 and 6.55 (1H, d, J 6.7 Hz), 6.98 (2H, d, J 8.7 Hz), 7.0–7.3 (8H, m) 7.50 (1H, m), 7.72 (1H, m), 8.60 (1H, m) ppm. ESMS MNa$^+$529.

DESCRIPTION 91
N-(2'-RS-acetylthiomethyl-4'-phenylbutanoyl)-p-(3-pyridylmethoxy)-D-phenylglycine methyl ester To a stirred solution of the p-hydroxyphenylglycine derivative (114 mg, 0.28 mmol), from Description 32, in dry tetrahydrofuran (2 ml) was added triphenylphosphine (90 mg, 0.34 mmol) and 3-pyridylcarbinol (30 mg, 0.28 mmol) followed by diethyl azodicarboxylate (56 µl, 0.36 mmol). The resulting yellow solution was stirred at room temperature for 15 minutes before dilution with ethyl acetate. The organic layer was washed with water and dried (MgSO$_4$). The solvent was removed to afford a gum which was chromatographed on silica gel. Elution with ethyl acetate/hexane (1:1) gave a mixture of diastereoisomers A and B as a gum (104 mg). $\delta_H$(CDCl$_3$) 1.85 (1H, m), 2.0 (1H, m), 2.28 and 2.34 (3H, s), 2.4–2.7 (3H, m), 3.0 (2H, m), 3.74 (3H, s), 5.07 (2H, s), 5.50 and 5.55 (1H, d, J 6.7 Hz), 6.45 and 6.60 (1H, d, J 6.7 Hz), 6.97 (2H, d, J 8.7 Hz), 7.0–7.8 (9H, m) 8.58 (1H, m), 8.67 (1H, s) ppm. ESMS MH$^+$507.

DESCRIPTION 92
N-(2'-RS-acetylthiomethyl-4'-phenylbutanoyl)-p-(p-acetamido)-benzyloxy-D-phenylglycine methyl ester To a stirred solution of the p-hydroxyphenylglycine derivative (151 mg, 0.36 mmol), from Description 32, in dry tetrahydrofuran (2 ml) was added triphenylphosphine (119 mg, 0.45 mmol) and 4-acetamidobenzyl alcohol (60 mg, 0.36 mmol) followed by diethyl azodicarboxylate (74 µl, 0.47 mmol). The resulting yellow solution was stirred at room temperature for 15 minutes before dilution with ethyl acetate. The organic layer was washed with water and dried (MgSO$_4$). The solvent was removed to afford a gum which was chromatographed on silica gel. Elution with ethyl acetate gave a mixture of diastereoisomers A and B as a gum (101 mg). $\delta_H$(CDCl$_3$) 1.85 (1H, m), 2.0 (1H, m), 2.18 (3H, s), 2.26 and 2.33 (3H, s), 2.4–2.7 (3H, m), 3.0 (2H, m), 3.74 (3H, s), 5.00 (2H, s), 5.48 and 5.33 (1H, d, J 6.7 Hz), 6.43 and 6.59 (1H, d, J 6.7 Hz), 6.94 (2H, d, J 8.7 Hz), 7.0–7.5 (11H, m) ppm. ESMS MH$^+$563.

DESCRIPTION 93
N-(2'-RS-acetylthiomethyl-4'-phenylbutanoyl)-D-m-hydroxyphenylglycine methyl ester.

To a cooled (0°), stirred solution of 2-acetylthiomethyl-4-phenylbutanoic acid prepared as in Description 5, (0.50 g, 2.0 mmol) in dry tetrahydrofuran (10 ml) containing dry dimethylformamide (1 drop), was added sodium hydride (88 mg of a 55% suspension in oil, 2.0 mmol). The reaction mixture was allowed to reach room temperature and stirring was continued for a further 15 mins. The suspension was then recooled (0°) and treated with oxalyl chloride (210 µl, 2.4 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) solution of D-m-hydroxyphenylglycine methyl ester (435 mg, 2.0 mmol), prepared from D-m-hydroxyphenylglycine with hydrogen chloride in methanol as in Description 4, in dry tetrahydrofuran (10 ml) was treated with triethylamine (560 μl, 4.0 mmol) followed by a solution of the above acid chloride in dry tetrahydrofuran (5 ml) added over 1 minute. The mixture was stirred at ambient temperature for 3 hours and then partitioned between ethyl acetate and 1M hydrochloric acid. The organic layer was washed with water and saturated brine and dried over anhydrous sodium sulphate. Evaporation of the solvent afforded crude product as an oil which was chromatographed on silica gel. Elution with 33% ethyl acetate in hexane afforded the desired mixture of diastereoisomers as a pale gum (300 mg). $\delta_H$(CDCl$_3$) 1.89 (1H, m), 2.02 (1H, m), 2.28 and 2.34 (3H, s), 2.4–2.7 (3H, m), 3.1 (2H, m), 3.74 and 3.75 (3H, s), 5.51 and 5.55 (1H, d, J 6.9 Hz), 6.54 and 6.67 (1H, d, J 6.9 Hz), 6.8–7.3 (9H, m) ppm.

DESCRIPTION 94
N-(2'-R-acetylthiomethyl-4'-phenylbutanoyl)-m-(m-methoxycarbonyl)-benzyloxy-D-phenylglycine methyl ester and N-(2'-S-acetylthiomethyl-4'-phenylbutanoyl)-m-(m-methoxycarbonyl)-benzyloxy-D-phenylglycine methyl ester.

To a stirred solution of the m-hydroxyphenylglycine derivative (93 mg, 0.22 mmol), from Description 93, in dry tetrahydrofuran (2 ml) was added triphenylphosphine (72 mg, 0.28 mmol) and m-methoxycarbonylbenzyl alcohol (37 mg, 0.22 mmol) followed by diethyl azodicarboxylate (45 μl, 0.29 mmol). The resulting yellow solution was stirred at room temperature for 15 minutes before dilution with ethyl acetate. The organic layer was washed with water and dried (MgSO$_4$). The solvent was removed to afford a gum which was chromatographed on silica gel. Elution with 25% ethyl acetate in hexane gave diastereoisomer A as a gum (31 mg). $\delta_H$(CDCl$_3$) 1.89 (1H, m), 2.05 (1H, m), 2.25 (3H, s), 2.40 (1H, m), 2.68 (2H, m), 3.03 (2H, m), 3.74 (3H, s), 3.93 (3H, s), 5.10 (2H, s), 5.54 (1H, d, J 6.9 Hz), 6.48 (1H, d, J 6.9 Hz), 6.9–7.3 (9H, m), 7.50 (1H, dd, J 8 Hz), 7.64 (1H, d, 8 Hz), 8.00 (1H, dd, J 7.8 Hz), 8.11 (1H, s) ppm. ESMS MH$^+$564. This was followed by diastereoisomer B as a gum (33 mg). $\delta_H$(CDCl$_3$) 1.89 (1H, m), 2.00 (1H, m), 2.33 (3H, s), 2.4–2.6 (3H, m), 3.08 (2H, m), 3.73 (3H, s), 3.92 (3H, s), 5.08 (2H, s), 5.58 (1H, d, J 6.9 Hz), 6.64 (1H, d, J 6.9 Hz), 6.9–7.3 (9H, m), 7.44 (1H, dd, J 8 Hz), 7.60 (1H, d, 8 Hz), 8.00 (1H, d, J 7.8 Hz), 8.10 (1H, s) ppm. ESMS MH$^+$564.

DESCRIPTION 95
N-(2'-R-acetylthiomethyl-4'-phenylbutanoyl)-m-(p-methoxycarbonyl)-benzyloxy-D-phenylglycine methyl ester and N-(2'-S-acetylthiomethyl-4'-phenylbutanoyl)-m-(p-methoxycarbonyl)-benzyloxy-D-phenylglycine methyl ester.

To a stirred solution of the m-hydroxyphenylglycine derivative (92 mg, 0.22 mmol), from Description 93, in dry tetrahydrofuran (2 ml) was added triphenylphosphine (72 mg, 0.28 mmol) and p-methoxycarbonylbenzyl alcohol (37 mg, 0.22 mmol) followed by diethyl azodicarboxylate (45 μl, 0.29 mmol). The resulting yellow solution was stirred at room temperature for 15 minutes before dilution with ethyl acetate. The organic layer was washed with water and dried (MgSO$_4$). The solvent was removed to afford a gum which was chromatographed on silica gel. Elution with 25% ethyl acetate in hexane gave diastereoisomer A as a gum (30 mg). $\delta_H$(CDCl$_3$)1.89 (1H, m), 2.05 (1H, m), 2.25 (3H, s), 2.40 (1H, m), 2.68 (2H, m), 3.03 (2H, m), 3.74 (3H, s), 3.93 (3H, s), 5.13 (2H, s), 5.53 (1H, d, J 6.9 Hz), 6.48 (1H, d, J 6.9 Hz), 6.9–7.3 (9H, m), 7.50 (2H, d, J 8 Hz), 8.06 (2H, d, J 8 Hz)ppm. ESMS MH$^+$564. This was followed by diastereoisomer B as a gum (30 mg). $\delta_H$ (CDCl$_3$) 1.89 (1H, m), 2.00 (1H, m), 2.34 (3H, s), 2.4–2.6 (3H, m), 3.08 (2H, m), 3.73 (3H, s), 3.92 (3H, s), 5.10 (2H, s), 5.58 (1H, d, J 6.9Hz), 6.65 (1H, d, J 6.9 Hz), 6.9–7.3 (9H, m), 7.47 (2H, d, J 8 Hz), 8.10 (2H, d, J 8 Hz)ppm. ESMS MH$^+$564.

DESCRIPTION 96
N-(2'-R-acetylthiomethyl-4'-phenylbutanoyl)-p-(m-amino)-benzyloxy-D-phenylglycine methyl ester and N-(2'-S-acetylthiomethyl-4'-phenylbutanoyl)-p-(m-amino)-benzyloxy-D-phenylglycine methyl ester.

To a stirred solution of the p-hydroxyphenylglycine derivative (133 mg, 0.32 mmol), from Description 32, in dry tetrahydrofuran (2 ml) was added triphenyl phosphine (104 mg, 0.40 mmol) and m-aminobenzyl alcohol (40 mg, 0.32 mmol) followed by diethyl azodicarboxylate (65 μl, 0.42 mmol). The resulting yellow solution was stirred at room temperature for 15 minutes before dilution with ethyl acetate. The organic layer was washed with water and dried (MgSO$_4$). The solvent was removed to afford a gum which was chromatographed on silica gel. Elution with 50% ethyl acetate in hexane gave diastereoisomer A as a gum (36 mg). $\delta_H$(CDCl$_3$) 1.89 (1H, m), 2.02 (1H, m), 2.26 (3H, s), 2.35 (1H, s), 2.68 (2H, m), 3.02 (2H, d, J 7.7 Hz), 3.70 (2H, br s), 3.74 (3H, s), 4.97 (2H, s), 5.48 (1H, d, J 6.8 Hz), 6.39 (1H, d, J 6.8 Hz), 6.64 (1H, dd, J 7.7 and 2 Hz), 6.74 (1H, s), 6.79 (1H, d, J 7.6 Hz), 6.95 (2H, d, J 8.7 Hz), 7.2–7.3 (8H, m) ppm. ESMS MH$^+$ 521. This was followed by diastereoisomer B as a gum (27 mg). $\delta_H$(CDCl$_3$) 1.90 (2H, m), 2.33 (3H, s), 2.50 (3H, m), 3.06 (2H, m), 3.69 (2H, br s), 3.73 (3H, s), 4.97 (2H, s), 5.54 (1H, d, J 7.0 Hz), 6.55 (1H, d, J 7.0 Hz), 6.64 (1H, dd, J 7.5 and 2Hz), 6.74 (1H, s), 6.78 (1H, d, J 7.6 Hz), 6.95 (2H, d, J 8.7 Hz), 7.0–7.3 (8H, m), ppm. ESMS MH$^+$521.

DESCRIPTION 97
N-(2'-R-acetylthiomethyl-4'-phenylbutanoyl)-p-(p-dimethylamino)-phenethyloxy-D-phenylglycine methyl ester and N-(2'-S-acetylthiomethyl-4'-phenylbutanoyl)-p-(p-dimethylamino)-phenethyloxy-D-phenylglycine methyl ester.

To a stirred solution of the p-hydroxyphenylglycine derivative (116 mg, 0.28 mmol), from Description 32, in dry tetrahydrofuran (2 ml) was added triphenyl phosphine (92 mg, 0.35 mmol) and p-dimethylaminophenethyl alcohol (46 mg, 0.28 mmol) followed by diethyl azodicarboxylate (58 μl, 0.36 mmol). The resulting yellow solution was stirred at room temperature for 15 minutes before dilution with ethyl acetate. The organic layer was washed with water and dried (MgSO$_4$). The solvent was removed to afford a gum which was chromatographed on silica gel. Elution with 25% ethyl acetate in hexane gave diastereoisomer A as a gum (26 mg). $\delta_H$(CDCl$_3$) 1.89 (1H, m), 2.02 (1H, m), 2.26 (3H, s), 2.35 (1H, s), 2.68 (2H, m), 2.92 (6H, s), 3.00 (4H, m), 3.73 (3H, s), 4.10 (2H, t, J 7.3 Hz), 5.47 (1H, d, J 6.8 Hz), 6.36 (1H, d, J 6.8 Hz), 6.71 (2H, d, J 8.7 Hz), 6.88 (2H, d, J 8.7 Hz), 7.3 (9H, m) ppm. This was followed by diastereoisomer B as a gum (48 mg). $\delta_H$(CDCl$_3$) 1.90 (2H, m), 2.33 (3H, s), 2.50 (3H, m), 2.95 (6H, s), 3.06 (4H, m), 3.73 (3H, s), 4.20 (2H, m), 5.53 (1H, d, J 7.0 Hz), 6.53 (1H, d, J 7.0 Hz), 6.7–7.3 (13H, m), ppm.

DESCRIPTION 98
N-(2'-RS-acetylthiomethyl-4'-phenylbutanoyl)-p-(N-methyl-3-pyridiniummethoxy)-D-phenylglycine methyl ester iodide A solution of the 3-pyridyl compound (87 mg, 0.17 mmol) from Description 91 was dissolved in methanol (1 ml) and treated with methyl iodide (54 μl, 0.86 mmol). The reaction mixture was stoppered and warmed at 50° for 2 hours and then left overnight at room temperature. Evaporation of the solvent afforded the desired product as an oil (95 mg). $\delta_H$(CDCl$_3$) 1.86 (1H, m), 2.0 (1H, m), 2.32 and 2.34 (3H, s), 2.4–2.7 (3H, m), 3.0 (2H, m), 3.74 (3H, s), 4.58 (3H, s), 5.38 (2H, s), 5.46 and 5.51 (1H, d, J 6.7 Hz), 6.75 and 6.82 (1H, d, J 6.7 Hz), 7.0–7.3 (9H, m) 7.95 (1H, dd, J 6.0 and 6.0 Hz), 8.56 and 8.60 (1H, d, 6.0 and 6.0 Hz), 8.90 and 8.95 (1H, d, J 6.0 Hz), 9.46 and 9.50 (1H, s) ppm. ESMS M$^+$521.

DESCRIPTION 99

N-(2'-R-acetylthiomethyl-4'-phenylbutanoyl)-p-(p-benzyloxy)-benzyloxy-D-phenylglycine methyl ester and N-(2'-S-acetylthiomethyl-4'-phenylbutanoyl)-p-(p-benzyloxy)-benzyloxy-D-phenylglycine methyl ester.

To a stirred solution of the p-hydroxyphenylglycine derivative (117 mg, 0.28 mmol), from Description 32, in dry tetrahydrofuran (2 ml) was added triphenyl phosphine (92 mg, 0.35 mmol) and p-benzyloxybenzyl alcohol (60 mg, 0.28 mmol) followed by diethyl azodicarboxylate (57 μl, 0.36 mmol). The resulting yellow solution was stirred at room temperature for 15 minutes before dilution with ethyl acetate. The organic layer was washed with water and dried (MgSO$_4$). The solvent was removed to afford a gum which was chromatographed on silica gel. Elution with 33% ethyl acetate in hexane gave diastereoisomer A as a gum (48 mg). $\delta_H$(CDCl$_3$) 1.89 (1H, m), 2.02 (1H, m), 2.26 (3H, s), 2.36 (1H, m), 2.68 (2H, m), 3.02 (2H, d, J 8.0 Hz), 3.74 (3H, s), 4.97 (2H, s), 5.07 (2H, s), 5.49 (1H, d, J 6.8 Hz), 6.40 (1H, d, J 6.8 Hz), 6.96 (4H, overlapping d), 7.2–7.3 (14H, m) ppm. ESMS MH$^+$612. This was followed by diastereoisomer B as a gum (48 mg). $\delta_H$(CDCl$_3$) 1.90 (2H, m), 2.33 (3H, s), 2.50 (3H, m), 3.06 (2H, m), 3.73 (3H, s), 4.97 (2H, s), 5.06 (2H, s), 5.54 (1H, d, J 7.1 Hz), 6.56 (1H, d, J 7.1 Hz), 6.95 (4H, overlapping d), 7.0–7.3 (14H, m), ppm. ESMS MH$^+$612.

DESCRIPTION 100

N-(2'-R-acetylthiomethyl-4'-phenylbutanoyl)-p-(p-trifluoromethoxy)-benzyloxy-D-phenylglycine methyl ester and N-(2'-S-acetylthiomethyl-4'-phenylbutanoyl)-p-(p-trifluoromethoxy)-benzyloxy-D-phenylglycine methyl ester.

To a stirred solution of the p-hydroxyphenylglycine derivative (116 mg, 0.28 mmol), from Description 32, in dry tetrahydrofuran (2 ml) was added triphenyl phosphine (92 mg, 0.35 mmol) and p-(trifluoromethoxy)benzyl alcohol (54 mg, 0.28 mmol) followed by diethyl azodicarboxylate (57 μl, 0.36 mmol). The resulting yellow solution was stirred at room temperature for 15 minutes before dilution with ethyl acetate. The organic layer was washed with water and dried (MgSO$_4$). The solvent was removed to afford a gum which was chromatographed on silica gel. Elution with 25% ethyl acetate in hexane gave diastereoisomer A as a gum (60 mg). $\delta_H$(CDCl$_3$) 1.89 (1H, m), 2.02 (1H, m), 2.27 (3H, s), 2.36 (1H, m), 2.68 (2H, m), 3.02 (2H, d, J 8.0 Hz), 3.75 (3H, s), 5.05 (2H, s), 5.49 (1H, d, J 6.8 Hz), 6.44 (1H, d, J 6.8 Hz), 6.96 (2H, d, J 8.6 Hz), 7.2–7.3 (9H, m), 7.46 (2H, d, J 8.6 Hz) ppm. ESMS MH$^+$590. This was followed by diastereoisomer B as a gum (63 mg). $\delta_H$(CDCl$_3$) 1.90 (2H, m), 2.33 (3H, s), 2.50 (3H, m), 3.06 (2H, m), 3.73 (3H, s), 5.04 (2H, s), 5.55 (1H, d, J 7.0 Hz), 6.61 (1H, d, J 7.0 Hz), 6.95 (2H, d, J 8.6 Hz), 7.04 (2H, d), 7.2–7.3 (7H, m), 7.45 (2H, d, J 8.6 Hz) ppm. ESMS MH$^+$590.

EXAMPLE 1

N-(2'-mercaptomethyl-4'-phenylbutanoyl)-m-benzyl-phenylglycine (Diastereoisomer A)

The diastereoisomer A methyl ester (28 mg, 57.3 μmol) from Description 5 was suspended in methanol (0.5 ml) and treated with a solution of sodium sulphide nonahydrate (41 mg, 172 μmol) in water (0.5 ml). The suspension was stirred under argon for 30 minutes. The reaction mixture was then acidified by addition of 5M hydrochloric acid solution (5 drops) and diluted with ethyl acetate. The organic layer was washed with water and dried (MgSO$_4$). Removal of the solvent afforded the desired product as a crisp foam (24 mg). $\delta_H$(CDCl$_3$) 1.30 (1H, t, J 9.3 Hz), 1.85 (1H, m), 2.02 (1H, m), 2.30 (1H, m), 2.5–3.1 (4H, m), 3.97 (2H, s), 5.58 (1H, d, J 6.6 Hz), 6.48 (1H, d, J 6.6 Hz), 7.2 (14H, m) ppm. ESMS MH$^+$434.

EXAMPLE 2

N-(2'-mercaptomethyl-4'-phenylbutanoyl)-m-benzyl-phenylglycine (Diastereoisomer B)

the diastereoisomer B methyl ester (26 mg, 53.2 μmol) from Description 5 was suspended in methanol (0.5 ml) and treated with a solution of sodium sulphide nonahydrate (41 mg, 172 μmol) in water (0.5 ml). The suspension was stirred under argon for 30 minutes. The reaction mixture was then acidified by addition of 5M hydrochloric acid solution (5 drops) and diluted with ethyl acetate. The organic layer was washed with water and dried (MgSO$_4$). Removal of the solvent afforded the desired product as a crisp foam (22 mg). $\delta_H$(CDCl$_3$) 1.70 (1H, dd, J 10.0 & 7.6 Hz), 1.85 (1H, m), 1.95 (1H, m), 2.45 (3H, m), 2.83 (1H, m), 3.05 (1H, m), 3.98 (2H, s), 5.58 (1H, d, J 6.7 Hz), 6.50 (1H, d, J 6.7 Hz), 7.2 (14H, m) ppm. ESMS MH$^+$434.

EXAMPLE 3

N-(2'-mercaptomethyl-4'-phenylbutanoyl)-m-phenoxy-phenylglycine (Diastereoisomer A)

The diastereoisomer A methyl ester (141 mg, 0.29 mmol) from Description 7 was suspended in methanol (2 ml) and treated with a solution of sodium sulphide nonahydrate (207 mg, 0.86 mmol) in water (2 ml). The suspension was stirred under argon for 60 minutes. The reaction mixture was then acidified by addition of 5M hydrochloric acid solution (5 drops) and diluted with ethyl acetate. The organic layer was washed with water and dried (MgSO$_4$). Removal of the solvent afforded the desired product as a crisp foam (120 mg). EIMS M$^+$435.1499. Calculated C$_{25}$H$_{25}$NO$_4$S, 435.1504.

EXAMPLE 4

N-(2'-mercaptomethyl-4'-phenylbutanoyl)-m-phenoxy-phenylglycine (Diastereoisomer B)

The diastereoisomer B methyl ester (166 mg, 0.34 mmol) from Description 7 was suspended in methanol (2 ml) and treated with a solution of sodium sulphide nonahydrate (243 mg, 1.0 mmol) in water (2 ml). The suspension was stirred under argon for 30 minutes. The reaction mixture was then acidified by addition of 5M hydrochloric acid solution (5 drops) and diluted with ethyl acetate. The organic layer was washed with water and dried (MgSO$_4$). Removal of the solvent afforded the desired product as a crisp foam (130 mg). $\delta_H$(CDCl$_3$) 1.67 (1H, dd, J 9.7 & 7.8 Hz), 1.85 (1H, m), 1.95 (1H, m), 2.55 (3H, m), 2.83 (1H, m), 3.05 (1H, m), 5.59 (1H, d, J 6.8 Hz), 6.54 (1H, d, J 6.8 Hz), 7.0–7.4 (14H, m) ppm. EIMS M$^+$435.1508. Calculated C$_{25}$H$_{25}$NO$_4$S, 435.1504.

EXAMPLE 5
N-(2'-mercaptomethyl-4'-phenylbutanoyl)-m-(p-methoxybenzyl)-phenylglycine (Diastereoisomer A)

The diastereoisomer A methyl ester (67 mg, 0.129 mmol) from Description 11 was suspended in methanol (2 ml) and treated with a solution of sodium sulphide nonahydrate (93 mg, 0.39 mmol) in water (2 ml). The suspension was stirred under argon for 2 hours. The reaction mixture was then acidified by addition of 5M hydrochloric acid solution (5 drops) and diluted with ethyl acetate. The organic layer was washed with water and dried ($MgSO_4$). Removal of the solvent afforded the desired product as a crisp foam (22 mg). $\delta_H(CDCl_3)$ 1.31 (1H, dd, J 9.3 and 8.3 Hz), 1.85 (1H, m), 2.02 (1H, m), 2.30 (1H, m), 2.5–3.1 (4H, m), 3.77 (3H, s), 3.91 (2H, s), 5.57 (1H, d, J 6.6 Hz), 6.44 (1H, d, J 6.6 Hz), 6.81 (2H, d, J 8.6 Hz), 7.1–7.3 (11H, m) ppm.

EXAMPLE 6
N-(2'-mercaptomethyl-4'-phenylbutanoyl)-m-(p-methoxybenzyl)-phenylglycine (Diastereoisomer B)

The diastereoisomer B methyl ester (62 mg, 0.12 mmol) from Description 11 was suspended in methanol (2 ml) and treated with a solution of sodium sulphide nonahydrate (86 mg, 0.36 mmol) in water (2 ml). The suspension was stirred under argon for 2 hours. The reaction mixture was then acidified by addition of 5M hydrochloric acid solution (5 drops) and diluted with ethyl acetate. The organic layer was washed with water and dried ($MgSO_4$). Removal of the solvent afforded the desired product as a crisp foam (36 mg). $\delta_H(CDCl_3)$ 1.70 (1H, dd, J 9.8 & 7.7 Hz), 1.85 (1H, m), 1.95 (1H, m), 2.45 (3H, m), 2.83 (1H, m), 3.05 (1H, m), 3.75 (3H, s), 3.93 (2H, s), 5.58 (1H, d, J 6.9 Hz), 6.44 (1H, d, J 6.9 Hz), 6.78 (2H, d, J 8.6 Hz), 7.0–7.3 (11H, m) ppm.

EXAMPLE 7
N-(2'-mercaptomethyl-4'-phenylbutanoyl)-m-benzyloxy-phenylglycine

The diastereoisometric mixture (100 mg, 0.20 mmol) from Description 13 was suspended in methanol (2 ml) and treated with a solution of sodium sulphide nonahydrate (172 mg, 0.72 mmol) in water (2 ml). The suspension was stirred under argon for 2 hours. The reaction mixture was then acidified by addition of 5M hydrochloric acid solution (5 drops) and diluted with ethyl acetate. The organic layer was washed with water and dried ($MgSO_4$). Removal of the solvent afforded the desired product as a crisp foam (88 mg). $\delta_H(CDCl_3)$ 1.38 (0.5H, t, J 8.5 Hz), 1.72 (0.5H, dd, J 9.9 and 7.3 Hz), 1.8–2.0 (2H, m), 2.30–3.0 (5H, m), 5.05 (2H, s), 5.58 (1H, d, J 6.8 Hz), 6.48 and 6.51 (1H, d, J 6.8 Hz), 7.0–7.4 (14H, m) ppm. ESMS $MH^+450$.

EXAMPLE 8
N-(2'-mercaptomethyl-4'-phenylbutanoyl)-m-(p-hydroxybenzyl)-phenylglycine The mixture of diastereoisomeric methyl esters (50 mg, 0.10 mmol) from Description 17 was suspended in methanol (1 ml) and treated with a solution of sodium sulphide nonahydrate (96 mg, 0.40 mmol) in water (1 ml). The suspension was stirred under argon for 1 hour. The reaction mixture was then acidified by addition of 5M hydrochloric acid solution (5 drops) and diluted with ethyl acetate. The organic layer was washed with water and dried ($MgSO_4$). Removal of the solvent afforded the desired product as a crisp foam (46 mg). $\delta_H(CD_3OD)$ 1.85 (2H, m), 2.5–2.8 (5H, m), 3.88 (2H, s), 5.49 (1H, s), 6.68 (2H, m), 7.0–7.3 (11H, m) ppm. EIMS $M^+449.1657$. Calculated for $C_{26}H_{27}NO_4S$; 449.1661.

EXAMPLE 9
N-(2'-mercaptomethyl-4'-phenylbutanoyl)-(1-fluorenyl) glycine

The mixture of diastereoisomeric methyl esters (88 mg, 0.18 mmol) from Description 21 was suspended in methanol (2 ml) and treated with a solution of sodium sulphide nonahydrate (173 mg, 0.72 mmol) in water (2 ml). The suspension was stirred under argon for 1 hour. The reaction mixture was then acidified by addition of 5M hydrochloric acid solution (10 drops) and diluted with ethyl acetate. The organic layer was washed with water and dried ($MgSO_4$). Removal of the solvent afforded the desired product as a crisp foam (80 mg). $\delta_H(CDCl_3)$ 1.32 and 1.74 (1H, dd, J 9.8 and 7.8 Hz), 1.8–2.0 (2H, m), 2.3–3.1 (5H, m), 4.10 (2H, s), 5.88 and 5.91 (1H, d, J 6.8 Hz), 6.58 and 6.63 (1H, d, J 6.8 Hz), 7.0–7.8 (12H, m) ppm. EIMS $M^+449.1657$. Calculated for $C_{26}H_{27}NO_4S$; 449.1661.

EXAMPLE 10
N-(2'-mercaptomethyl-4'-phenylbutanoyl)-o-phenoxy-phenylglycine (Diastereoisomer A)

The diastereoisomer A methyl ester (41 mg, 0.083 mmol) from Description 25 was suspended in methanol (2 ml) and treated with a solution of sodium sulphide nonahydrate (80 mg, 0.33 mmol) in water (2 ml). The suspension was stirred under argon for 2 hours. The reaction mixture was then acidified by addition of 5M hydrochloric acid solution (5 drops) and diluted with ethyl acetate. The organic layer was washed with water and dried ($MgSO_4$). Removal of the solvent afforded the desired product as a crisp foam (37 mg). $\delta_H(CDCl_3)$ 1.28 (1H, dd, J 9.5 and 7.9 Hz), 1.82 (1H, m), 2.02 (1H, m), 2.25 (1H, m), 2.5–2.8 (4H, m), 5.94 (1H, d, J 8.0 Hz), 6.70 (1H, d, J 8.0 Hz), 6.84 (1H, d, J 8.3 Hz), 7.1–7.3 (13H, m) ppm. EIMS $M^+435.1512$. Calculated for $C_{25}H_{25}NO_4S$, 435.1504.

EXAMPLE 11
N-(2'-mercaptomethyl-4'-phenylbutanoyl)-o-phenoxy-phenylglycine (Diastereoisomer B)

The diastereoisomer B methyl ester (50 mg, 0.10 mmol) from Description 25 was suspended in methanol (2 ml) and treated with a solution of sodium sulphide nonahydrate (98 mg, 0.41 mmol) in water (2 ml). The suspension was stirred under argon for 2 hours. The reaction mixture was then acidified by addition of 5M hydrochloric acid solution (5 drops) and diluted with ethyl acetate. The organic layer was washed with water and dried ($MgSO_4$). Removal of the solvent afforded the desired product as a crisp foam (44 mg). $\delta_H(CDCl_3)$ 1.66 (1H, dd, J 9.8 & 7.7 Hz), 1.8–2.8 (7H, m), 5.96 (1H, d, J 7.8 Hz), 6.69 (1H, d, J 7.8 Hz), 6.89 (1H, d, J 8.2 Hz), 6.9–7.5 (13H, m) ppm. EIMS $M^+435.1512$. Calculated for $C_{25}H_{25}NO_4S$, 435.1504.

EXAMPLE 12
N-(2'-mercaptomethyl-4'-phenylbutanoyl)-p-phenoxy-phenylglycine (Diastereoisomer A)

The diastereoisomer A methyl ester (57 mg, 0.116 mmol) from Description 27 was suspended in methanol (2 ml) and treated with a solution of sodium sulphide nonahydrate (111 mg, 0.46 mmol) in water (2 ml). The suspension was stirred under argon for 3 hours. The reaction mixture was then acidified by addition of 5M hydrochloric acid solution (10 drops) and dliuted with ethyl acetate. The organic layer was washed with water and dried ($MgSO_4$). Removal of the solvent afforded the desired product as a crisp foam (52 mg). $\delta_H(CDCl_3)$ 1.37 (1H, dd, J 9.2 and 8.3 Hz), 1.82 (1H, m), 2.02 (1H, m), 2.30 (1H, m), 2.6–2.9 (4H, m), 5.58 (1H, d, J 6.5 Hz), 6.47 (1H, d, J 6.5 Hz), 7.0–7.4 (14H, m) ppm.

FABMS MH+436.1583. Calculated for $C_{25}H_{25}NO_4S$, 435.1504.

EXAMPLE 13
N-(2'-mercaptomethyl-4'-phenylbutanoyl)-p-phenoxy-phenylglycine (Diastereoisomer B)

The diastereoisomer B methyl ester (60 mg, 0.122 mmol) from Description 27 was suspended in methanol (2 ml) and treated with a solution of sodium sulphide nonahydrate (117 mg, 0.49 mmol) in water (2 ml). The suspension was stirred under argon for 3 hours. The reaction mixture was then acidified by addition of 5M hydrochloric acid solution (10 drops) and diluted with ethyl acetate. The organic layer was washed with water and dried ($MgSO_4$). Removal of the solvent afforded the desired product as a crisp foam (56 mg). $\delta_H(CDCl_3)$ 1.71 (1H, dd, J 9.7 & 7.8 Hz), 1.85 (1H, m), 1.95 (1H, m), 2.35 (1H, m), 2.55 (3H, m), 2.83 (1H, m), 5.60 (1H, d, J 6.6 Hz), 6.62 (1H, d, J 6.6 Hz), 7.0–7.4 (14H, m)ppm.

EXAMPLE 14
N-(2'-mercaptomethyl-4'-phenylbutanoyl)-m-(p-methoxyphenoxy)-phenylglycine (Diastereoisomer A)

The diastereoisomer A methyl ester (72 mg, 0.138 mmol) from Description 29 was suspended in methanol (2 ml) and treated with a solution of sodium sulphide nonahydrate (133 mg, 0.55 mmol) in water (2 ml). The suspension was stirred under argon for 3 hours. The reaction mixture was then acidified by addition of 5M hydrochloric acid solution (10 drops) and diluted with ethyl acetate. The organic layer was washed with water and dried ($MgSO_4$). Removal of the solvent afforded the desired product as a crisp foam (65 mg). $\delta_H(CDCl_3)$ 1.35 (1H, dd, J 9.2 and 8.3 Hz), 1.82 (1H, m), 2.02 (1H, m), 2.30 (1H, m), 2.6–2.9 (4H, m), 3.81 (3H, s), 5.56 (1H, d, J 6.6 Hz), 6.48 (1H, d, J 6.6 Hz), 6.9–7.3 (13H, m) ppm. EIMS M+465.1621. Calculated $C_{26}H_{27}NO_5S$, 465.1610.

EXAMPLE 15
N-(2'-mercaptomethyl-4'-phenylbutanoyl)-m-(p-methoxyphenoxy)-phenylglycine (Diastereoisomer B)

The diastereoisomer B methyl ester (166 mg, 0.34 mmol) from Description 29 was suspended in methanol (2 ml) and treated with a solution of sodium sulphide nonahydrate (243 mg, 1.0 mmol) in water (2 ml). The suspension was stirred under argon for 30 minutes. The reaction mixture was then acidified by addition of 5M hydrochloric acid solution (5 drops) and diluted with ethyl acetate. The organic layer was washed with water and dried ($MgSO_4$). Removal of the solvent afforded the desired product as a crisp foam (130 mg). $\delta_H(CDCl_3)$ 1.67 (1H, dd, J 9.8 & 7.8 Hz), 1.85 (1H, m), 1.95 (1H, m), 2.35 (1H, m), 2.55 (3H, m), 2.83 (1H, m), 3.78 (3H, s), 5.57 (1H, d, J 6.7 Hz), 6.65 (1H, d, J 6.7 Hz), 6.9–7.3 (13H, m) ppm. EIMS M+465.1597. Calculated $C_{26}H_{27}NO_5S$, 465.1610.

EXAMPLE 16
N-(2'-mercaptomethyl-4'-phenylbutanoyl)-(N-Ethyl-3-carbazolyl)glycine (Diastereoisomer A)

The diastereoisomer A methyl ester (26 mg, 0.05 mmol) from Description 31 was suspended in methanol (2 ml) and treated with a solution of sodium sulphide nonahydrate (48 mg, 0.20 mmol) in water (2 ml). The suspension was stirred under argon for 3 hours. The reaction mixture was then acidified by addition of 5M hydrochloric acid solution (10 drops) and diluted with ethyl acetate. The organic layer was washed with water and dried ($MgSO_4$). Removal of the solvent afforded the desired product as a crisp foam (23 mg). $\delta_H$ ($CDCl_3$) 1.40 (3H, t, J 7.1 Hz), 182 (1H, m), 2.02 (1H, m), 2.30 (1H, m), 2.6–2.8 (4H, m), 4.32 (2H, q, J 7.1 Hz), 5.78 (1H, d, J 7.0 Hz), 6.61 (1H, d J 7.0 Hz), 7.0–7.5 (10H, m) 8.18 (2H, m) ppm. EIMA M+ 460.1823. Calculated $C_{27}H_{28}N_2O_3S$, 460.1821.

EXAMPLE 17
N-(2'-mercaptomethyl-4'-phenylbutanoyl)-(N-Ethyl-3-carbazolyl)glycine (Diastereoisomer B)

The diastereoisomer b methyl ester (28 mg, 0.054 mmol) from Description 31 was suspended in methanol (2 ml) and treated with a solution of sodium sulphide nonahydrate (52 mg, 0.02 mmol) in water (2 ml). The suspension was stirred under argon for 3 hours. The reaction mixture was then acidified by addition of 5M hydrochloric acid solution (10 drops) and diluted with ethyl acetate. The organic layer was washed with water and dried ($MgSO_4$). Removal of the solvent afforded the desired product as a crisp foam (24 mg). $\delta_H$ ($CDCl_3$) 1.42 (3H, t, J 7.2 Hz), 1.79 (1H, dd, J 10.0 & 7.5 Hz), 1.85 (1H, m), 1.95 (1H, m), 2.3–2.8 (5H, m), 4.36 (2H, q, J 7.2 Hz), 5.80 (1H, d, J 6.6 Hz), 6.64 (1H, d, J 6.6 Hz), 7.0–7.5 (10 H, m) 8.10 (2H, m) ppm.

EXAMPLE 18
N-(2'-mercaptomethyl-4'-phenylbutanoyl)-p-benzyloxy-D-phenylglycine (Diastereoisomer A)

The diastereoisomer A methyl ester (32 mg, 0.063 mmol) from Description 33 was suspended in methanol (2 ml) and treated with a solution of sodium sulphide nonahydrate (61 mg, 0.25 mmol) in water (2 ml). The suspension was stirred under argon for 3 hours. The reaction mixture was then acidified by addition of 5M hydrochloric acid solution (10 drops) and diluted with ethyl acetate. The organic layer was washed with water and dried ($MgSO_4$). Removal of the solvent afforded the desired product as a crisp foam (28 mg). $\delta_H$ ($CDCl_3$) 1.36 (1H, dd, J 9.1 and 8.3 Hz), 1.82 (1H, m), 2.02 (1H, m), 2.29 (1H, m), 2.5–2.8 (4H, m), 5.05 (2H, s), 5.54 (1H, d, J 6.4 Hz), 6.49 (1H, d J 6.4 Hz), 6.9–7.4 (14H, m) ppm. ESMS MH+ 450.

EXAMPLE 19
N-(2'-mercaptomethyl-4'-phenylbutanoyl)-p-benzyloxy-D-phenylglycine (Diastereoisomer B)

The diastereoisomer B methyl ester (31 mg, 0.061 mmol) from Description 33 was suspended in methanol (2 ml) and treated with a solution of sodium sulphide nonahydrate (59 mg, 0.24 mmol) in water (2 ml). The suspension was stirred under argon for 3 hours. The reaction mixture was then acidified by addition of 5M hydrochloric acid solution (10 drops) and diluted with ethyl acetate. The organic layer was washed with water and dried ($MgSO_4$). Removal of the solvent afforded the desired product as a crisp foam (27 mg). $\delta_H$ ($CDCl_3$) 1.74 (1H, dd, J 10.0 & 7.5 Hz), 1.85 (1H, m), 1.95 (1H, m), 2.3–2.8 (5H, m), 5.06 (2H, s), 5.55 (1H, d, J 6.6 Hz), 6.51 (1H, d, J 6.6 Hz), 7.0–7.5 (14H, m) ppm ESMS MH+ 450.

EXAMPLE 20
N-(2'-mercaptomethyl-4'-phenylbutanoyl)-p-(2"-thienylmethoxy)-D-phenylglycine (Diastereoisomer A)

The diastereoisomer A methyl ester (50 mg, 0.10 mmol) from Description 34 was suspended in methanol (2 ml) and treated with a solution of sodium sulphide nonahydrate (94 mg, 0.40 mmol) in water (2 ml). The suspension was stirred under argon for 2 hours. The reaction mixture was then acidified by addition of 5M hydrochloric acid solution (10 drops) and diluted with ethyl acetate. The organic layer was washed with water and dried ($MgSO_4$). Removal of the solvent afforded the desired product as a crisp foam (45 mg).

$\delta_H$ (CDCl$_3$) 1.36 (1H, dd, J 9.1 and 8.3 Hz), 1.82 (1H, m), 2.02 (1H, m), 2.29 (1H, m), 2.5–2.8 (4H, m), 5.19 (2H, s), 5.55 (1H, d, J 6.6 Hz), 6.9–7.4 (12H, m) ppm ESMS MH$^+$ 456.

EXAMPLE 21
N-(2'-mercaptomethyl-4'-phenylbutanoyl)-p-(2"-thienylmethoxy)-D-phenylglycine (Diastereoisomer B)

The diastereoisomer B methyl ester (60 mg, 0.117 mmol) from Description 34 was suspended in methanol (2 ml) and treated with a solution of sodium sulphide nonahydrate (113 mg, 0.47 mmol) in water (2 ml). The suspension was stirred under argon for 2 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (54 mg). $\delta_H$ (CDCl$_3$) 1.74 (1H, dd, J 10.0 & 7.5 Hz), 1.85 (1H, m), 1.95 (1H, m), 2.3–2.8 (5H, m), 5.21 (2H, s), 5.56 (1H, d, J 6.6 Hz), 6.57 (1H, d, J 6.6 Hz), 7.0–7.5 (12H, m) ppm. ESMS MH$^+$ 456.

EXAMPLE 22
N-(2'-mercaptomethyl-4'-phenylbutanoyl)-p-(p-carboxy)-benzyloxy-D-phenylglycine (Diastereoisomer A)

The diastereoisomer a methyl ester (37 mg, 0.066 mmol) from Description 37 was suspended in methanol (3 ml) and treated with a solution of sodium sulphide nonahydrate (158 mg, 0.66 mmol) in water (2 ml). The suspension was stirred under argon for 3 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (34 mg). $\delta_H$ (MeOD) 1.85 (2H, m), 2.5–2.8 (5H, m), 5.19 (2H, s), 5.44 (1H, s), 7.03 (2H, d, J 8.8 Hz), 7.1–7.4 (6H, m), 7.56 (2H, d, J 8.2 Hz), 7.91 (1H, s), 8.04 (2H, d, J 8.2 Hz) ppm.

EXAMPLE 23
N-(2'-mercaptomethyl-4'-phenylbutanoyl)-p-(p-carboxy)-benzyloxy-D-phenylglycine (Diastereoisomer B)

The diastereoisomer B methyl ester (37 mg, 0.066 mmol) from Description 37 was suspended in methanol (3 ml) and treated with a solution of sodium sulphide nonahydrate (158 mg, 0.66 mmol) in water (2 ml). The suspension was stirred under argon for 3 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (34 mg). $\delta_H$ (MeOD) 1.84 (2H, m), 2.5–2.8 (5H, m), 5.19 (2H, s), 5.44 (1H, s), 7.0–8.0 (13H, m) ppm.

EXAMPLE 24
2-[(5-Benzyl)thien-2-yl]-N-[2-(mercaptomethyl)-4-phenylbutyryl]glycine A solution of sodium sulphide nonahydrate (464 mg) in water (3 ml) was added to a stirred solution of 2-[(5-benzyl)thien-2-yl]-N-[2-(acetylthiomethyl)-4-phenylbutyryl]glycine ethyl ester (Description 40) (330 mg) in methanol (3 ml) under argon. Further portions of methanol (totalling 5 ml) were added over 45 min. The mixture was stirred for a further 20 min. and then dilute hydrochloric acid (2 ml) was added and the mixture partitioned between ethyl acetate and water. The organic phase was washed with water and brined, dried over magnesium sulphate and evaporated. The product (209 mg) was isolated by column chromatography of the residue using gradient elution (Kieselgel:5% going to 10% methanol in chloroform). $v_{max}$ (CHCl$_3$) 3423, 3295, 1723 and 1674 cm$^{-1}$. $\delta$ (CD$_3$SOCD$_3$) 1.70–1.90 (2H, m), 2.43–2.70 (5H, m), 4.07 and 4.09 (2H, two s's), 5.43 (1H, d, J 7.77 Hz), 6.73–6.75 (1H, m), 6.88 and 6.91 (1H, two d's, J 3.42 Hz), 7.09–7.35 (10H, m). m/z 439 (M$^+$). [Found (HRMS): m/z 439.1281. Calc. for C$_{24}$H$_{25}$NO$_3$S$_2$: 439.1276].

EXAMPLE 25
2-[(5-Benzyl)furan-2-yl]-N-[2-(mercaptomethyl)-4-phenylbutyryl]glycine The title compound was prepared from 2-[(5-benzyl)furan-2-yl]-N-[2-(acetylthiomethyl)-4-phenylbutyryl]glycine ethyl ester (Description 43) by the procedure described in Example 24. $v_{max}$ (CHCl$_3$) 3430, 3294, 1727, 1662 cm$^{-1}$. $\delta$ (CD$_3$SOCD$_3$) 1.70–1.80 (2H, m), 2.40–2.74 (5H, m), 3.90 and 3.94 (2H, two s's), 5.30–5.35 (1H, m), 5.99–6.02 (1H, m), 6.22 and 6.26 (1H, two d's, J 4.10 Hz), 7.09–7.32 (10H, m), 8.48 (1H, d, J 6.98 Hz), m/z 423 (M$^+$). [Found (HRMS): 423.1503. Calc for C$_{24}$H$_{25}$NO$_4$S; 423.1504].

EXAMPLE 26
2-[5-(Tetrahydrofuran-3-ylmethyl)thien-2-yl]-N-[2-(mercaptomethyl)-4-phenylbutyryl]glycine The title compound was prepared from 2-[5-(tetrahydrofuran-3-ylmethyl)thien-2-yl]-N-[2-(acetylthiomethyl)-4-phenylbutyryl]glycine ethyl ester (Description 47) by the procedure described in Example 24 except that the eluent used was 10% methanol in dichloromethane. $v_{max}$ (CHCl$_3$) 3409, 3293, 1648 and 1603 cm$^{-1}$. $\delta$ (CD$_3$SOCD$_3$) 1.44–1.61 (1H, m), 1.70–1.82 (1H, m), 1.85–2.03 (1H, m), 2.30–2.80 (8H, m), 3.29–3.40 (2H, m), 3.53–3.76 (3H, m), 5.13 and 5.25 (1H, two d's, J 6.55 Hz), 5.70 and 5.77 (1H, two s's), 6.64 (1H, d, J 3.23 Hz), 6.74–6.84 (1H, m), 7.11–7.31 (5H, m), 7.87 and 8.12 (1H, two d's, J 6.68 Hz).

EXAMPLE 27
2-[5-(1-Tetrazolymethyl)thien-2-yl]-N-[2-(mercaptomethyl)-4-phenylbutyryl]glycine The title compound was prepared from 2-[5-(1-tetrazolylmethyl)thien-2-yl]-N-[2-(acetylthiomethyl)-4-phenylbutyryl]glycine ethyl ester (Description 52) by the procedure described in Example 24, except that the eluent used was 20% methanol in dichloromethane. $v_{max}$ (nujol), 3290, 1603 cm$^{-1}$. $\delta$ (CD$_3$SOCD$_3$) 1.68–1.86 (2H, m), 2.44–3.00 (6H, m), 5.25–5.31 (1H, m), 5.85 (2H, s), 6.88–7.31 (7H, m), 8.20–8.30 (1H, m), 9.49 (1H, s).

EXAMPLE 28
2-[5-(2-Tetrazolylmethyl)thien-2-yl]-N-[2-(mercaptomethyl)-4-phenylbutyryl]glycine The title compound was prepared from 2-[5-(2-tetrazolylmethyl)thien-2-yl]-N-[2-(acetylthiomethyl)-4-phenylbutyryl]glycine ethyl ester (Description 54) using the procedure described in Example 24 except that the eluent used was 10% methanol in dichloromethane. $v_{max}$ (CHCl$_3$) 3294 and 1646 cm$^{-1}$. $\delta$ (CD$_3$SOCD$_3$) 1.68–1.81 (2H, m), 2.42–2.73 (5H, m), 5.74–5.83 (1H, m), 6.09 (2H, s), 6.88–6.96 (1H, m), 7.05–7.31 (6H, m), 8.20–8.31 (1H, m), 8.94 and 8.98 (1H, two s's). m/z 530 (M-H)$^-$.

EXAMPLE 29
2-[5-(1,2,3-Triazol-1-ylmethyl)thien-2-yl]-N-[2-(mercaptomethyl)-4-phenylbutyryl]glycine The title compound was prepared from 2-[5-(1,2,3-triazol-1-ylmethyl)thien-2-yl]-N-[2-(acetylthiomethyl)-4- phenylbutyryl]glycine ethyl ester (Description 57) by the procedure described in Example 24 except that the eluent used was 20% methanol indichloromethane. $v_{max}$ (CHCl$_3$) 3292, 1731, 1648 and 1602 cm$^{-1}$. δ (CD$_3$SOCD$_3$) 1.70–1.82 (2H, m), 2.46–2.74 (5H, m), 5.22 (1H, d, J 6.85 Hz), 5.72 (2H, s), 6.85–7.31 (7H, m), 7.68 and 7.72 (1H, two s's), 8.11 and 8.14 (1H, two s's).

EXAMPLE 30
2-[5-(1,2,3-Triazol-2-ylmethyl)thien-2-yl]-N-[2-(mercaptomethyl)-4-phenylbutyryl]glycine The title compound was prepared from 2-[5-(1,2,3-triazol-2-yl)-thien-2-yl]-N-[2-(acetylthiomethyl)-4-phenylbutyryl]glycine ethyl ester by (Description 59) the procedure described in Example 29. $v_{max}$ (CHCl$_3$) 3289 and 1621 cm$^{-1}$. δ (CD$_3$SOCD$_3$) 1.68–1.83 (2H, m), 2.44–2.73 (5H, m), 5.20 (1H, d, J 6.87 Hz), 5.73 (2H, s), 6.83–6.94 (2H, m), 7.10–7.30 (5H, m), 7.74 and 7.78 (2H, two s's), 8.10 (1H, d, J 7.07 Hz). m/z 431 (MH$^+$).

EXAMPLE 31
2-[5-(Imidazolidin-2,4-dion-3-ylmethyl)thien-2-yl]-N-[2-(mercaptomethyl)-4-phenylbutyryl]glycine The title compound was prepared from 2-[5-(imidazolidin-2,4-dion-3-ylmethyl)thien-2-yl]-N-[2-(acetylthiomethyl)-4-phenylbutyryl]glycine ethyl ester (Description 62) by the procedure described in Example 27. $v_{max}$ (KBr) 3391, 1714 and 1638 cm$^{-1}$. m/z 479 (MNH$_4^+$).

EXAMPLE 32
2-[5-(4-methoxybenzyl)thien-2-yl]-N-[2-(mercaptomethyl)-4-phenylbutyryl]glycine The title compound was prepared from 2-[5-(4-methoxybenzyl)thien-2-yl]-N-[2-(acetylthiomethyl)-4-phenylbutyryl]glycine ethyl ester (Description 66) by the procedure described in Example 24. $v_{max}$ (CHCl$_3$) 3423, 1724 and 1674 cm$^{-1}$. m/z 469 (M$^+$).

EXAMPLE 33
2-[(5-Benzyl)furan-2-yl]-N-[2-(mercaptomethyl)-3-phenylpropionylglycine The title compound was prepared from 2-[(5-benzyl)furan-2-yl]-N-[2-(acetylthiomethyl)-3-phenylpropionyl]glycine ethyl ester (Description 67) by the procedure described in Example 24. $v_{max}$ (CHCl$_3$) 3433, 1728 and 1675 gm$^{-1}$. m/z 409 (M$^+$). [Found (HRMS): m/z 409.1352. Calc. for C$_{23}$H$_{23}$NO$_4$S; 409.1347].

EXAMPLE 34
2-[(5-Benzyl)thien-2-yl]-N-[2-(mercaptomethyl)-4-phenylbutyryl]glycine diastereomeric pairs The title compounds were separated as racemic diastereomeric pairs from the product of Example 24 by high pressure liquid chromatography.

EXAMPLE 35
2-[5-(4,5-Dicarboxytriazol-1-ylmethyl)thien-2-yl]-N-[2-(mercaptomethyl)-4-phenylbutyryl]glycine A solution of sodium sulphide nonahydrate (1.09 g) in water (6 ml) was added to a stirred solution of 2-[5-{4,5-di(methoxycarbonyl)triazol-1-ylmethyl}thien-2-yl]-N-[2-(acetylthiomethyl)-4-phenylbutyryl]glycine ethyl ester (Description 71) (400 mg) in methanol (6 ml). The mixture partitioned between ethyl acetate and water. The organic phase was washed with water and brine, dried over magnesium sulphate and evaporated. The residue was crystallised by trituration with ether and ethyl acetate, and the solid filtered off and washed with ether then dried under vacuum to give the title compound (92 mg). $v_{max}$ (nujol) 3294, 1732, 1643 cm$^{-1}$. m/z (M-H$^-$).

EXAMPLE 36
2-[5-(4-Carboxamidotriazol-1-ylmethyl)thien-2-yl]-N-[2-(mercaptomethyl)-4-phenylbutyryl]glycine The title compound was prepared from 2-[5-(4-Carboxamido-1,2,3-triazol-1-ylmethyl)thien-2-yl]-N-[2-(acetylthiomethyl)-4-phenylbutyryl]glycine ethyl ester (Description 74) by the procedure described in Example 35. $v_{max}$ (tetrahydrofuran) 3277, 3202, 1741 and 1692 cm$^{-1}$. δ (CD$_3$SOCD$_3$) 1.65–1.78 (2H, m), 2.42–2.71 (5H, m), 5.53–5.57 (1H, m), 6.06 (2H, s), 6.95–7.28 (7H, m), 7.89 (1H, s), 8.240 and 8.246 (1H, two s's), 8.28 (1H, s), 8.88 (1H, d, J 7.13 Hz), 13.04 (1H, br s).

EXAMPLE 37
2-[5-(4-Carboxytriazol-1-ylmethyl)thien-2-yl]-N-[2-(mercaptomethyl)-4-phenylbutyryl]glycine The title compound was prepared from ethyl 2-[5-(4-methoxycarbonyl)triazol-1-ylmethylthien-2-yl]-N-[2-(acetylthiomethyl)-4-phenylbutyryl]glycine ethyl ester (Description 77) by the procedure described in Example 35. $v_{max}$ (tetrahydrofuran) 1743, 1679 cm$^{-1}$. δ (CD$_3$SOCD$_3$) 1.70–1.88 (2H, m), 2.42–2.72 (6H, m), 5.57–5.63 (1H, m), 5.82 (2H, s), 6.98–7.29 (7H, m), 8.74 and 8.76 (1H, two s's), 8.87–9.10 (1H, m), 13.16 (1H, br s).

EXAMPLE 38
2-[5-(5-Carboxytriazol-1-ylmethyl)thien-2-yl]-N-[2-(mercaptomethyl)-4-phenylbutyryl]glycine The title compound was prepared from 2-[5-(5-methoxycarbonyl)triazol-1-ylmethyl)thien-2-yl]-N-[2-(acetylthiomethyl)-4-phenylbutyryl]glycine ethyl ester (Description 79) by the procedure described in Example 35. $v_{max}$ (tetrahydrofuran) 3286, 1740 and 1679 cm$^{-1}$. δ (CD$_3$SOCD$_3$) 1.62–1.82 (2H, m), 2.40–2.72 (3H, m), 5.54–5.59 (1H, m), 6.04 (2H, s), 6.94–7.27 (7H, m), 6.81 and 8.23 (1H, two s's), 8.80–9.03 (1H, m), 13.16 (1H, br s).

EXAMPLE 39
N-(2'-mercaptomethyl-4'-phenylbutanoyl)-p-(p-methoxy)-benzyloxy-D-phenylglycine (Diastereoisomer A)

The diastereoisomer A methyl ester (21 mg, 0.04 mmol) from Description 80 was suspended in methanol (3 ml) and treated with a solution of sodium sulphide nonahydrate (38 mg, 0.16 mmol) in water (2 ml). The suspension was stirred under argon for 3 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (19 mg). $δ_H$ (CDCl$_3$) 1.36 (1H, dd, J 9.2 and 8.3 Hz), 1.85 (1H, m), 2.0 (1H, m), 2.3–2.8 (5H, m), 3.82 (3H, s), 4.97 (2H, s), 5.54 (1H, d, J 6.4 Hz), 6.45 (1H, d, J 6.4 Hz), 6.9 (4H, overlapping d), 7.1–7.4 (9H, m) ppm. EIMS [M-H]$^-$ 478.1690. Calculated for C$_{27}$H$_{29}$NO$_5$S 478.1688.

EXAMPLE 40
N-(2'-mercaptomethyl-4'-phenylbutanoyl)-p-(p-methoxy)-benzyloxy-D-phenylglycine (Diastereoisomer B)

The diastereoisomer B methyl ester (24 mg, 0.045 mmol) from Description 80 was suspended in methanol (3 ml) and treated with a solution of sodium sulphide nonahydrate (43 mg, 0.18 mmol) in water (2 ml). The suspension was stirred under argon for 3 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (21 mg). δ$_H$ (CDCl$_3$) 1.74 (1H, dd, J 10.0 and 7.5 Hz), 1.85 (1H, m), 2.0 (1H, m), 2.3–2.8 (5H, m), 3.81 (3H, s), 4.98 (2H, s), 5.55 (1H, d, J 6.6 Hz),), 6.54 (1H, d, J 6.6 Hz), 6.9 (4H, overlapping d), 7.1–7.4 (9H, m) ppm. EIMS [M-H]$^-$ 478.1695. Calculated for C$_{27}$H$_{29}$NO$_5$S 478.1688.

EXAMPLE 41

N-(2'-mercaptomethyl-4'-phenylbutanoyl)-(3"-dibenzofuranyl) glycine (Diastereoisomer A)

The diastereoisomer a methyl ester (15 mg, 0.03 mmol) from Description 82 was suspended in methanol (2 ml) and treated with a solution of sodium sulphide nonahydrate (30 mg, 0.12 mmol) in water (2 ml). The suspension was stirred under argon for 3 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (12 mg). δ$_H$ (CDCl$_3$) 1.35 (1H, t, J 8.8 Hz), 1.85 (1H, m), 2.0 (1H, m), 2.3–2.8 (5H, m), 5.77 (1H, d, J 6.4 Hz),), 6.71 (1H, d, J 6.4 Hz), 7.1–7.6 (10H, m), 7.89 (1H, d, J 7.0 Hz), 8.04 (1H, s) ppm. EIMS M$^+$ 433.1355. Calculated for C$_{25}$H$_{23}$NO$_4$S 433.1348.

EXAMPLE 42

N-(2'-mercaptomethyl-4'-phenylbutanoyl)-(3"-dibenzofuranyl) glycine (Diastereoisomer B)

The diastereoisomer B methyl ester (16 mg, 0.033 mmol) from Description 82 was suspended in methanol (2 ml) and treated with a solution of sodium sulphide nonahydrate (30 mg, 0.13 mmol) in water (2 ml). The suspension was stirred under argon for 3 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (14 mg). δ$_H$ (CDCl$_3$) 1.73 (1H, dd, J 10.0 and 7.6 Hz), 1.85 (1H, m), 2.0 (1H, m), 2.3–2.8 (5H, m), 5.78 (1H, d, J 6.6 Hz),), 6.72 (1H, d, J 6.6 Hz), 7.0–7.6 (10H, m), 7.91 (1H, d, J 7.9 Hz), 8.03 (1H, s) ppm. EIMS M$^+$ 433.1347. Calculated for C$_{25}$H$_{23}$NO$_4$S 433.1348.

EXAMPLE 43

N-(2'-mercaptomethyl-4'-phenylbutanoyl)-p-(2"-furanylmethoxy)-D-phenylglycine (Diastereoisomer A)

The diastereoisomer a methyl ester (27 mg, 0.055 mmol) from Description 83 was suspended in methanol (2 ml) and treated with a solution of sodium sulphide nonahydrate (53 mg, 0.22 mmol) in water (2 ml). The suspension was stirred under argon for 3 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (24 mg). ESMS [M-H]$^-$ 438.

EXAMPLE 44

N-(2'-mercaptomethyl-4'-phenylbutanoyl)-p-(2"-furanylmethoxy)-D-phenylglycine (Diastereoisomer B)

The diastereoisomer B methyl ester (30 mg, 0.06 mmol) from Description 83 was suspended in methanol (2 ml) and treated with a solution of sodium sulphide nonahydrate (58 mg, 0.24 mmol) in water (2 ml). The suspension was stirred under argon for 3 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (27 mg). δ$_H$ (CDCl$_3$) 1.72 (1H, dd, J 10.0 and 7.6 Hz), 1.85 (1H, m), 2.0 (1H, m), 2.3–2.8 (5H, m), 4.98 (2H, s), 5.54 (1H, d, J 6.6 Hz),), 6.4 (2H, m), 6.54 (1H, d, J 6.6 Hz), 7.0–7.5 (10H, m) ppm. ESMS [M-H]$^-$ 438.

EXAMPLE 45

N-(2'-mercaptomethyl-4'-phenylbutanoyl)-p-(p-hydroxy)-benzyloxy-D-phenylglycine (Diastereoisomer A)

The diastereoisomer A methyl ester (79 mg, 0.14 mmol) from Description 84 was suspended in methanol (2 ml) and treated with a solution of sodium sulphide nonahydrate (168 mg, 0.70 mmol) in water (2 ml). The suspension was stirred under argon for 3 hours. The reaction mixture was then washed with ethyl acetate and the aqueous layer acidified by addition of 5M hydrochloric acid solution (10 drops) and then extracted with ethyl acetate. The organic layer was washed with water and dried (MgSO$_4$). Removal of the solvent afforded the desired product as a crisp foam (49 mg). δ$_H$ (CD$_3$OD) 1.85 (2H, m), 2.4–2.8 (5H, m), 2H, s), 5.38 (1H, m),), 6.7–6.9 (4H, m), 7.1–7.4 (9H, m) ppm ESMS MH$^+$ 466.

EXAMPLE 46

N-(2'-mercaptomethyl-4'-phenylbutanoyl)-p-(p-hydroxy)-benzyloxy-D-phenylglycine (Diastereoisomer B)

The diastereoisomer B methyl ester (65 mg, 0.115 mmol) from Description 84 was suspended in methanol (2 ml) and treated with a solution of sodium sulphide nonahydrate (138 mg, 0.58 mmol) in water (2 ml). The suspension was stirred under argon for 3 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (40 mg). δ$_H$ (CD$_3$OD) 1.8 (2H, m), 2.4–2.8 (5H, m), 4.93 (2H, s), 5.45 (1H, s),), 6.7–6.8 (4H, overlapping d), 7.1–7.4 (9H, m) ppm. ESMS MH$^+$ 466.

EXAMPLE 47

N-(2'-mercaptomethyl-4'-phenylbutanoyl)-p-(p-dimethylamino)-benzyloxy-D-phenylglycine (Diastereoisomer A)

The diastereoisomer A methyl ester (33 mg, 0.06 mmol) from Description 85 was suspended in methanol (3 ml) and treated with a solution of sodium sulphide nonahydrate (58 mg, 0.24 mmol) in water (2 ml). The suspension was stirred under argon for 3 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (27 mg, 93%). δ$_H$ (CD$_3$OD) 1.85 (2H, m), 2.4–2.8 (5H, m), 2.90 (6H, s), 4.91 (2H, s), 5.38 (1H, s),), 6.7–7.3 (13H, m) ppm. EIMS M$^+$ 492.

EXAMPLE 48

N-(2'-mercaptomethyl-4'-phenylbutanoyl)-p-(p-dimethylamino)-benzyloxy-D-phenylglycine (Diastereoisomer B)

The diastereoisomer B methyl ester (55 mg, 0.10 mmol) from Description 85 was suspended in methanol (2 ml) and treated with a solution of sodium sulphide nonahydrate (96 mg, 0.40 mmol) in water (2 ml). The suspension was stirred under argon for 3 hours. The reaction mixture was then washed with ethyl acetate and the aqueous layer acidified by addition of 5M hydrochloric acid solution (10 drops) and then extracted with ethyl acetate. The organic layer was washed with water and dried (MgSO$_4$). Removal of the solvent afforded the desired product as a crisp foam (25 mg). $\delta_H$ (CD$_3$OD) 1.8 (2H, m), 2.4–2.8 (5H, m), 2.93 (6H, s), 4.91 (2H, s), 5.38 (1H, s),), 6.7–7.3 (13H, m) ppm. EIMS M$^+$ 492.

EXAMPLE 49

N-(2'-mercaptomethyl-4'-phenylbutanoyl)-p-(m-carboxy)-benzyloxy-D-phenylglycine (Diastereoisomer A)

The diastereoisomer a methyl ester (47 mg, 0.08 mmol) from Description 86 was suspended in methanol (3 ml) and treated with a solution of sodium sulphide nonahydrate (100 mg, 0.42 mmol) in water (2 ml). The suspension was stirred under argon for 3 hours. The reaction mixture was then washed with ethyl acetate and the aqueous layer acidified by addition of 5M hydrochloric acid solution (10 drops) and then extracted with ethyl acetate. The organic layer was washed with water and dried (MgSO$_4$). Removal of the solvent afforded the desired product as a crisp foam (36 mg). $\delta_H$ (CDCl$_3$) 1.29 (1H, t, J 8.9 Hz), 1.78 (1H, m), 1.94 (1H, m), 2.23 (1H, m), 2.5–2.8 (4H, m), 5.05 (2H, s), 5.45 (1H, d, J 6.6 Hz), 6.42 (1H, d, J 6.6 Hz), 6.82 (2H, d, J 8.7 Hz), 7.2–7.4 (8H, m), 7.56 (1H, d, J 7.7 Hz), 7.94 (1H, d, J 7.7 Hz), 8.02 (1H, s) ppm. APCI [M–H]$^-$ 492.

EXAMPLE 50

N-(2'-mercaptomethyl-4'-phenylbutanoyl)-p-(m-carboxy)-benzyloxy-D-phenylglycine (Diastereoisomer B)

The diastereoisomer b methyl ester (64 mg, 0.11 mmol) from Description 86 was suspended in methanol (3 ml) and treated with a solution of sodium sulphide nonahydrate (136 mg, 0.57 mmol) in water (2 ml). The suspension was stirred under argon for 4 hours. The reaction mixture was then washed with ethyl acetate and the aqueous layer acidified by addition of 5M hydrochloric acid solution (10 drops) and then extracted with ethyl acetate. The organic layer was washed with water and dried (MgSO$_4$). Removal of the solvent afforded the desired product as a crisp foam (34 mg). $\delta_H$ (CDCl$_3$) 1.65 (1H, dd, J 10.0 and 7.7 Hz), 1.78 (1H, m), 1.94 (1H, m), 2.26 (1H, m), 2.5–2.8 (4H, m), 5.07 (2H, s), 5.46 (1H, d, J 6.5 Hz), 6.43 (1H, d, J 6.5 Hz), 6.83 (2H, d, J 8.7 Hz), 7.2–7.4 (8H, m), 7.56 (1H, d, J 7.7 Hz), 7.94 (1H, d, J 7.7 Hz), 8.02 (1H, s) ppm. APCI [M–H]$^-$ 492.

EXAMPLE 51

N-(2'-mercaptomethyl-4'-phenylbutanoyl)-p-(3,4-dihydroxy)-benzyloxy-D-phenylglycine (Diastereoisomer A)

The diastereoisomer A methyl ester (81 mg, 0.13 mmol) from Description 87 was suspended in methanol (2 ml) and treated with a solution of sodium sulphide nonahydrate (250 mg, 1.04 mmol) in water (2 ml). The suspension was stirred under argon for 3 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (67 mg). $\delta_H$ (CD$_3$OD) 1.85 (2H, m), 2.4–2.8 (5H, m), 4.91 (2H, s), 5.38 (1H, m),), 6.7–6.9 (4H, m), 7.1–7.4 (9H, m) ppm. ESMS MH$^+$ 466.

EXAMPLE 52

N-(2'-mercaptomethyl-4'-phenylbutanoyl)-p-(3,4-dihydroxy)-benzyloxy-D-phenylglycine (Diastereoisomer B)

The diastereoisomer B methyl ester (65 mg, 0.115 mmol) from Description 87 was suspended in methanol (2 ml) and treated with a solution of sodium sulphide nonahydrate (138 mg, 0.58 mmol) in water (2 ml). The suspension was stirred under argon for 3 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (40 mg). $\delta_H$ (CD$_3$OD) 1.8 (2H, m), 2.4–2.8 (5H, m), 4.93 (2H, s), 5.45 (1H, s),), 6.7–6.8 (4H, overlapping d), 7.1–7.4 (9H, m) ppm. ESMS MH$^+$ 466.

EXAMPLE 53

N-(2'-mercaptomethyl-4'-phenylbutanoyl)-p-(p-nitro)-benzyloxy-D-phenylglycine (Diastereoisomer A)

The diastereoisomer a methyl ester (68 mg) from Description 88 was suspended in methanol (3 ml) and treated with a solution of sodium sulphide nonahydrate (120 mg, 0.5 mmol) in water (2 ml). The suspension was stirred under argon for 3 hours. The reaction mixture was then washed with ethyl acetate and the aqueous layer acidified by addition of 5M hydrochloric acid solution (10 drops) and then extracted with ethyl acetate. The organic layer was washed with water and dried (MgSO$_4$). Removal of the solvent afforded the desired product as a crisp foam (7 mg). $\delta_H$ (CDCl$_3$) 1.35 (1H, m), 1.85 (1H, m), 2.00 (1H, m), 2.30 (1H, m), 2.25–2.8 (4H, m), 5.16 (2H, s), 5.55 (1H, d, J 6.5 Hz), 6.48 (1H, d, J 6.5 Hz), 6.94 (2H, d, J 8.7 Hz), 7.1–7.4 (7H, m), 7.58 (2H, d, J 8.7 Hz), 8.25 (2H, d, J 8.7 Hz) ppm. APCI [M–H]$^-$ 493.

EXAMPLE 54

N-(2'-mercaptomethyl-4'-phenylbutanoyl)-p-(p-nitro)-benzyloxy-D-phenylglycine (Diastereoisomer B)

The diastereoisomer B methyl ester (43 mg, 0.08 mmol) from Description 88 was suspended in methanol (4 ml) and treated with a solution of sodium sulphide nonahydrate (75 mg, 0.31 mmol) in water (2 ml). The suspension was stirred under argon for 3 hours. The reaction mixture was then washed with ethyl acetate and the aqueous layer acidified by addition of 5M hydrochloric acid solution (10 drops) and then extracted with ethyl acetate. The organic layer was washed with water and dried (MgSO$_4$). Removal of the solvent afforded the desired product as a crisp foam (21 mg). $\delta_H$ (CDCl$_3$) 1.72 (1H, dd, J 9.9 and 7.7 Hz), 1.85 (1H, m), 1.90 (1H, m), 2.32 (1H, m), 2.5–2.8 (4H, m), 5.16 (2H, s), 5.55 (1H, d, J 6.5 Hz), 6.54 (1H, d, J 6.5 Hz), 6.9–7.4 (9H, m), 7.58 (2H, d, J 8.7 Hz), 8.25 (2H, d, J 8.7 Hz) ppm. APCI [M–H]$^-$ 493.

EXAMPLE 55

N-(2'-RS-mercaptomethyl-4'-phenylbutanoyl)-p-(4-pyridylmethoxy)-D-phenylglycine (Diastereoisomers A and B)

The mixture of diastereoisomeric methyl esters (92 mg, 0.18 mmol) from Description 89 was suspended in methanol (2 ml) and treated with a solution of sodium sulphide nonahydrate (174 mg, 0.73 mmol) in water (2 ml). The suspension was stirred under argon for 2 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (66 mg). $\delta_H$ (CDCl$_3$) 1.32 and 1.65 (1H, dd), 1.82 (1H, m), 2.0 (1H, m), 2.32 (1H, m), 2.4–2.8 (4H, m), 5.14 (2H, s), 5.52 (1H, overlapping d), 6.8–7.7 (11H, m), 8.51 (2H, d, J 6.0 Hz), ppm. APCI [M–H]$^-$ 449.

EXAMPLE 56

N-(2'-RS-mercaptomethyl-4'-phenylbutanoyl)-p-(2-pyridylmethoxy)-D-phenylglycine
(Diastereoisomers A and B)

The mixture of diastereoisomeric methyl esters (83 mg, 0.16 mmol) from Description 90 was suspended in methanol (2 ml) and treated with a solution of sodium sulphide nonahydrate (157 mg, 0.65 mmol) in water (2 ml). The suspension was stirred under argon for 1 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (67 mg). $\delta_H$ (CDCl$_3$ $_{containing\ MeOD}$) 1.82 (1H, m) 2.0 (1H, m), 2.32 (1H, m), 2.4–2.8 (4H, m), 5.18 (2H, s), 5.49 (1H, overlapping d), 6.9–7.4 (10H, m), 7.5 (1H, d, J 7.8 Hz), 7.73 (1H, m), 8.56 (1H, d, J 4.9 Hz), ppm. ESMS [M–H]$^-$ 449.

EXAMPLE 57

N-(2'-RS-mercaptomethyl-4'-phenylbutanoyl)-p-(3-pyridylmethoxy)-D-phenylglycine
(Diastereoisomers A and B)

The mixture of diastereoisomeric methyl esters (104 mg, 0.20 mmol) from Description 91 was suspended in methanol (2 ml) and treated with a solution of sodium sulphide nonahydrate (197 mg, 0.80 mmol) in water (2 ml). The suspension was stirred under argon for 1.5 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (67 mg). $\delta_H$ (CDCl$_3$) 1.32 and 1.65 (1H, dd) 1.82 (1H, m), 2.0 (1H, m), 2.32 (1H, m), 2.4–2.8 (4H, m), 5.08 (2H, s), 5.54 (1H, overlapping d), 6.8–7.6 (10H, m), 7.85 (1H, d, J 8.0 Hz), 8.58 (2H, m) ppm. ESMS [M–H]$^-$ 449.

EXAMPLE 58

N-(2'-RS-mercaptomethyl-4'-phenylbutanoyl)-p-(p-acetamido)-benzyloxy-D-phenylglycine
(Diastereoisomers A and B)

The mixture of diastereoisomeric methyl esters (101 mg, 0.18 mmol) from Description 92 was suspended in methanol (2 ml) and treated with a solution of sodium sulphide nonahydrate (173 mg, 0.72 mmol) in water (2 ml). The suspension was stirred under argon for 2 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (91 mg). $\delta_H$ (DMSO-d6) 1.73 (2H, m) 2.04 (3H, s), 2.25 (1H, m), 2.4–2.8 (4H, m), 5.02 (2H, s), 5.30 (1H, overlapping d), 6.8–7.6 (11H, m), 8.64 and 8.69 (1H, d) ppm. ESMS [M–H]$^-$ 505.

EXAMPLE 59

N-(2'-mercaptomethyl-4'-phenylbutanoyl)-m-(m-carboxy)-benzyloxy-D-phenylglycine
(Diastereoisomer A)

The diastereoisomer A methyl ester (31 mg, 0.06 mmol) from Description 94 was suspended in methanol (2 ml) and treated with a solution of sodium sulphide nonahydrate (66 mg, 0.28 mmol) in water (2 ml). The suspension was stirred under argon for 3 hours. The reaction mixture was then washed with ethyl acetate and the aqueous layer acidified by addition of 5M hydrochloric acid solution (10 drops) and then extracted with ethyl acetate. The organic layer was washed with water and dried (MgSO$_4$). Removal of the solvent afforded the desired product as a crisp foam (30 mg). $\delta_H$ (CDCl$_3$) 1.37 (1H, t, J 8.9 Hz) 1.82 (1H, m), 1.98 (1H, m), 2.33 (1H, m), 2.5–2.8 (4H, m), 5.06 (2H, s), 5.60 (1H, d, J 6.6 Hz), 6.61 (1H, d, J 6.6 Hz), 6.9–7.6 (10H, m), 7.98 (2H, overlapping), 8.08 (1H, s) ppm. APCI [M–H]$^-$ 492.

EXAMPLE 60

N-(2'-mercaptomethyl-4'-phenylbutanoyl)-m-(m-carboxy)-benzyloxy-D-phenylglycine
(Diastereoisomer B)

The diastereoisomer B methyl ester (33 mg, 0.06 mmol) from Description 94 was suspended in methanol (2 ml) and treated with a solution of sodium sulphide nonahydrate (70 mg, 0.29 mmol) in water (2 ml). The suspension was stirred under argon for 3 hours. The reaction mixture was then washed with ethyl acetate and the aqueous layer acidified by addition of 5M hydrochloric acid solution (10 drops) and then extracted with ethyl acetate. The organic layer was washed with water and dried (MgSO$_4$). Removal of the solvent afforded the desired product as a crisp foam (17 mg). $\delta_H$ (CDCl$_3$) 1.69 (1H, dd, J 10.0 and 7.7 Hz) 1.80 (1H, m), 1.96 (1H, m), 2.3–2.8 (5H, m), 5.07 (2H, s), 5.59 (1H, d, J 6.5 Hz), 6.6–8.0 (13H, m), 8.08 (1H, s) ppm. APCI [M–H]$^-$ 492.

EXAMPLE 61

N-(2'-mercaptomethyl-4'-phenylbutanoyl)-m-(p-carboxy)-benzyloxy-D-phenylglycine
(Diastereoisomer A)

The diastereoisomer A methyl ester (30 mg, 0.06 mmol) from Description 95 was suspended in methanol (2 ml) and treated with a solution of sodium sulphide nonahydrate (64 mg, 0.27 mmol) in water (2 ml). The suspension was stirred under argon for 4 hours. The reaction mixture was then washed with ethyl acetate and the aqueous layer acidified by addition of 5M hydrochloric acid solution (10 drops) and then extracted with ethyl acetate. The organic layer was washed with water and dried (MgSO$_4$). Removal of the solvent afforded the desired product as a crisp foam (28 mg). $\delta_H$ (CDCl$_3$+MeOD) 1.82 (1H, m), 1.98 (1H, m), 2.4–2.8 (5H, m), 5.11 (2H, s), 5.54 (1H, m), 6.9–7.5 (11H, m), 8.05 (2H, overlapping), ppm. ESMS [M–H]$^-$ 492.

EXAMPLE 62

N-(2'-mercaptomethyl-4'-phenylbutanoyl)-m-(p-carboxy)-benzyloxy-D-phenylglycine
(Diastereoisomer B)

The diastereoisomer B methyl ester (30 mg, 0.06 mmol) from Description 95 was suspended in methanol (2 ml) and treated with a solution of sodium sulphide nonahydrate (79 mg, 0.33 mmol) in water (2 ml). The suspension was stirred under argon for 4 hours. The reaction mixture was then washed with ethyl acetate and the aqueous layer acidified by addition of 5M hydrochloric acid solution (10 drops) and then extracted with ethyl acetate. The organic layer was washed with water and dried (MgSO$_4$). Removal of the solvent afforded the desired product as a crisp foam (24 mg). $\delta_H$ (CDCl$_3$+MeOD) 1.85 (1H, m), 1.93 (1H, m), 2.3–2.7 (5H, m), 5.10 (2H, s), 5.54 (1H, m), 6.9–7.5 (11H, m), 8.05 (2H, m) ppm. ESMS [M–H]⁻ 492.

EXAMPLE 63

N-(2'-mercaptomethyl-4'-phenylbutanoyl)-p-(m-amino)-benzyloxy-D-phenylglycine
(Diastereoisomer A)

The diastereoisomer A methyl ester (36 mg, 0.07 mmol) from Description 96 was suspended in methanol (2 ml) and treated with a solution of sodium sulphide nonahydrate (66 mg, 0.28 mmol) in water (2 ml). The suspension was stirred under argon for 3 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (30 mg). $\delta_H$ (CDCl$_3$+CD$_3$OD) 1.85 (1H, m), 1.95 (1H, s), 2.4–2.8 (5H, m), 4.98 (2H, s), 5.47 (1H, m), ), 6.7–7.3 (13H, m) ppm. ESMS M–H 463.

EXAMPLE 64

N-(2'-mercaptomethyl-4'-phenylbutanoyl)-p-(m-amino)-benzyloxy-D-phenylglycine
(Diastereoisomer B)

The diastereoisomer B methyl ester (30 mg, 0.06 mmol) from Description 96 was suspended in methanol (2 ml) and treated with a solution of sodium sulphide nonahydrate (55 mg, 0.23 mmol) in water (2 ml). The suspension was stirred under argon for 3 hours. The reaction mixture was then washed with ethyl acetate and the aqueous layer acidified by addition of 5M hydrochloric acid solution (10 drops) and then extracted with ethyl acetate. The organic layer was washed with water and dried (MgSO$_4$). Removal of the solvent afforded the desired product as a crisp foam (24 mg). $\delta_H$ (CDCl$_3$+CD$_3$OD) 1.9 (2H, m), 2.4–2.8 (5H, m), 5.00 (2H, s), 5.48 (1H, m), ), 6.7–7.3 (13H, m) ppm. ESMS M–H 463.

EXAMPLE 65

N-(2'-mercaptomethyl-4'-phenylbutanoyl)-p-(p-dimethylamino)-phenethyloxy-D-phenylglycine
(Diastereoisomer A)

The diastereoisomer A methyl ester (26 mg, 0.05 mmol) from Description 97 was suspended in methanol (3 ml) and treated with a solution of sodium sulphide nonahydrate (44 mg, 0.19 mmol) in water (2 ml). The suspension was stirred under argon for 4 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (27 mg). $\delta_H$ (CDCl$_3$) 1.32 (1H, m), 1.82 (1H, m), 2.00 (1H, s), 2.3–2.8 (5H, m), 3.00 (8H, s), 4.13 (2H, m), 5.48 (1H, d, J 6.5 Hz), 6.68 (1H, d, J 6.5 Hz), 6.79 (2H, d, J 8.5 Hz), 7.3 (11H, m) ppm. ESMS MH⁺ 507.

EXAMPLE 66

N-(2'-mercaptomethyl-4'-phenylbutanoyl)-p-(p-dimethylamino)-phenethyloxy-D-phenylglycine
(Diastereoisomer B)

The diastereoisomer B methyl ester (48 mg, 0.09 mmol) from Description 97 was suspended in methanol (2 ml) and treated with a solution of sodium sulphide nonahydrate (82 mg, 0.34 mmol) in water (2 ml). The suspension was stirred under argon for 4 hours. The reaction mixture was then washed with ethyl acetate and the aqueous layer acidified by addition of 5M hydrochloric acid solution (10 drops) and then extracted with ethyl acetate. The organic layer was washed with water and dried (MgSO$_4$). Removal of the solvent afforded the desired product as a crisp foam (27 mg). $\delta_H$ (CDCl$_3$) 1.7 (1H, m), 1.8 (2H, m), 2.4–2.6 (3H, m), 2.8–3.0 (4H, m), 2.92 (6H, s), 4.17 (2H, m), 5.50 (1H, d, J 6.5 Hz), 6.60 (1H, d, J 6.5 Hz), 6.7–7.3 (13H, m) ppm. ESMS MH⁺ 507.

EXAMPLE 67

N-(2'-RS-mercaptomethyl-4'-phenylbutanoyl)-p-(N-methyl-3-pyridiniummethoxy)-D-phenylglycine
(Diastereoisomers A and B)

The mixture of diastereoisomeric methyl esters (110 mg, 0.17 mmol) from Description 98 was suspended in methanol (2 ml) and treated with a solution of sodium sulphide nonahydrate (163 mg, 0.68 mmol) in water (2 ml). The suspension was stirred under argon for 1.5 hours. The reaction mixture was adjusted to pH 6.5 by the addition of 1M hydrochloric acid and the solvent removed under reduced pressure to afford the desired product as a yellow solid (contaminated with sodium chloride). $\delta_H$ (DMSO-d$_6$) inter alia 4.38 (3H, s), 5.33 (2H, s), 5.38 (1H, m), 6.76 (1H, m), 8.15 (1H, m), 8.62 (1H, m), 9.00 (1H, m), 9.17 (1H, s) ppm.

EXAMPLE 68

N-(2'-mercaptomethyl-4'-phenylbutanoyl)-p-(p-benzyloxy)-benzyloxy-D-phenylglycine
(Diastereoisomer A)

The diastereoisomer A methyl ester (48 mg, 0.08 mmol) from Description 99 was suspended in methanol (3 ml) and treated with a solution of sodium sulphide nonahydrate (75 mg, 0.31 mmol) in water (1 ml). The suspension was stirred under argon for 3 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (44 mg). $\delta_H$ (CDCl$_3$) 1.36 (1H, dd, J 9.2 and 8.3 Hz), 1.85 (1H, m), 2.0 (1H, m), 2.3–2.8 (5H, m), 4.93 (2H, s), 5.06 (2H, s), 5.54 (1H, d, J 6.4 Hz), ), 6.48 (1H, d, J 6.4 Hz), 6.9 (4H, overlapping d), 7.1–7.4 (14H, m) ppm. ESMS [M–H]⁻ 554.

EXAMPLE 69

N-(2'-mercaptomethyl-4'-phenylbutanoyl)-p-(p-benzyloxy)-benzyloxy-D-phenylglycine
(Diastereoisomer B)

The diastereoisomer B methyl ester (48 mg, 0.08 mmol) from Description 99 was suspended in methanol (3 ml) and treated with a solution of sodium sulphide nonahydrate (75 mg, 0.31 mmol) in water (1 ml). The suspension was stirred under argon for 3 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (44 mg). $\delta_H$ (CDCl$_3$) 1.74 (1H, m), 1.85 (1H, m), 2.0 (1H, m), 2.3–2.8 (5H, m), 4.91 (2H, s), 5.03 (2H, s), 5.51 (1H, d), ), 6.50 (1H, d), 6.9 (4H, overlapping d), 7.1–7.4 (14H, m) ppm. EIMS [M–H]⁻ 554.

EXAMPLE 70

N-(2'-mercaptomethyl-4'-phenylbutanoyl)-p-(p-trifluoromethoxy)-benzyloxy-D-phenylglycine (Diastereoisomer A)

The diastereoisomer A methyl ester (60 mg, 0.10 mmol) from Description 100 was suspended in methanol (4 ml) and treated with a solution of sodium sulphide nonahydrate (98 mg, 0.41 mmol) in water (2 ml). The suspension was stirred under argon for 3 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (50 mg). $\delta_H$ (CDCl$_3$) 1.34 (1H, t, J 8.8 Hz), 1.85 (1H, m), 2.0 (1H, m), 2.3–2.8 (5H, m), 5.02 (2H, s), 5.55 (1H, d, J 6.4 Hz), 6.55 (1H, d, J 6.4 Hz), 6.94 (2H, d, J 8.6 Hz), 7.2–7.4 (11H, m) ppm. ESMS [M−H]$^-$ 532.

EXAMPLE 71

N-(2'-mercaptomethyl-4'-phenylbutanoyl)-p-(p-trifluoromethoxy)-benzyloxy-D-phenylglycine (Diastereoisomer B)

The diastereoisomer B methyl ester (63 mg, 0.11 mmol) from Description 100 was suspended in methanol (4 ml) and treated with a solution of sodium sulphide nonahydrate (103 mg, 0.43 mmol) in water (2 ml). The suspension was stirred under argon for 3 hours. The reaction mixture was then acidified by addition of 5M hydrochloric acid solution (10 drops) and diluted with ethyl acetate. The organic layer was washed with water and dried (MgSO$_4$). Removal of the solvent afforded the desired product as a crisp foam (56 mg). $\delta_H$ (CDCl$_3$) 1.75 (1H, dd, J 9.9 and 7.7 Hz), 1.85 (1H, m), 2.0 (1H, m), 2.3–2.8 (5H, m), 5.04 (2H, s), 5.55 (1H, d, J 6.5 Hz), 6.53 (1H, d, J 6.5 Hz), 7.0–7.5 (13H, m) ppm. ESMS [M−H]$^-$ 532.

BIOLOGICAL ACTIVITY

I$_{50}$ Screen

The inhibitory activity of the compounds of the invention was measured in 25 mM PIPES pH 7 buffer at 10 concentrations (1000, 333, 111, 37, 12.3, 4.1, 1.4, 0.46, 0.15 and 0.05 µM) at 37° C. using nitrocefin (91 µM final concentration) as the reporter substrate. The assays were performed with a 5 minute preincubation of enzyme and inhibitor and were conducted in the presence of added zinc sulphate (Zn$^{2+}$ 100 µM, final concentration). the methodology is described in detail in the following references: Payne et al (1991), *J. Antimicrob. Chemother.*, 28:255; Payne et al (1994), *Antimicrob. Agents and Chemother.*, 38:767.

Results

Compounds of the Examples exhibit I$_{50}$ values against *B. fragilis* CfiA metallo-β-lactamase of <1000 µM. The I$_{50}$ values for Examples 3, 4, 6–17, 19, 21, 24–33, 34 (more polar isomer) 35–38, 40–42, 44–46, 48, 50, 53, 55, 56, 58–64, 66, 67 and 69 were <1 µM.

All compounds of the above Examples exhibited significant inhibition of the *Stenotrophomonas maltophilia* L-1 (formerly *Xanthomonas maltophilia* L-1) and *Bacillus cereus* II metallo-β-lactamases, with I$_{50}$ values in the range 0.2–100 µM.

Antibacterial activity of compounds of the invention in combination with the carbapenem antibiotic, meropenem, against the *Bacteroides fragillis* 262 strain, which produces CfiA metallo-β-lactamase:

[MIC=minimum inhibitory concentration (µg/ml)]

Antibacterial activity of meropenem was potentiated as follows:

MIC (µg/ml) of meropenem alone:>128

| Inhibitor compound | MIC (µg/ml) of compound alone | MIC (µg/ml) of meropenem in the presence of 8 µg/ml of compound |
|---|---|---|
| Example 4 | >256 | 32 |
| Example 24 | >256 | 32 |
| Example 26 | >256 | 16 |

What is claimed is:

1. A compound of formula (I) or a pharmaceutically acceptable salt, solvate or in vivo hydrolysable ester thereof:

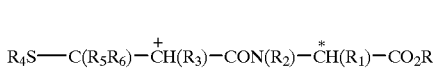

(I)

wherein:
R is hydrogen, a salt forming cation or an in vivo hydrolysable ester-forming group;
R$_1$ is selected from the group consisting of

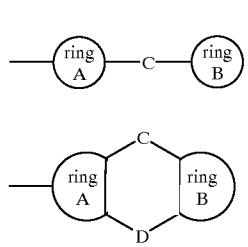

(a)

(b)

in which A is a monocyclic aryl or heteroaryl ring and B is a monocyclic aryl, alicyclic or heterocyclic ring, C and D are independently -Z$_p$-(CR$_8$CR$_9$)$_q$- or -(CR$_8$CR$_9$)$_q$-Z$_p$ where p is 0 or 1, q is 0 to 3 provided that p+q in C is not 0, R$_8$ and R$_9$ are independently hydrogen or (C$_{1-6}$)alkyl or together represent oxo and Z is O, NR$_{10}$ or S(O)$_x$ where R$_{10}$ is hydrogen, (C$_{1-6}$)alkyl or aryl(C$_{1-6}$)alkyl and x is 0–2, and wherein C and D are linked ortho to one another on each of rings A and B in formula (b);
R$_2$ is hydrogen, (C$_{1-6}$)alkyl or aryl(C$_{1-6}$)alkyl;
R$_3$ is hydrogen, (C$_{1-6}$)alkyl optionally substituted by up to three halogen atoms, (C$_{3-7}$)cycloalkyl, fused aryl(C$_{3-7}$)cycloalkyl, (C$_{3-7}$)cycloalkyl(C$_{2-6}$)alkyl, (C$_{2-6}$)alkenyl, (C$_{2-6}$)alkynyl, aryl, aryl-(CH$_2$)$_m$-X-(CH$_2$)$_n$, heterocyclyl or heterocyclyl-(CH$_2$)$_m$-X-(CH$_2$)$_n$, where m is 0 to 3, n is 1 to 3 and X is O, S(O)$_x$ where x is 0–2 or a bond;
R$_4$ is hydrogen, or an in vivo hydrolysable acyl group; and
R$_5$ and R$_6$ are independently hydrogen and (C$_{1-6}$)alkyl or together represent (CH$_2$)$_r$ where r is 2 to 5.

2. A compound according to claim 1 wherein R$_1$ is formula (a) and ring A is selected from 2,5-thienyl, 2,5-furyl, 1,2-phenyl, 1,3-phenyl and 1,4-phenyl, ring B is selected from phenyl optionally substituted by one or two hydroxy or by methoxy, dimethylamino, carboxy or nitro, 2-furyl, 2-, 3- or 4-pyridyl, 1-tetrazolyl, 2-tetrazolyl, 1-triazolyl, 2-triazolyl, 2 thienyl and imidazolin-2,5-dione-1-yl and C is selected from CH$_2$, O or OCH$_2$.

3. A compound according to claim 1 wherein $R_1$ is formula (b), rings A and B are both phenyl, C is O, $CH_2$ or $NR_{10}$ and D is a bond (p+q=0).

4. A compound according to claim 1 wherein $R_1$ is selected from (5-benzyl)thien-2-yl, (5-benzyl)furan-2-yl, 5-(1-tetrazolylmethyl)thien-2-yl, 5-(2-tetrazolylmethyl)thien-2-yl, 5-(imidazolin-2,5-dione-1-ylmethyl)thien-2-yl, 5-(1-triazolylmethyl)thien-2-yl, 5-(2-triazolylmethyl)thien-2-yl, 3-phenoxyphenyl, 2-phenoxyphenyl, 4-phenoxyphenyl, 3-(4-hydroxybenzyl)phenyl, 3-(4-methoxybenzyl)phenyl, 4-benzyloxyphenyl, 4-(2-thienylmethyloxy)phenyl, 1-fluorenyl, 3-(N-ethylcarbazolyl) 4-hydroxybenzyloxy-4-phenyl, 4-methoxybenzyloxy-4-phenyl, 4-dimethylaminobenzyloxy-4-phenyl, 4-carboxybenzyloxy-4-phenyl, 3-carboxybenzyloxy-4-phenyl, (2-pyridyl)-methoxy-4-phenyl, (4-pyridyl)-methoxy-4-phenyl, 5-[1-(4-carbamoyltriazolyl)-methyl]-thien-2-yl, 5-[1-(4-carboxytriazolyl)-methyl]-thien-2-yl, (2-furyl)-methoxy-4-phenyl and dibenzofuranyl.

5. A compound according to claim 1 wherein $R_1$ is 4-benzyloxyphenyl 3- or 4-substituted in the benzyl group by a substituent selected from halogen, mercapto, $(C_{1-6})$ alkyl optionally substituted by 1–3 halo, phenyl, phenyl$(C_{1-6})$alkyl, phenyl$(C_{1-6})$alkoxy, $(C_{1-6})$alkoxy optionally substituted by 1–3 halo, hydroxy$(C_{1-6})$alkyl, mercapto$(C_{1-6})$alkyl, hydroxy, $CO_2R_7$, $N(R_7)_2$ or $CON(R_7)_2$ where each $R_7$ is independently hydrogen, $(C_{1-6})$ alkyl or $(C_{1-6})$ alkanoyl, $OCONH_2$, nitro, $(C_{1-6})$ alkylcarbonyloxy, $(C_{1-6})$ alkoxycarbonyl$(C_{1-6})$ alkyl, formyl and $(C_{1-6})$ alkylcarbonyl groups.

6. A compound according to claim 1 wherein $R_2$ is hydrogen, methyl or benzyl.

7. A compound according to claim 1 wherein $R_3$ is selected from methyl, isobutyl, phenyl-$(CH_2)_{1-5}$, phenoxyethyl, 1-indanyl, 3,4-dihydroxybenzyl, 4-hydroxycarbonyl-phenylethyl, 2-trifluoromethylquinolin-6-yl, 4-difluoromethoxy-phenylethyl and 3-methyl-2,4,5-tricarbonylimidaxol-1-yl.

8. A compound according to claim 1 wherein $R_4$ is hydrogen, $R_5$ and $R_6$ are independently hydrogen or methyl.

9. A compound according to claim 1 wherein the stereochemistry at the carbon atom marked * is D-.

10. A compound according to claim 1 wherein the stereochemistry at the carbon atom marked (+) is S.

11. A compound selected from the group consisting of:

N-(2'-mercaptomethyl-4'-phenylbutanoyl)-m-benzyl-phenylglycine (Diastereoisomer A or B);

N-(2'-mercaptomethyl-4'-phenylbutanoyl)-m-phenoxy-phenylglycine (Diastereoisomer A or B);

N-(2'-mercaptomethyl-4'-phenylbutanoyl)-m-(p-methoxybenzyl)-phenylglycine (Diastereoisomer A or B);

N-(2'-mercaptomethyl-4'-phenylbutanoyl)-m-benzyloxy-phenylglycine;

N-(2'-mercaptomethyl-4'-phenylbutanoyl)-m-(p-hydroxybenzyl)-phenylglycine;

N-(2'-mercaptomethyl-4'-phenylbutanoyl)-(1-fluorenyl) glycine;

N-(2'-mercaptomethyl-4'-phenylbutanoyl)-o-phenoxy-phenylglycine (Diastereoisomer A or B);

N-(2'-mercaptomethyl-4'-phenylbutanoyl)-p-phenoxy-phenylglycine (Diastereoisomer A or B);

N-(2'-mercaptomethyl-4'-phenylbutanoyl)-m-(p-methoxyphenoxy)-phenylglycine (Diastereoisomer A or B);

N-(2'-mercaptomethyl-4'-phenylbutanoyl)-(N-Ethyl-3-carbazolyl)glycine (Diastereoisomer A or B);

N-(2'-mercaptomethyl-4'-phenylbutanoyl)-p-benzyloxy-D-phenylglycine (Diastereoisomer A or B);

N-(2'-mercaptomethyl-4'-phenylbutanoyl)-p-(2"-thienylmethoxy)-D-phenylglycine (Diastereoisomer A or B);

N-(2'-mercaptomethyl-4'-phenylbutanoyl)-p-(p-carboxy)-benzyloxy-D-phenylglycine (Diastereoisomer A or B);

2-[(5-Benzyl)thien-2yl]-N-[2-(mercaptomethyl)-4-phenylbutyryl]glycine;

2-[(5-Benzyl)furan-2yl]-N-[2-(mercaptomethyl)-4-phenylbutyryl]glycine;

2-[5-(Tetrahydrofuran-3-ylmethyl)thien-2-yl]-N-[2-(mercaptomethyl)-4-phenylbutyryl]glycine;

2-[5-(1-Tetrazolylmethyl)thien-2-yl]-N-[2-(mercaptomethyl)-4-phenylbutyryl]glycine;

2-[5-(2-Tetrazolylmethyl)thien-2-yl]-N-[2-(mercaptomethyl)-4-phenylbutyryl]glycine;

2-[5-(1,2,3-Triazol-1-ylmethyl)thien-2-yl]-N-[2-(mercaptomethyl)-4-phenylbutyryl]glycine;

2-[5-(1,2,3-Triazol-2-ylmethyl)thien-2-yl]-N-[2-(mercaptomethyl)-4-phenylbutyryl]glycine;

2-[5-(Imidazolidin-2,4-dion-3-ylmethyl)thien-2-yl]-N-[2-(mercaptomethyl)-4-phenylbutyryl]glycine;

2-[5-(4-methoxybenzyl)thien-2-yl]-N-[2-(mercaptomethyl)-4-phenylbutyryl]glycine;

2-[(5-Benzyl)furan-2-yl]-N-[2-(mercaptomethyl)-3-phenylpropionylglycine;

2-[(5-Benzyl)thien-2-yl]-N-[2-(mercaptomethyl)-4-phenylbutyryl]glycine;

2-[5-(4,5-Dicarboxytriazol-1-ylmethyl)thien-2-yl]-N-[2-(mercaptomethyl)-4-phenylbutyryl]glycine;

2-[(5-(4-Carboxamidotriazol-1-ylmethyl)thien-2-yl]-N-[2-(mercaptomethyl)-4-phenylbutyryl]glycine;

2-[(5-(4-Carboxytriazol-1-ylmethyl)thien-2-yl]-N-[2-(mercaptomethyl)-4-phenylbutyryl]glycine;

2-[(5-(5-Carboxytriazol-1-ylmethyl)thien-2-yl]-N-[2-(mercaptomethyl)-4-phenylbutyryl]glycine;

N-(2'-mercaptomethyl-4'-phenylbutanoyl)-p-(p-methoxy)-benzyloxy-D-phenylglycine Diastereoisomer A or B);

N-(2'-mercaptomethyl-4'-phenylbutanoyl)-(3"-dibenzofuranyl) glycine (Diastereoisomer A or B);

N-(2'-mercaptomethyl-4'-phenylbutanoyl)-p-(2"-furanylmethoxy)-D-phenylglycine Diastereoisomer A or B);

N-(2'-mercaptomethyl-4'-phenylbutanoyl)-p-(p-hydroxy)-benzyloxy-D-phenylglycine Diastereoisomer A or B);

N-(2'-mercaptomethyl-4'-phenylbutanoyl)-p-(p-dimethylamino)-benzyloxy-D-phenylglycine Diastereoisomer A or B);

N-(2'-mercaptomethyl-4'-phenylbutanoyl)-p-(m-carboxy)-benzyloxy-D-phenylglycine Diastereoisomer A or B);

N-(2'-mercaptomethyl-4'-phenylbutanoyl)-p-(3,4-dihydroxy)-benzyloxy-D-phenylglycine Diastereoisomer A or B);

N-(2'-mercaptomethyl-4'-phenylbutanoyl)-p-(p-nitro)-benzyloxy-D-phenylglycine Diastereoisomer A or B);

N-(2'-RS-mercaptomethyl-4'-phenylbutanoyl)-p-(4-pyridylmethoxy)-D-phenylglycine;

N-(2'-RS-mercaptomethyl-4'-phenylbutanoyl)-p-(2-pyridylmethoxy)-D-phenylglycine;

N-(2'-RS-mercaptomethyl-4'-phenylbutanoyl)-p-(3-pyridylmethoxy)-D-phenylglycine;

N-(2'-RS-mercaptomethyl-4'-phenylbutanoyl)-p-(p-acetamido)-benzyloxy-D-phenylglycine;

N-(2'-mercaptomethyl-4'-phenylbutanoyl)-m-(m-carboxy)-benzyloxy-D-phenylglycine Diastereoisomer A or B);

N-(2'-mercaptomethyl-4'-phenylbutanoyl)-m-(p-carboxy)-benzyloxy-D-phenylglycine Diastereoisomer A or B);

N-(2'-mercaptomethyl-4'-phenylbutanoyl)-p-(m-amino)-benzyloxy-D-phenylglycine Diastereoisomer A or B);

N-(2'-mercaptomethyl-4'-phenylbutanoyl)-p-(p-dimethylamino)-phenethyloxy-D-phenylglycine Diastereoisomer A or B);

N-(2'-RS-mercaptomethyl-4'-phenylbutanoyl)-p-(N-methyl-3-pyridiniummethoxy)-D-phenylglycine;

N-(2'-mercaptomethyl-4'-phenylbutanoyl)-p-(p-benzyloxy)-benzyloxy-D-phenylglycine Diastereoisomer A or B) or N-(2'-mercaptomethyl-4'-phenylbutanoyl)-p-(p-trifluoromethoxy)-benzyloxy-D-phenylglycine Diastereoisomer A or B).

12. A process for preparing a compound of formula (I):

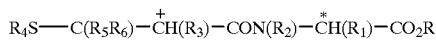

wherein:
R is hydrogen, a salt forming cation or an in vivo hydrolysable ester-forming group;
$R_1$ is selected from the group consisting of

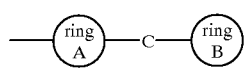

(a)

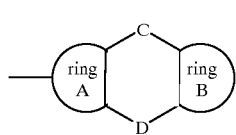

(b)

in which A is a monocyclic aryl or heteroaryl ring and B is a monocyclic aryl, alicyclic or heterocyclic ring, C and D are independently $-Z_p-(CR_8CR_9)_q-$ or $-(CR_8CR_9)_q-Z_p$ where p is 0 or 1, q is 0 to 3 provided that p+q in C is not 0, $R_8$ and $R_9$ are independently hydrogen or $(C_{1-6})$alkyl or together represent oxo and Z is O, $NR_{10}$ or $S(O)_x$ where $R_{10}$ is hydrogen, $(C_{1-6})$alkyl or aryl$(C_{1-6})$alkyl and x is 0–2, and wherein C and D are linked ortho to one another on each of rings A and B in formula (b);

$R_2$ is hydrogen, $(C_{1-6})$alkyl or aryl$(C_{1-6})$alkyl;

$R_3$ is hydrogen, $(C_{1-6})$alkyl optionally substituted by up to three halogen atoms, $(C_{3-7})$cycloalkyl, fused aryl$(C_{3-7})$ cycloalkyl, $(C_{3-7})$cycloalkyl$(C_{2-6})$alkyl, $(C_{2-6})$alkenyl, $(C_{2-6})$alkynyl, aryl, aryl-$(CH_2)_m$-X-$(CH_2)_n$, heterocyclyl or heterocyclyl-$(CH_2)_m$-X-$(CH_2)_n$, where m is 0 to 3, n is 1 to 3 and X is O, $S(O)_x$ where x is 0–2 or a bond;

$R_4$ is hydrogen, or an in vivo hydrolysable acyl group; and
$R_5$ and $R_6$ are independently hydrogen and $(C_{1-6})$alkyl or together represent $(CH_2)_r$ where r is 2 to 5;

which process comprises reacting a compound of formula (II)

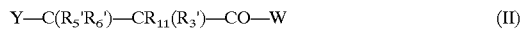

with a compound of formula (III)

wherein W is a leaving group, Y is Y' where Y' is $R_4$'S or a group convertible thereto and $R_{11}$ is H, or Y and $R_{11}$ together form a bond, $R^x$ is R or a carboxylate protecting group, $X^1$ is $N_3$ or $NHR_2$' and $R_1$', $R_2$', $R_3$', $R_4$', $R_5$' and $R_6$' are $R_1$, $R_2$, $R_3$, $R_4$, $R_5$ and $R_6$ or groups convertible thereto, and thereafter, where Y and $R_{11}$ form a bond, reacting the product with a nucleophilic sulphur reagent Y'H, where necessary, converting Y' into $R_4$'S, $R^x$, $R_1$', $R_2$', $R_3$' $R_4$', $R_5$' and/or $R_6$' into R, $R_1$, $R_2$, $R_3$, $R_4$, $R_5$ and/or $R_6$ and optionally inter-converting R, $R_1$, $R_2$, $R_3$, $R_4$, $R_5$ and/or $R_6$.

13. A pharmaceutical composition comprising a compound according to claim 1 together with a pharmaceutically acceptable carrier.

14. A pharmaceutical composition according to claim 13 which additionally comprises a β-lactam antibiotic.

15. A method of treatment of bacterial infections in humans or animals which comprises administering, in combination with a β-lactam antibiotic, a therapeutically effective amount of a compound of claim 1.

16. A compound of formula (IV):

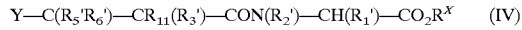

wherein

Y is Y' where Y' is $R_4$'S or a group convertible thereto and $R_{11}$ is H, or Y and $R_{11}$ together form a bond, $R^x$ is R or a carboxylate protecting group, $X^1$ is $N_3$ or $NHR_2$' and $R_1$', $R_2$', $R_3$', $R_4$', $R_5$' and $R_6$' are $R_1$, $R_2$, $R_3$, $R_4$, $R_5$ and $R_6$ or groups convertible thereto, and thereafter, where Y and $R_{11}$ for a bond, reacting the product with a nucleophilic sulphur reagent Y'H, where necessary, converting Y' into $R_4$'S, $R^x$, $R_1$', $R_2$', $R_3$' $R_4$', $R_5$' and/or $R_6$' into R, $R_1$, $R_2$, $R_3$, $R_4$, $R_5$ and/or $R_6$ and optionally inter-converting R, $R_1$, $R_2$, $R_3$, $R_4$, $R_5$ and/or $R_6$ provided that $R^x$ is other than R when $R_1$', $R_2$', $R_3$', $R_4$', $R_5$' and $R_6$' are $R_1$, $R_2$, $R_3$, $R_4$, $R_5$ and $R_6$ and excluding:

N-[2'-benzyl-3'-mercaptopropionyl]-3-hydroxyphenylglycine;

N-[S-lacetyl-2'-benzyl-3'-mercaptopropionyl]-3-hydroxyphenylglycine methyl ester;

N-[2'-benzyl-3'-mercaptopropionyl]-4-hydroxy-D-phenylglycine;

N-[S-lacetyl-2'-benzyl-3'-mercaptopropionyl]-4-hydroxy-D-phenylglycine ethyl ester;

N-[2'-benzyl-3'-mercaptopropionyl]-4-hydroxy-3-nitrophenylglycine;

N-[S-lacetyl-2'-benzyl-3'-mercaptopropionyl]-4-hydroxy-3-nitrophenylglycine methyl ester;

N-[2'-benzyl-3'-mercaptopropionyl]-3,4-dihydroxy-D-phenylglycine; and

N-[S-lacetyl-2'-benzyl-3'-mercaptopropionyl]-3,4-dihydroxy-D-phenylglycine methyl ester.

* * * * *